(12) United States Patent
Lamego et al.

(10) Patent No.: US 8,577,431 B2
(45) Date of Patent: Nov. 5, 2013

(54) NOISE SHIELDING FOR A NONINVASIVE DEVICE

(75) Inventors: Marcelo Lamego, Coto De Caza, CA (US); Sean Merritt, Lake Forest, CA (US); Cristiano Dalvi, Mission Viejo, CA (US); Hung Vo, Garden Grove, CA (US); Johannes Bruinsma, Mission Viejo, CA (US); Jeroen Poeze, Mission Viejo, CA (US); Ferdyan Lesmana, Irvine, CA (US); Greg Olsen, Trabuco Canyon, CA (US); Massi Joe E. Kiani, Laguna Niguel, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 918 days.

(21) Appl. No.: 12/497,528

(22) Filed: Jul. 2, 2009

(65) Prior Publication Data

US 2010/0004519 A1 Jan. 7, 2010

Related U.S. Application Data

(63) Continuation-in-part of application No. 29/323,409, filed on Aug. 25, 2008, now Pat. No. Des. 621,516, which is a continuation-in-part of application No. 29/323,408, filed on Aug. 25, 2008, now Pat. No. Des. 606,659.

(60) Provisional application No. 61/086,060, filed on Aug. 4, 2008, provisional application No. 61/086,108, filed on Aug. 4, 2008, provisional application No. 61/086,063, filed on Aug. 4, 2008, provisional application No. 61/086,057, filed on Aug. 4, 2008, provisional application No. 61/078,228, filed on Jul. 3, 2008, provisional application No. 61/078,207, filed on Jul. 3, 2008, provisional application No. 61/091,732, filed on Aug. 25, 2008.

(51) Int. Cl.
*A61B 5/1455* (2006.01)

(52) U.S. Cl.
USPC ............ 600/310; 600/316; 600/322; 600/323

(58) Field of Classification Search
USPC ......... 600/310, 316, 322, 323, 344, 473, 476, 600/326; 356/41
See application file for complete search history.

(56) References Cited

U.S. PATENT DOCUMENTS

| | | | |
|---|---|---|---|
| 4,114,604 | A | 9/1978 | Shaw et al. |
| 4,258,719 | A | 3/1981 | Lewyn |

(Continued)

FOREIGN PATENT DOCUMENTS

| | | |
|---|---|---|
| EP | 419223 | 3/1991 |
| WO | WO93/12712 | 7/1993 |
| WO | WO 00/25112 | 5/2000 |

OTHER PUBLICATIONS

International Search Report issued in Application No. PCT/US2009/052756, mailed Feb. 10, 2009 in 14 pages.

(Continued)

*Primary Examiner* — Eric Winakur
*Assistant Examiner* — Chu Chuan (JJ) Liu
(74) *Attorney, Agent, or Firm* — Knobbe Martens Olson & Bear LLP

(57) ABSTRACT

A noninvasive physiological sensor for measuring one or more physiological parameters of a medical patient can include a bump interposed between a light source and a photodetector. The bump can be placed in contact with body tissue of a patient and thereby reduce a thickness of the body tissue. As a result, an optical pathlength between the light source and the photodetector can be reduced. In addition, the sensor can include a heat sink that can direct heat away from the light source. Moreover, the sensor can include shielding in the optical path between the light source and the photodetector. The shielding can reduce noise received by the photodetector.

21 Claims, 43 Drawing Sheets

(56) References Cited

U.S. PATENT DOCUMENTS

| | | | |
|---|---|---|---|
| 4,267,844 A | 5/1981 | Yamanishi |
| 4,444,471 A | 4/1984 | Ford, Jr. et al. |
| 4,655,225 A | 4/1987 | Dähne et al. |
| 4,755,676 A | 7/1988 | Gaalema et al. |
| 4,781,195 A | 11/1988 | Martin |
| 4,805,623 A | 2/1989 | Jöbsis |
| 4,880,304 A * | 11/1989 | Jaeb et al. ................. 356/41 |
| 4,960,128 A | 10/1990 | Gordon et al. |
| 4,964,408 A | 10/1990 | Hink et al. |
| 5,028,787 A | 7/1991 | Rosenthal et al. |
| 5,035,243 A | 7/1991 | Muz |
| 5,041,187 A | 8/1991 | Hink et al. |
| 5,069,213 A | 12/1991 | Polczynski |
| 5,069,214 A | 12/1991 | Samaras et al. |
| 5,077,476 A | 12/1991 | Rosenthal |
| D326,715 S | 6/1992 | Schmidt |
| 5,131,391 A | 7/1992 | Sakai et al. |
| 5,137,023 A | 8/1992 | Mendelson et al. |
| 5,159,929 A | 11/1992 | Morris et al. |
| 5,163,438 A | 11/1992 | Gordon et al. |
| 5,222,496 A | 6/1993 | Clarke et al. |
| 5,249,576 A | 10/1993 | Goldberger et al. |
| 5,278,627 A | 1/1994 | Aoyagi et al. |
| 5,297,548 A * | 3/1994 | Pologe ................. 600/310 |
| 5,319,355 A | 6/1994 | Russek |
| 5,337,744 A | 8/1994 | Branigan |
| 5,337,745 A | 8/1994 | Benaron |
| 5,341,805 A | 8/1994 | Stavridi et al. |
| 5,362,966 A | 11/1994 | Rosenthal et al. |
| D353,195 S | 12/1994 | Savage et al. |
| D353,196 S | 12/1994 | Savage et al. |
| 5,377,676 A | 1/1995 | Vari et al. |
| D356,870 S | 3/1995 | Ivers et al. |
| D359,546 S | 6/1995 | Savage et al. |
| 5,431,170 A | 7/1995 | Mathews |
| D361,840 S | 8/1995 | Savage et al. |
| 5,437,275 A | 8/1995 | Amundsen et al. |
| 5,441,054 A | 8/1995 | Tsuchiya |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,034 A | 1/1996 | Lewis et al. |
| 5,482,036 A | 1/1996 | Diab et al. |
| 5,490,505 A | 2/1996 | Diab et al. |
| 5,494,043 A | 2/1996 | O'Sullivan et al. |
| 5,511,546 A | 4/1996 | Hon |
| 5,533,511 A | 7/1996 | Kaspari et al. |
| 5,534,851 A | 7/1996 | Russek |
| 5,553,615 A | 9/1996 | Carim et al. |
| 5,553,616 A | 9/1996 | Ham et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| D378,414 S | 3/1997 | Allen et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,676,143 A | 10/1997 | Simonsen et al. |
| 5,685,299 A | 11/1997 | Diab et al. |
| D390,666 S | 2/1998 | Lagerlof |
| D393,830 S | 4/1998 | Tobler et al. |
| 5,743,262 A | 4/1998 | Lepper, Jr. et al. |
| 5,750,927 A | 5/1998 | Baltazar |
| 5,752,914 A * | 5/1998 | Delonzor et al. ............. 600/310 |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,792,052 A | 8/1998 | Isaacson et al. |
| 5,810,734 A | 9/1998 | Caro et al. |
| 5,823,950 A | 10/1998 | Diab et al. |
| 5,826,885 A | 10/1998 | Helgeland |
| 5,830,131 A | 11/1998 | Caro et al. |
| 5,833,618 A | 11/1998 | Caro et al. |
| D403,070 S | 12/1998 | Maeda et al. |
| 5,860,919 A | 1/1999 | Kiani-Azarbayjany et al. |
| 5,890,929 A | 4/1999 | Mills et al. |
| 5,902,235 A | 5/1999 | Lewis et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| D414,870 S | 10/1999 | Saltzstein et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,049,727 A | 4/2000 | Crothall |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,866 A | 11/2000 | Miesel et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,172,743 B1 | 1/2001 | Kley et al. |
| 6,181,958 B1 | 1/2001 | Steuer et al. |
| 6,184,521 B1 | 2/2001 | Coffin, IV et al. |
| 6,206,830 B1 | 3/2001 | Diab et al. |
| 6,223,063 B1 | 4/2001 | Chaiken et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,278,889 B1 | 8/2001 | Robinson |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| D452,012 S | 12/2001 | Phillips |
| 6,334,065 B1 | 12/2001 | Al-Ali et al. |
| 6,343,224 B1 | 1/2002 | Parker |
| 6,345,194 B1 | 2/2002 | Nelson et al. |
| 6,349,228 B1 | 2/2002 | Kiani et al. |
| 6,353,750 B1 | 3/2002 | Kimura et al. |
| 6,360,113 B1 | 3/2002 | Dettling |
| 6,360,114 B1 | 3/2002 | Diab et al. |
| 6,360,115 B1 | 3/2002 | Greenwald et al. |
| D455,834 S | 4/2002 | Oonars et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| D463,561 S | 9/2002 | Fukatsu et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |

(56) References Cited

U.S. PATENT DOCUMENTS

| | | |
|---|---|---|
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,509 B2 | 8/2003 | Schmitt |
| 6,606,511 B1 | 8/2003 | Ali et al. |
| D481,459 S | 10/2003 | Nahm |
| 6,632,181 B2 | 10/2003 | Flaherty et al. |
| 6,636,759 B2 * | 10/2003 | Robinson .................... 600/310 |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Gruhl |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| D502,655 S | 3/2005 | Huang |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| D508,862 S | 8/2005 | Behar et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| D510,625 S | 10/2005 | Widener et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| D514,461 S | 2/2006 | Harju |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| D535,031 S | 1/2007 | Barrett et al. |
| D537,164 S | 2/2007 | Shigemori et al. |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| D547,454 S | 7/2007 | Hsieh et al. |
| 7,239,905 B2 | 7/2007 | Kiani-Azarbayjany et al. |
| 7,245,953 B1 | 7/2007 | Parker |
| D549,830 S | 8/2007 | Behar et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| D550,364 S | 9/2007 | Glover et al. |
| D551,350 S | 9/2007 | Lorimer et al. |
| 7,272,425 B2 | 9/2007 | Al-Ali |
| 7,274,955 B2 | 9/2007 | Kiani et al. |
| D553,248 S | 10/2007 | Nguyen et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| D562,985 S | 2/2008 | Brefka et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| D567,125 S | 4/2008 | Okabe et al. |
| 7,355,512 B1 | 4/2008 | Al-Ali |
| 7,356,365 B2 | 4/2008 | Schurman |
| D569,001 S | 5/2008 | Omaki |
| D569,521 S | 5/2008 | Omaki |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |

(56) References Cited

U.S. PATENT DOCUMENTS

| | | |
|---|---|---|
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,606,606 B2 | 10/2009 | Laakkonen |
| D603,966 S | 11/2009 | Jones et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| 7,657,294 B2 | 2/2010 | Eghbal et al. |
| 7,657,295 B2 | 2/2010 | Coakley et al. |
| 7,657,296 B2 | 2/2010 | Raridan et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 2002/0016536 A1* | 2/2002 | Benni .......................... 600/323 |
| 2002/0052547 A1 | 5/2002 | Toida |
| 2002/0091322 A1 | 7/2002 | Chaiken et al. |
| 2002/0115918 A1 | 8/2002 | Crowley |
| 2004/0039272 A1* | 2/2004 | Abdul-Hafiz et al. ........ 600/322 |
| 2004/0049237 A1 | 3/2004 | Larson et al. |
| 2004/0054269 A1 | 3/2004 | Rantala et al. |
| 2004/0054291 A1 | 3/2004 | Schulz et al. |
| 2005/0162761 A1 | 7/2005 | Hargis et al. |
| 2006/0167347 A1 | 7/2006 | Xu et al. |
| 2006/0189859 A1 | 8/2006 | Kiani et al. |
| 2006/0208191 A1 | 9/2006 | Kessler et al. |
| 2006/0211924 A1 | 9/2006 | Dalke et al. |
| 2006/0258922 A1* | 11/2006 | Mason et al. ................. 600/323 |
| 2007/0165218 A1 | 7/2007 | Qing et al. |
| 2007/0197886 A1 | 8/2007 | Naganuma et al. |
| 2007/0293792 A1 | 12/2007 | Sliwa et al. |
| 2008/0036855 A1 | 2/2008 | Heenan |
| 2008/0071154 A1 | 3/2008 | Hausmann et al. |
| 2008/0130232 A1 | 6/2008 | Yamamoto et al. |
| 2008/0139908 A1 | 6/2008 | Kurth |
| 2008/0208006 A1 | 8/2008 | Farr |
| 2009/0043180 A1 | 2/2009 | Tschautscher et al. |
| 2009/0105565 A1 | 4/2009 | Xu |
| 2009/0163775 A1 | 6/2009 | Barrett et al. |
| 2009/0259114 A1 | 10/2009 | Johnson et al. |
| 2010/0004518 A1 | 1/2010 | Vo et al. |
| 2010/0049018 A1* | 2/2010 | Duffy et al. ................... 600/323 |
| 2010/0090118 A1 | 4/2010 | Rozenfeld |

OTHER PUBLICATIONS

International Preliminary Report on Patentability and Written Opinion of the International Searching Authority issued in Application No. PCT/US2009/052756, mailed Feb. 8, 2011 in 8 pages.

International Search Report and Written Opinion for PCT/US2009/049638, mailed Jan. 7, 2010.

Burritt, Mary F.; Current Analytical Approaches to Measuring Blood Analytes; vol. 36; No. 8(B); 1990.

Hall, et al., Jeffrey W.; Near-Infrared Spectrophotometry: A New Dimension in Clinical Chemistry; vol. 38; No. 9; 1992.

Kuenstner, et al., J. Todd; Measurement of Hemoglobin in Unlysed Blood by Near-Infrared Spectroscopy; vol. 48; No. 4, 1994.

Manzke, et al., B., Multi Wavelength Pulse Oximetry in the Measurement of Hemoglobin Fractions; vol. 2676.

Naumenko, E. K.; Choice of Wavelengths for Stable Determination of Concentrations of Hemoglobin Derivatives from Absorption Spectra of Erythrocytes; vol. 63; No. 1; pp. 60-66 Jan.-Feb. 1996; Original article submitted Nov. 3, 1994.

Schmitt, Joseph M.; Simple Photon Diffusion Anaylsis of the Effects of Multiple Scattering on Pulse Oximetry; Mar. 14, 1991; revised Aug. 30, 1991.

Schmitt, et al., Joseph M.; Measurement of Blood Hematocrit by Dual-Wavelength near-IR Photoplethysmography; vol. 1641; 1992.

Schnapp, et al., L.M.; Pulse Oximetry. Uses and Abuses.; Chest 1990; 98; 1244-1250 DOI 10.1378/Chest.98.5.1244.

PCT International Search Report, App. No. PCT/US2010/047899, Date of Actual Completion of Search: Jan. 26, 2011, 4 pages.

International Preliminary Report on Patentability and Written Opinion of the International Searching Authority issued in Application No. PCT US2009/049638, mailed Jan. 5, 2011 in 9 pages.

http://www.masimo.com/rainbow/pronto.htm Noninvasive & Immediate Hemoglobin Testing, printed on Aug. 20, 2009.

http://www.masimo.com/pulseOximeter/Rad5.htm; Signal Extraction Pulse Oximeter, printed on Aug. 20, 2009.

http://blogderoliveira.blogspot.com/2008_02_01_archive.html; Ricardo Oliveira, printed on Aug. 20, 2009.

(56) References Cited

OTHER PUBLICATIONS http://www.masimo.com/rad-57/; Noninvasive Measurement of Methemoglobin, Carboxyhemoglobin and Oxyhemoglobin in the blood. Printed on Aug. 20, 2009.

http://amivital.ugr.es/blog/?tag+spo2; Monitorizacion de la hemoglobina . . . y mucho mas, printed on Aug. 20, 2009.

http://www.masimo.com/spco/; Carboxyhemoglobin Noninvasive > Continuous > Immediate, printed on Aug. 20, 2009.

http://www.masimo.com/PARTNERS/WELCHALLYN.htm; Welch Allyn Expands Patient Monitor Capabilities with Masimo Pulse Oximetry Technology, printed on Aug. 20, 2009.

http://www.masimo.com/pulseOximeter/PPO.htm; Masimo Personal Pulse Oximeter, printed on Aug. 20, 2009.

http://www.masimo.com/generalFloor/system.htm; Masimo Patient SafetyNet System at a Glance, printed on Aug. 20, 2009.

European Office Action issued in application No. 10763901.5 on Jan. 11, 2013.

* cited by examiner

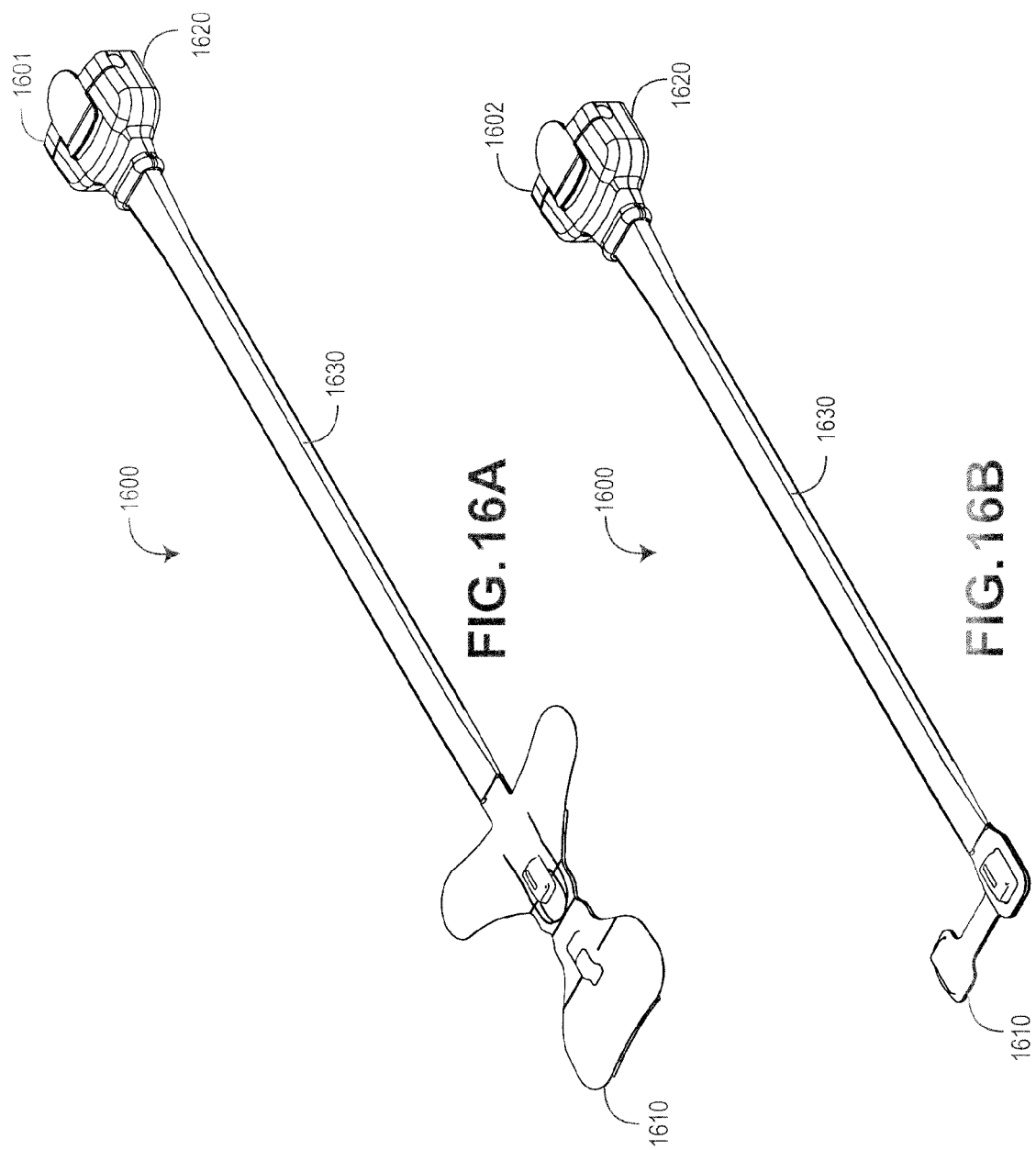

NOISE SHIELDING FOR A NONINVASIVE DEVICE

RELATED APPLICATIONS

This application claims the benefit of priority under 35 U.S.C. §119(e) of the following U.S. Provisional Patent Applications:

| App. No. | Filing Date | Title | Attorney Docket |
|---|---|---|---|
| 61/086,060 | Aug. 4, 2008 | Multi-Stream Data Collection System For Non-Invasive Measurement of Glucose and Other Analytes | MLHUM.002PR |
| 61/086,108 | Aug. 4, 2008 | Multi-Stream Sensor Front Ends for Noninvasive Measurement of Glucose and Other Analytes | MLHUM.003PR |
| 61/086,063 | Aug. 4, 2008 | Multi-Stream Detector For Noninvasive Measurement Of Glucose And Other Analytes | MLHUM.004PR |
| 61/086,057 | Aug. 4, 2008 | Multi-Stream Emitter For Noninvasive Measurement Of Glucose And Other Analytes | MLHUM.005PR |
| 61/078,228 | Jul. 3, 2008 | Noise Shielding For A Non-Invasive Device | MLHUM.006PR |
| 61/078,207 | Jul. 3, 2008 | Contoured Protrusion for Improving Spectroscopic Measurement of Blood Constituents | MLHUM.007PR |
| 61/091,732 | Aug. 25, 2008 | Sensor For Improving Measurement Of Blood Constituents | MLHUM.011PR |

This application also claims the benefit of priority under 35 U.S.C. §120 as a continuation-in-part of the following U.S. Design Patent Applications:

| App. No. | Filing Date | Title | Attorney Docket |
|---|---|---|---|
| 29/323,409 | Aug. 25, 2008 | Patient Monitoring Sensor | MLHUM.009DA |
| 29/323,408 | Aug. 25, 2008 | Patient Monitor | MLHUM.010DA |

The foregoing applications are hereby incorporated by reference in their entirety.

BACKGROUND

The standard of care in caregiver environments includes patient monitoring through spectroscopic analysis using, for example, a pulse oximeter. Devices capable of spectroscopic analysis generally include a light source(s) transmitting optical radiation into or reflecting off a measurement site, such as, body tissue carrying pulsing blood. After attenuation by tissue and fluids of the measurement site, a photodetection device(s) detects the attenuated light and outputs a detector signal(s) responsive to the detected attenuated light. A signal processing device(s) process the detector(s) signal(s) and outputs a measurement indicative of a blood constituent of interest, such as glucose, oxygen, met hemoglobin, total hemoglobin, other physiological parameters, or other data or combinations of data useful in determining a state or trend of wellness of a patient.

In noninvasive devices and methods, a sensor is often adapted to position a finger proximate the light source and light detector. For example, noninvasive sensors often include a clothespin-shaped housing that includes a contoured bed conforming generally to the shape of a finger. The contoured bed positions the finger for measurement and attempts to stabilize it.

Unfortunately, this type of contour cannot be ideal, especially for measuring blood constituents like glucose.

SUMMARY

This disclosure describes embodiments of noninvasive methods, devices, and systems for measuring a blood analyte, such as oxygen, carbon monoxide, methemoglobin, total hemoglobin, glucose, proteins, glucose, lipids, a percentage thereof (e.g., saturation) or for measuring many other physiologically relevant patient characteristics. These characteristics can relate, for example, to pulse rate, hydration, trending information and analysis, and the like. In certain embodiments, a noninvasive sensor interfaces with tissue at a measurement site and deforms the tissue in a way that increases signal gain in certain desired wavelengths. In an embodiment, a protrusion can be provided in a finger bed of a noninvasive sensor for a patient's finger. The protrusion can reduce tissue thickness, thereby sometimes increasing signal gain by tens of times or even more. This protrusion can include different sizes and shapes depending on the tissue site and the desired blood analyte to be measured.

In disclosed embodiments, the protrusion is employed in noninvasive sensors to assist in measuring and detecting various analytes. The disclosed noninvasive sensor can also include, among other things, emitters and detectors positioned to produce multi-stream sensor information. The noninvasive sensor can have different architectures and can include or be coupled to other components, such as a display device, a network interface, and the like. The protrusion can be employed in any type of noninvasive sensor.

In certain embodiments, a noninvasive physiological sensor for measuring one or more physiological parameters of a medical patient can include a bump interposed between a light source and a photodetector. The bump can be placed in contact with body tissue of a patient and thereby reduce a thickness of the body tissue. As a result, an optical pathlength between the light source and the photodetector can be reduced. In addition, the sensor can include a heat sink that can direct heat away from the light source. Moreover, the sensor can include shielding in the optical path between the light source and the photodetector. The shielding can reduce noise received by the photodetector.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIGS. 16A and 16B illustrate embodiments of disposable optical sensors; and

DETAILED DESCRIPTION

Figure 1:
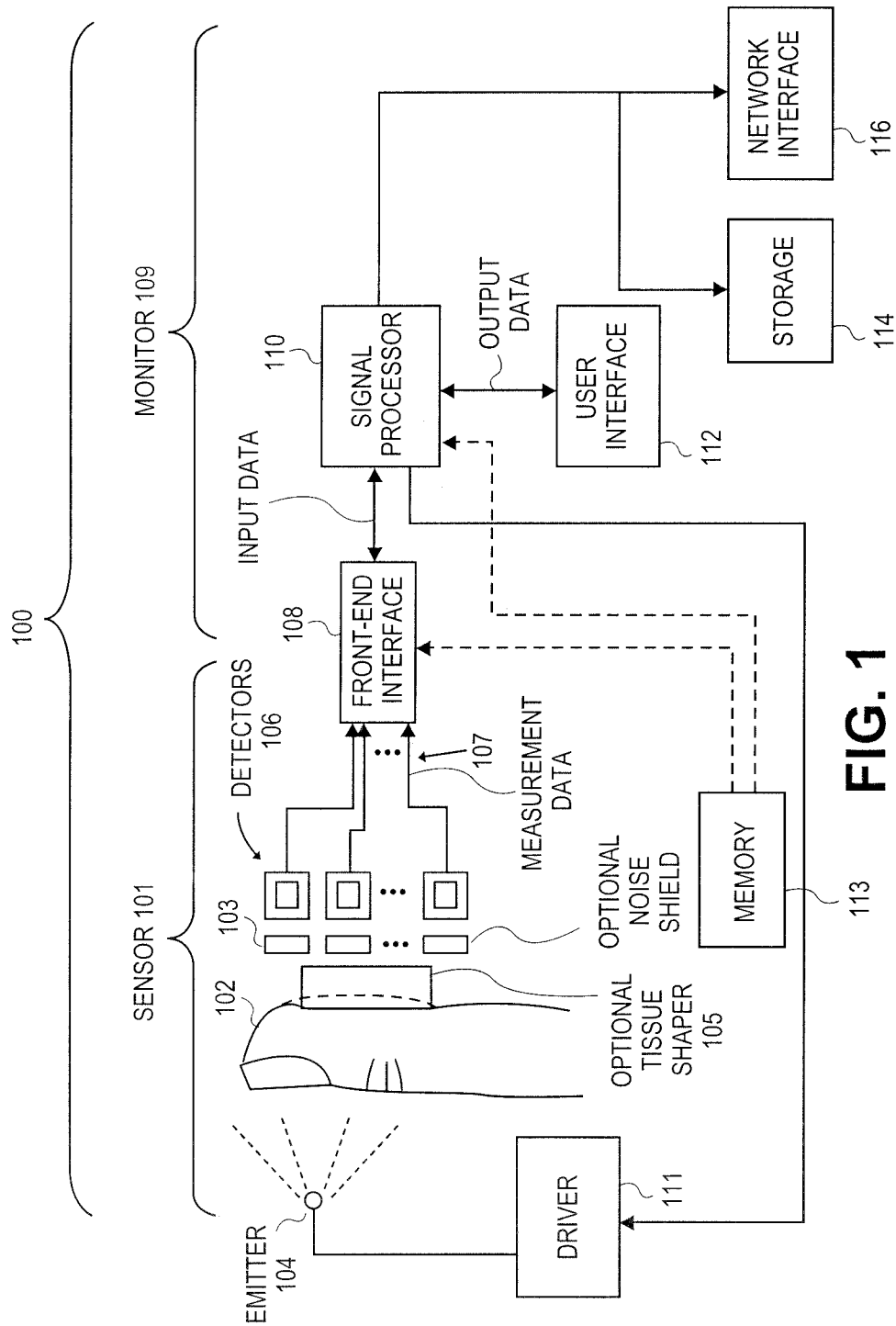
FIG. 1 illustrates a block diagram of an example data collection system capable of noninvasively measuring one or more blood analytes in a monitored patient, according to an embodiment of the disclosure.

The present disclosure generally relates to non-invasive medical devices. In an embodiment, a physiological sensor includes a detector housing that can be coupled to a measurement site, such as a patient's finger. The sensor housing can include a curved bed that can generally conform to the shape of the measurement site. In addition, the curved bed can include a protrusion shaped to increase an amount of light radiation from the measurement site. In an embodiment, the protrusion is used to thin out the measurement site. This allows the light radiation to pass through less tissue, and accordingly is attenuated less. In an embodiment, the protrusion can be used to increase the area from which attenuated light can be measured. In an embodiment, this is done through the use of a lens which collects attenuated light exiting the measurement site and focuses onto one or more detectors. The protrusion can advantageously include plastic, including a hard opaque plastic, such as a black or other colored plastic, helpful in reducing light noise. In an embodiment, such light noise includes light that would otherwise be detected at a photodetector that has not been attenuated by tissue of the measurement site of a patient sufficient to cause the light to adequately included information indicative of one or more physiological parameters of the patient. Such light noise includes light piping.

In an embodiment, the protrusion can be formed from the curved bed, or can be a separate component that is positionable with respect to the bed. In an embodiment, a lens made from any appropriate material is used as the protrusion. The protrusion can be convex in shape. The protrusion can also be sized and shaped to conform the measurement site into a flat or relatively flat surface. The protrusion can also be sized to conform the measurement site into a rounded surface, such as, for example, a concave or convex surface. The protrusion can include a cylindrical or partially cylindrical shape. The protrusion can be sized or shaped differently for different types of patients, such as an adult, child, or infant. The protrusion can also be sized or shaped differently for different measurement sites, including, for example, a finger, toe, hand, foot, ear, forehead, or the like. The protrusion can thus be helpful in any type of noninvasive sensor. The external surface of the protrusion can include one or more openings or windows. The openings can be made from glass to allow attenuated light from a measurement site, such as a finger, to pass through to one or more detectors. Alternatively, some of all of the protrusion can be a lens, such as a partially cylindrical lens.

The sensor can also include a shielding, such as a metal enclosure as described below or embedded within the protrusion to reduce noise. The shielding can be constructed from a conductive material, such as copper, in the form of a metal cage or enclosure, such as a box. The shielding can include a second set of one or more openings or windows. The second set of openings can be made from glass and allow light that has passed through the first set of windows of the external surface of the protrusion to pass through to one or more detectors that can be enclosed, for example, as described below.

In various embodiments, the shielding can include any substantially transparent, conductive material placed in the optical path between an emitter and a detector. The shielding can be constructed from a transparent material, such as glass, plastic, and the like. The shielding can have an electrically conductive material or coating that is at least partially transparent. The electrically conductive coating can be located on one or both sides of the shielding, or within the body of the shielding. In addition, the electrically conductive coating can be uniformly spread over the shielding or may be patterned. Furthermore, the coating can have a uniform or varying thickness to increase or optimize its shielding effect. The shielding can be helpful in virtually any type of noninvasive sensor that employs spectroscopy.

In an embodiment, the sensor can also include a heat sink. In an embodiment, the heat sink can include a shape that is functional in its ability to dissipate excess heat and aesthetically pleasing to the wearer. For example, the heat sink can be configured in a shape that maximizes surface area to allow for greater dissipation of heat. In an embodiment, the heat sink includes a metalicized plastic, such as plastic including carbon and aluminum to allow for improved thermal conductivity and diffusivity. In an embodiment, the heat sink can advantageously be inexpensively molded into desired shapes and configurations for aesthetic and functional purposes. For example, the shape of the heat sink can be a generally curved surface and include one or more fins, undulations, grooves or channels, or combs.

In the present disclosure, a sensor can measure various blood analytes noninvasively using multi-stream spectroscopy. In an embodiment, the multi-stream spectroscopy can employ visible, infrared and near infrared wavelengths. As disclosed herein, the sensor is capable of noninvasively measuring blood analytes or percentages thereof (e.g., saturation) based on various combinations of features and components.

The sensor can include photocommunicative components, such as an emitter, a detector, and other components. The emitter can include a plurality of sets of optical sources that, in an embodiment, are arranged together as a point source. The various optical sources can emit a sequence of optical radiation pulses at different wavelengths towards a measurement site, such as a patient's finger. Detectors can then detect optical radiation from the measurement site. The optical sources and optical radiation detectors can operate at any appropriate wavelength, including, as discussed herein, infrared, near infrared, visible light, and ultraviolet. In addition, the optical sources and optical radiation detectors can operate at any appropriate wavelength, and such modifications to the embodiments desirable to operate at any such wavelength will be apparent to those skilled in the art. In certain embodiments, multiple detectors are employed and arranged in a spatial geometry. This spatial geometry provides a diversity of path lengths among at least some of the detectors and allows for multiple bulk and pulsatile measurements that are robust. Each of the detectors can provide a respective output stream based on the detected optical radiation, or a sum of output streams can be provided from multiple detectors. In some embodiments, the sensor can also include other components, such as one or more heat sinks and one or more thermistors.

The sensor can be coupled to one or more monitors that process and/or display the sensor's output. The monitors can include various components, such as a sensor front end, a signal processor, a display, etc.

The sensor can be integrated with a monitor, for example, into a handheld unit including the sensor, a display and user controls. In other embodiments, the sensor can communicate with one or more processing devices. The communication can be via wire(s), cable(s), flex circuit(s), wireless technologies, or other suitable analog or digital communication methodologies and devices to perform those methodologies. Many of the foregoing arrangements allow the sensor to be attached to the measurement site while the device is attached elsewhere on a patient, such as the patient's arm, or placed at a location near the patient, such as a bed, shelf or table. The sensor or monitor can also provide outputs to a storage device or network interface.

Reference will now be made to the Figures to discuss embodiments of the present disclosure.

FIG. 1 illustrates an example of a data collection system 100. In certain embodiments, the data collection system 100 noninvasively measure a blood analyte, such as oxygen, carbon monoxide, methemoglobin, total hemoglobin, glucose, proteins, glucose, lipids, a percentage thereof (e.g., saturation) or for measuring many other physiologically relevant patient characteristics. The system 100 can also measure additional blood analytes and/or other physiological parameters useful in determining a state or trend of wellness of a patient.

The data collection system 100 can be capable of measuring optical radiation from the measurement site. For example, in some embodiments the data collection system 100 can employ photodiodes defined in terms of area. In an embodiment, the area is from about 1 $mm^2$-5 $mm^2$ (or higher) that are capable of detecting about 100 nanoamps (nA) or less of current resulting from measured light at full scale. In addition to having its ordinary meaning, the phrase "at full scale" can mean light saturation of a photodiode amplifier (not shown). Of course, as would be understood by a person of skill in the art from the present disclosure various other sizes and types of photodiodes can be used with the embodiments of the present disclosure.

The data collection system 100 can measure a range of approximately about 2 nA to about 100 nA full scale. The data collection system 100 can also include sensor front-ends that are capable of processing and amplifying current from the detector(s) at signal-to-noise ratios (SNRs) of about 100 decibels (dB) or more, such as about 120 dB in order to measure various desired analytes. The data collection system 100 can operate with a lower SNR if less accuracy is desired for an analyte like glucose.

The data collection system 100 can measure analyte concentrations, including glucose, at least in part by detecting light attenuated by a measurement site 102. The measurement site 102 can be any location on a patient's body, such as a finger, foot, ear lobe, or the like. For convenience, this disclosure is described primarily in the context of a finger measurement site 102. However, the features of the embodiments disclosed herein can be used with other measurement sites 102.

In the depicted embodiment, the system 100 includes an optional tissue thickness adjuster or tissue shaper 105, which can include one or more protrusions, bumps, lenses, or other suitable tissue-shaping mechanisms. In certain embodiments, the tissue shaper 105 is a flat or substantially flat surface that can be positioned proximate the measurement site 102 and that can apply sufficient pressure to cause the tissue of the measurement site 102 to be flat or substantially flat. In other embodiments, the tissue shaper 105 is a convex or substantially convex surface with respect to the measurement site 102. Many other configurations of the tissue shaper 105 are possible. Advantageously, in certain embodiments, the tissue shaper 105 reduces thickness of the measurement site 102 while preventing or reducing occlusion at the measurement site 102. Reducing thickness of the cite can advantageously reduce the amount of attenuation of the light because the there is less tissue through which the light must travel. Shaping the tissue in to a convex (or alternatively concave) surface can also provide more surface area from which light can be detected.

The embodiment of the data collection system 100 shown also includes an optional noise shield 103. In an embodiment, the noise shield 103 can be advantageously adapted to reduce electromagnetic noise while increasing the transmittance of light from the measurement site 102 to one or more detectors 106 (described below). For example, the noise shield 103 can advantageously include a conductive coated glass or metal grid electrically communicating with one or more other shields of the sensor 101. In an embodiment where the noise shield 103 includes conductive coated glass, the coating can advantageously include indium tin oxide. In an embodiment, the indium tin oxide includes a surface resistivity ranging from approximately from 30 ohms per square inch to 500 ohms per square inch. In an embodiment, the resistivity is approximately 30, 200, or 500 ohms per square inch. As would be understood by a person of skill in the art from the present disclosure, other resistivities can also be used which are less than 30 ohms or more than 500 ohms. Other conductive materials transparent or substantially transparent to light can be used instead.

In some embodiments, the measurement site 102 is somewhere along a non-dominant arm or a non-dominant hand, e.g., a right-handed person's left arm or left hand. In some patients, the non-dominant arm or hand can have less musculature and higher fat content, which can result in less water content in that tissue of the patient. Tissue having less water content can provide less interference with the particular wavelengths that are absorbed in a useful manner by blood analytes like glucose. Accordingly, in some embodiments, the data collection system 100 can be used on a person's non-dominant hand or arm.

The data collection system 100 can include a sensor 101 (or multiple sensors) that is coupled to a processing device or physiological monitor 109. In an embodiment, the sensor 101 and the monitor 109 are integrated together into a single unit. In another embodiment, the sensor 101 and the monitor 109 are separate from each other and communicate one with another in any suitable manner, such as via a wired or wireless connection. The sensor 101 and monitor 109 can be attachable and detachable from each other for the convenience of the user or caregiver, for ease of storage, sterility issues, or the like. The sensor 101 and the monitor 109 will now be further described.

In the depicted embodiment shown in FIG. 1, the sensor 101 includes an emitter 104, a tissue shaper 105, a set of detectors 106, and a front-end interface 108. The emitter 104 can serve as the source of optical radiation transmitted towards measurement site 102. As will be described in further detail below, the emitter 104 can include one or more sources of optical radiation, such as LEDs, laser diodes, incandescent bulbs with appropriate frequency-selective filters, combinations of the same, or the like. In an embodiment, the emitter 104 includes sets of optical sources that are capable of emitting visible and near-infrared optical radiation.

In some embodiments, the emitter 104 is used as a point optical source, and thus, the one or more optical sources of the emitter 104 can be located within a close distance to each other, such as within about a 2 mm to about 4 mm. The emitters 104 can be arranged in an array, such as is described in U.S. Publication No. 2006/0211924, filed Sep. 21, 2006, titled "Multiple Wavelength Sensor Emitters," the disclosure of which is hereby incorporated by reference in its entirety. In particular, the emitters 104 can be arranged at least in part as described in paragraphs [0061] through [0068] of the aforementioned publication, which paragraphs are hereby incorporated specifically by reference. Other relative spatial relationships can be used to arrange the emitters 104.

For analytes like glucose, currently available non-invasive techniques often attempt to employ light near the water absorbance minima at or about 1600 nm. Typically, these devices and methods employ a single wavelength or single band of wavelengths at or about 1600 nm. However, to date, these techniques have been unable to adequately consistently measure analytes like glucose based on spectroscopy.

In contrast, the emitter 104 of the data collection system 100 can emit, in certain embodiments, combinations of optical radiation in various bands of interest. For example, in some embodiments, for analytes like glucose, the emitter 104 can emit optical radiation at three (3) or more wavelengths between about 1600 nm to about 1700 nm. In particular, the emitter 104 can emit optical radiation at or about 1610 nm, about 1640 nm, and about 1665 nm. In some circumstances, the use of three wavelengths within about 1600 nm to about 1700 nm enable sufficient SNRs of about 100 dB, which can result in a measurement accuracy of about 20 mg/DL or better for analytes like glucose.

In other embodiments, the emitter 104 can use two (2) wavelengths within about 1600 nm to about 1700 nm to advantageously enable SNRs of about 85 dB, which can result in a measurement accuracy of about 25-30 mg/DL or better for analytes like glucose. Furthermore, in some embodiments, the emitter 104 can emit light at wavelengths above about 1670 nm. Measurements at these wavelengths can be advantageously used to compensate or confirm the contribution of protein, water, and other non-hemoglobin species exhibited in measurements for analytes like glucose conducted between about 1600 nm and about 1700 nm. Of course, other wavelengths and combinations of wavelengths can be used to measure analytes and/or to distinguish other types of tissue, fluids, tissue properties, fluid properties, combinations of the same or the like.

For example, the emitter 104 can emit optical radiation across other spectra for other analytes. In particular, the emitter 104 can employ light wavelengths to measure various blood analytes or percentages (e.g., saturation) thereof. For example, in one embodiment, the emitter 104 can emit optical radiation in the form of pulses at wavelengths about 905 nm, about 1050 nm, about 1200 nm, about 1300 nm, about 1330 nm, about 1610 nm, about 1640 nm, and about 1665 nm. In another embodiment, the emitter 104 can emit optical radiation ranging from about 860 nm to about 950 nm, about 950 nm to about 1100 nm, about 1100 nm to about 1270 nm, about 1250 nm to about 1350 nm, about 1300 nm to about 1360 nm, and about 1590 nm to about 1700 nm. Of course, the emitter 104 can transmit any of a variety of wavelengths of visible or near-infrared optical radiation.

Due to the different responses of analytes to the different wavelengths, certain embodiments of the data collection system 100 can advantageously use the measurements at these different wavelengths to improve the accuracy of measurements. For example, the measurements of water from visible and infrared light can be used to compensate for water absorbance that is exhibited in the near-infrared wavelengths.

As briefly described above, the emitter 104 can include sets of light-emitting diodes (LEDs) as its optical source. The emitter 104 can use one or more top-emitting LEDs. In particular, in some embodiments, the emitter 104 can include top-emitting LEDs emitting light at about 850 nm to 1350 nm.

The emitter 104 can also use super luminescent LEDs (SLEDs) or side-emitting LEDs. In some embodiments, the emitter 104 can employ SLEDs or side-emitting LEDs to emit optical radiation at about 1600 nm to about 1800 nm. Emitter 104 can use SLEDs or side-emitting LEDs to transmit near infrared optical radiation because these types of sources can transmit at high power or relatively high power, e.g., about 40 mW to about 100 mW. This higher power capability can be useful to compensate or overcome the greater attenuation of these wavelengths of light in tissue and water. For example, the higher power emission can effectively compensate and/or normalize the absorption signal for light in the mentioned wavelengths to be similar in amplitude and/or effect as other wavelengths that can be detected by one or more photodetectors after absorption. Alternatively, the emitter 104 can use other types of sources of optical radiation, such as a laser diode, to emit near-infrared light into the measurement site 102.

In addition, in some embodiments, in order to assist in achieving a comparative balance of desired power output between the LEDs, some of the LEDs in the emitter 104 can have a filter or covering that reduces and/or cleans the optical radiation from particular LEDs or groups of LEDs. For example, since some wavelengths of light can penetrate through tissue relatively well, LEDs, such as some or all of the top-emitting LEDs can use a filter or covering, such as a cap or painted dye. This can be useful in allowing the emitter 104 to use LEDs with a higher output and/or to equalize intensity of LEDs.

The data collection system 100 also includes a driver 111 that drives the emitter 104. The driver 111 can be a circuit or the like that is controlled by the monitor 109. For example, the driver 111 can provide pulses of current to the emitter 104. In an embodiment, the driver 111 drives the emitter 104 in a progressive fashion, such as in an alternating manner. The driver 111 can drive the emitter 104 with a series of pulses of about 1 milliwatt (mW) for some wavelengths that can penetrate tissue relatively well and from about 40 mW to about 100 mW for other wavelengths that tend to be significantly absorbed in tissue. A wide variety of other driving powers and driving methodologies can be used in various embodiments.

The driver 111 can be synchronized with other parts of the sensor 101 and can minimize or reduce jitter in the timing of pulses of optical radiation emitted from the emitter 104. In some embodiments, the driver 111 is capable of driving the emitter 104 to emit optical radiation in a pattern that varies by less than about 10 parts-per-million.

The detectors 106 capture and measure light from the measurement site 102. For example, the detectors 106 can capture and measure light transmitted from the emitter 104 that has been attenuated or reflected from the tissue in the measurement site 102. The detectors 106 can output a detector signal 107 responsive to the light captured or measured. The detectors 106 can be implemented using one or more photodiodes, phototransistors, or the like.

In addition, the detectors 106 can be arranged with a spatial configuration to provide a variation of path lengths among at least some of the detectors 106. That is, some of the detectors 106 can have the substantially, or from the perspective of the processing algorithm, effectively, the same path length from the emitter 104. However, according to an embodiment, at least some of the detectors 106 can have a different path length from the emitter 104 relative to other of the detectors 106. Variations in path lengths can be helpful in allowing the use of a bulk signal stream from the detectors 106.

The front end interface 108 provides an interface that adapts the output of the detectors 106, which is responsive to desired physiological parameters. For example, the front end interface 108 can adapt a signal 107 received from one or more of the detectors 106 into a form that can be processed by the monitor 109, for example, by a signal processor 110 in the monitor 109. The front end interface 108 can have its components assembled in the sensor 101, in the monitor 109, in connecting cabling (if used), combinations of the same, or the like. The location of the front end interface 108 can be chosen based on various factors including space desired for components, desired noise reductions or limits, desired heat reductions or limits, and the like.

The front end interface 108 can be coupled to the detectors 106 and to the signal processor 110 using a bus, wire, electrical or optical cable, flex circuit, or some other form of signal connection. The front end interface 108 can also be at least partially integrated with various components, such as the detectors 106. For example, the front end interface 108 can include one or more integrated circuits that are on the same circuit board as the detectors 106. Other configurations can also be used.

The front end interface 108 can be implemented using one or more amplifiers, such as transimpedance amplifiers, that are coupled to one or more analog to digital converters (ADCs) (which can be in the monitor 109), such as a sigma-delta ADC. A transimpedance-based front end interface 108 can employ single-ended circuitry, differential circuitry, and/or a hybrid configuration. A transimpedance-based front end interface 108 can be useful for its sampling rate capability and freedom in modulation/demodulation algorithms. For example, this type of front end interface 108 can advantageously facilitate the sampling of the ADCs being synchronized with the pulses emitted from the emitter 104.

The ADC or ADCs can provide one or more outputs into multiple channels of digital information for processing by the signal processor 110 of the monitor 109. Each channel can correspond to a signal output from a detector 106.

In some embodiments, a programmable gain amplifier (PGA) can be used in combination with a transimpedance-based front end interface 108. For example, the output of a transimpedance-based front end interface 108 can be output to a PGA that is coupled with an ADC in the monitor 109. A PGA can be useful in order to provide another level of amplification and control of the stream of signals from the detectors 106. Alternatively, the PGA and ADC components can be integrated with the transimpedance-based front end interface 108 in the sensor 101.

In another embodiment, the front end interface 108 can be implemented using switched-capacitor circuits. A switched-capacitor-based front end interface 108 can be useful for, in certain embodiments, its resistor-free design and analog averaging properties. In addition, a switched-capacitor-based front end interface 108 can be useful because it can provide a digital signal to the signal processor 110 in the monitor 109.

As shown in FIG. 1, the monitor 109 can include the signal processor 110 and a user interface, such as a display 112. The monitor 109 can also include optional outputs alone or in combination with the display 112, such as a storage device 114 and a network interface 116. In an embodiment, the signal processor 110 includes processing logic that determines measurements for desired analytes, such as glucose, based on the signals received from the detectors 106. The signal processor 110 can be implemented using one or more microprocessors or subprocessors (e.g., cores), digital signal processors, application specific integrated circuits (ASICs), field programmable gate arrays (FPGAs), combinations of the same, and the like.

The signal processor 110 can provide various signals that control the operation of the sensor 101. For example, the signal processor 110 can provide an emitter control signal to the driver 111. This control signal can be useful in order to synchronize, minimize, or reduce jitter in the timing of pulses emitted from the emitter 104. Accordingly, this control signal can be useful in order to cause optical radiation pulses emitted from the emitter 104 to follow a precise timing and consistent pattern. For example, when a transimpedance-based front end interface 108 is used, the control signal from the signal processor 110 can provide synchronization with the ADC in order to avoid aliasing, cross-talk, and the like. As also shown, an optional memory 113 can be included in the front-end interface 108 and/or in the signal processor 110. This memory 113 can serve as a buffer or storage location for the front-end interface 108 and/or the signal processor 110, among other uses.

The user interface 112 can provide an output, e.g., on a display, for presentation to a user of the data collection system 100. The user interface 112 can be implemented as a touch-screen display, an LCD display, an organic LED display, or the like. In addition, the user interface 112 can be manipulated to allow for measurement on the non-dominant side of patient. For example, the user interface 112 can include a flip screen, a screen that can be moved from one side to another on the monitor 109, or can include an ability to reorient its display indicia responsive to user input or device orientation. In alternative embodiments, the data collection system 100 can be provided without a user interface 112 and can simply provide an output signal to a separate display or system.

A storage device 114 and a network interface 116 represent other optional output connections that can be included in the monitor 109. The storage device 114 can include any computer-readable medium, such as a memory device, hard disk storage, EEPROM, flash drive, or the like. The various software and/or firmware applications can be stored in the storage device 114, which can be executed by the signal processor 110 or another processor of the monitor 109. The network interface 116 can be a serial bus port (RS-232/RS-485), a Universal Serial Bus (USB) port, an Ethernet port, a wireless interface (e.g., WiFi such as any 802.1x interface, including an internal wireless card), or other suitable communication device(s) that allows the monitor 109 to communicate and share data with other devices. The monitor 109 can also include various other components not shown, such as a microprocessor, graphics processor, or controller to output the user interface 112, to control data communications, to compute data trending, or to perform other operations.

Although not shown in the depicted embodiment, the data collection system 100 can include various other components or can be configured in different ways. For example, the sensor 101 can have both the emitter 104 and detectors 106 on the same side of the measurement site 102 and use reflectance to measure analytes. The data collection system 100 can also include a sensor that measures the power of light emitted from the emitter 104.

FIGS. 2A through 2D illustrate example monitoring devices 200 in which the data collection system 100 can be housed. Advantageously, in certain embodiments, some or all of the example monitoring devices 200 shown can have a shape and size that allows a user to operate it with a single hand or attach it, for example, to a patient's body or limb. Although several examples are shown, many other monitoring device configurations can be used to house the data collection system 100. In addition, certain of the features of the monitoring devices 200 shown in FIGS. 2A through 2D can be combined with features of the other monitoring devices 200 shown.

Figure 2A:
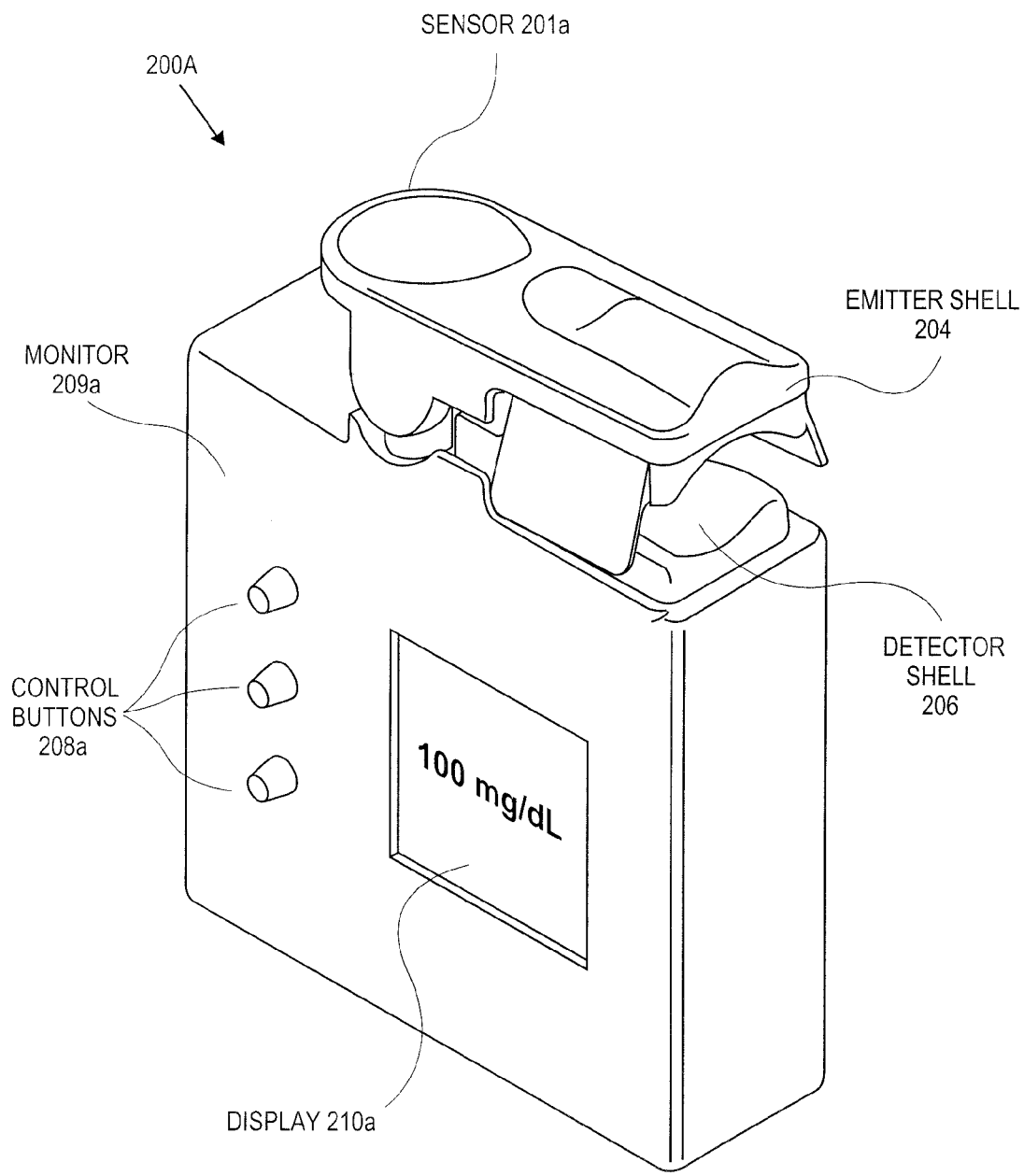
FIGS. 2A-2D illustrate an exemplary handheld monitor and an exemplary noninvasive optical sensor of the patient monitoring system of FIG. 1, according to embodiments of the disclosure.

Referring specifically to FIG. 2A, an example monitoring device 200A is shown, in which a sensor 201a and a monitor 209a are integrated into a single unit. The monitoring device 200A shown is a handheld or portable device that can measure glucose and other analytes in a patient's finger. The sensor 201a includes an emitter shell 204a and a detector shell 206a. The depicted embodiment of the monitoring device 200A also includes various control buttons 208a and a display 210a.

The sensor 201a can be constructed of white material used for reflective purposes (such as white silicone or plastic), which can increase usable signal at the detector 106 by forcing light back into the sensor 201a. Pads in the emitter shell 204a and the detector shell 206a can contain separated windows to prevent or reduce mixing of light signals, for example, from distinct quadrants on a patient's finger. In addition, these pads can be made of a relatively soft material, such as a gel or foam, in order to conform to the shape, for example, of a patient's finger. The emitter shell 204a and the detector shell 206a can also include absorbing black or grey material portions to prevent or reduce ambient light from entering into the sensor 201a.

In some embodiments, some or all portions of the emitter shell 204a and/or detector shell 206a can be detachable and/or disposable. For example, some or all portions of the shells 204a and 206a can be removable pieces. The removability of the shells 204a and 206a can be useful for sanitary purposes or for sizing the sensor 201a to different patients. The monitor 209a can include a fitting, slot, magnet, or other connecting mechanism to allow the sensor 201c to be removably attached to the monitor 209a.

The monitoring device 200a also includes optional control buttons 208a and a display 210a that can allow the user to control the operation of the device. For example, a user can operate the control buttons 208a to view one or more measurements of various analytes, such as glucose. In addition, the user can operate the control buttons 208a to view other forms of information, such as graphs, histograms, measurement data, trend measurement data, parameter combination views, wellness indications, and the like. Many parameters, trends, alarms and parameter displays could be output to the display 210a, such as those that are commercially available through a wide variety of noninvasive monitoring devices from Masimo® Corporation of Irvine, Calif.

Furthermore, the controls 208a and/or display 210a can provide functionality for the user to manipulate settings of the monitoring device 200a, such as alarm settings, emitter settings, detector settings, and the like. The monitoring device 200a can employ any of a variety of user interface designs, such as frames menus, touch-screens, and any type of button.

Figure 2B:
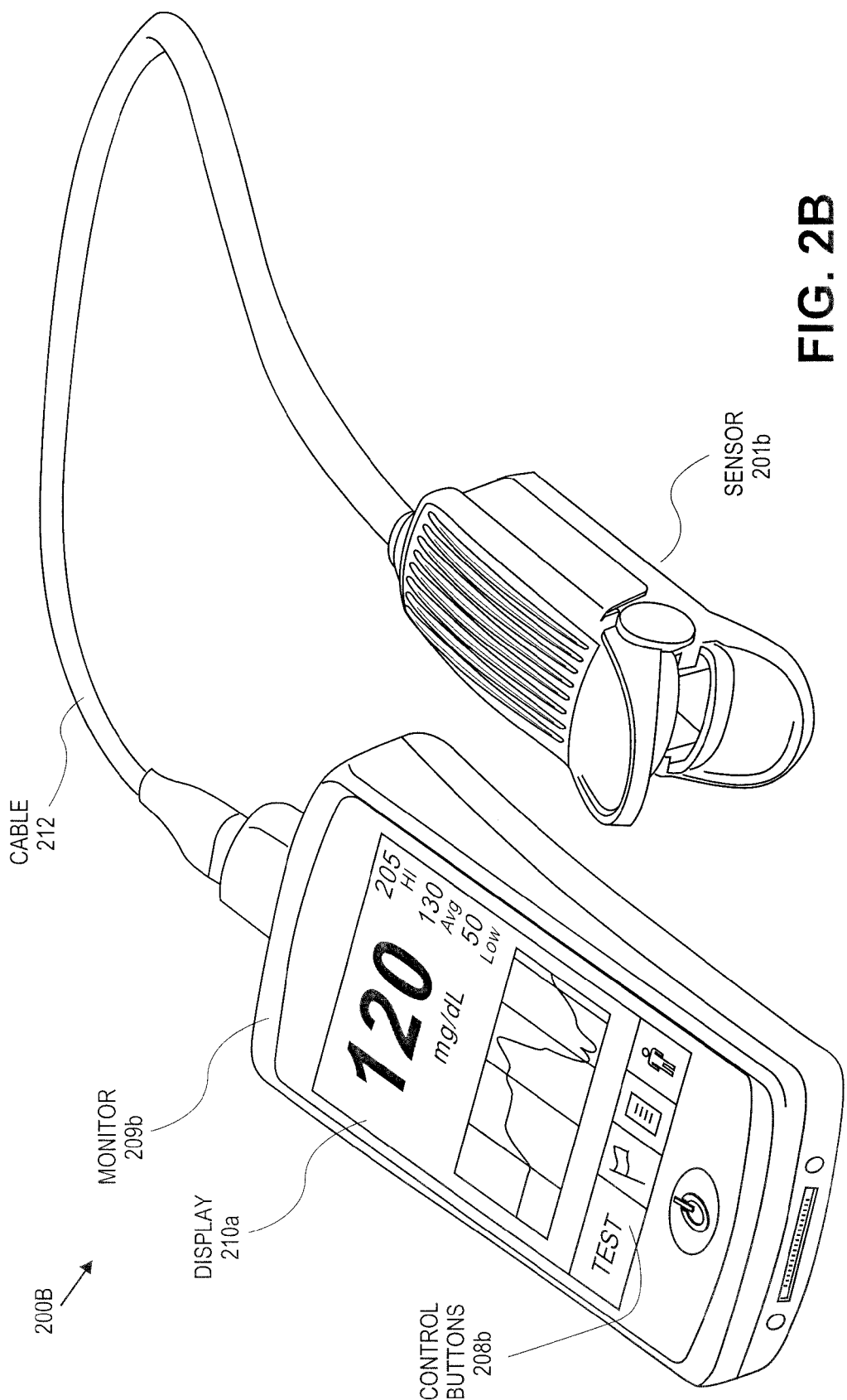

FIG. 2B illustrates another example of a monitoring device 200B. In the depicted embodiment, the monitoring device 200B includes a finger clip sensor 201b connected to a monitor 209b via a cable 212. In the embodiment shown, the monitor 209b includes a display 210b, control buttons 208b and a power button. Moreover, the monitor 209b can advantageously includes electronic processing, signal processing, and data storage devices capable of receiving signal data from said sensor 201b, processing the signal data to determine one or more output measurement values indicative of one or more physiological parameters of a monitored patient, and displaying the measurement values, trends of the measurement values, combinations of measurement values, and the like.

The cable 212 connecting the sensor 201b and the monitor 209b can be implemented using one or more wires, optical fiber, flex circuits, or the like. In some embodiments, the cable 212 can employ twisted pairs of conductors in order to minimize or reduce cross-talk of data transmitted from the sensor 201b to the monitor 209b. Various lengths of the cable 212 can be employed to allow for separation between the sensor 201b and the monitor 209b. The cable 212 can be fitted with a connector (male or female) on either end of the cable 212 so that the sensor 201b and the monitor 209b can be connected and disconnected from each other. Alternatively, the sensor 201b and the monitor 209b can be coupled together via a wireless communication link, such as an infrared link, radio frequency channel, or any other wireless communication protocol and channel.

The monitor 209b can be attached to the patient. For example, the monitor 209b can include a belt clip or straps (see, e.g., FIG. 2C) that facilitate attachment to to a patient's belt, arm, leg, or the like. The monitor 209b can also include a fitting, slot, magnet, LEMO snap-click connector, or other connecting mechanism to allow the cable 212 and sensor 201b to be attached to the monitor 209B.

The monitor 209b can also include other components, such as a speaker, power button, removable storage or memory (e.g., a flash card slot), an AC power port, and one or more network interfaces, such as a universal serial bus interface or an Ethernet port. For example, the monitor 209b can include a display 210b that can indicate a measurement for glucose, for example, in mg/dL. Other analytes and forms of display can also appear on the monitor 209b.

In addition, although a single sensor 201b with a single monitor 209b is shown, different combinations of sensors and device pairings can be implemented. For example, multiple sensors can be provided for a plurality of differing patient types or measurement sites or even patient fingers.

Figure 2C:
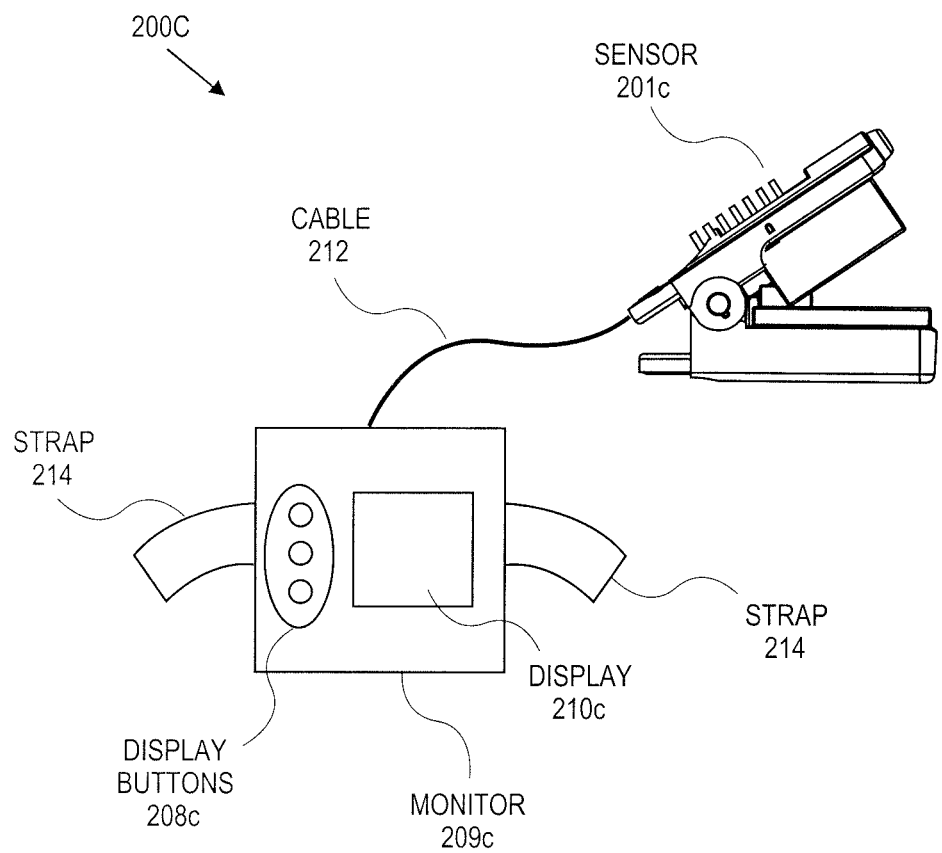

FIG. 2C illustrates yet another example of monitoring device 200C that can house the data collection system 100. Like the monitoring device 200B, the monitoring device 200C includes a finger clip sensor 201c connected to a monitor 209c via a cable 212. The cable 212 can have all of the features described above with respect to FIG. 2B. The monitor 209c can include all of the features of the monitor 200B described above. For example, the monitor 209c includes buttons 208c and a display 210c. The monitor 209c shown also includes straps 214c that allow the monitor 209c to be attached to a patients limb or the like.

Figure 2D:
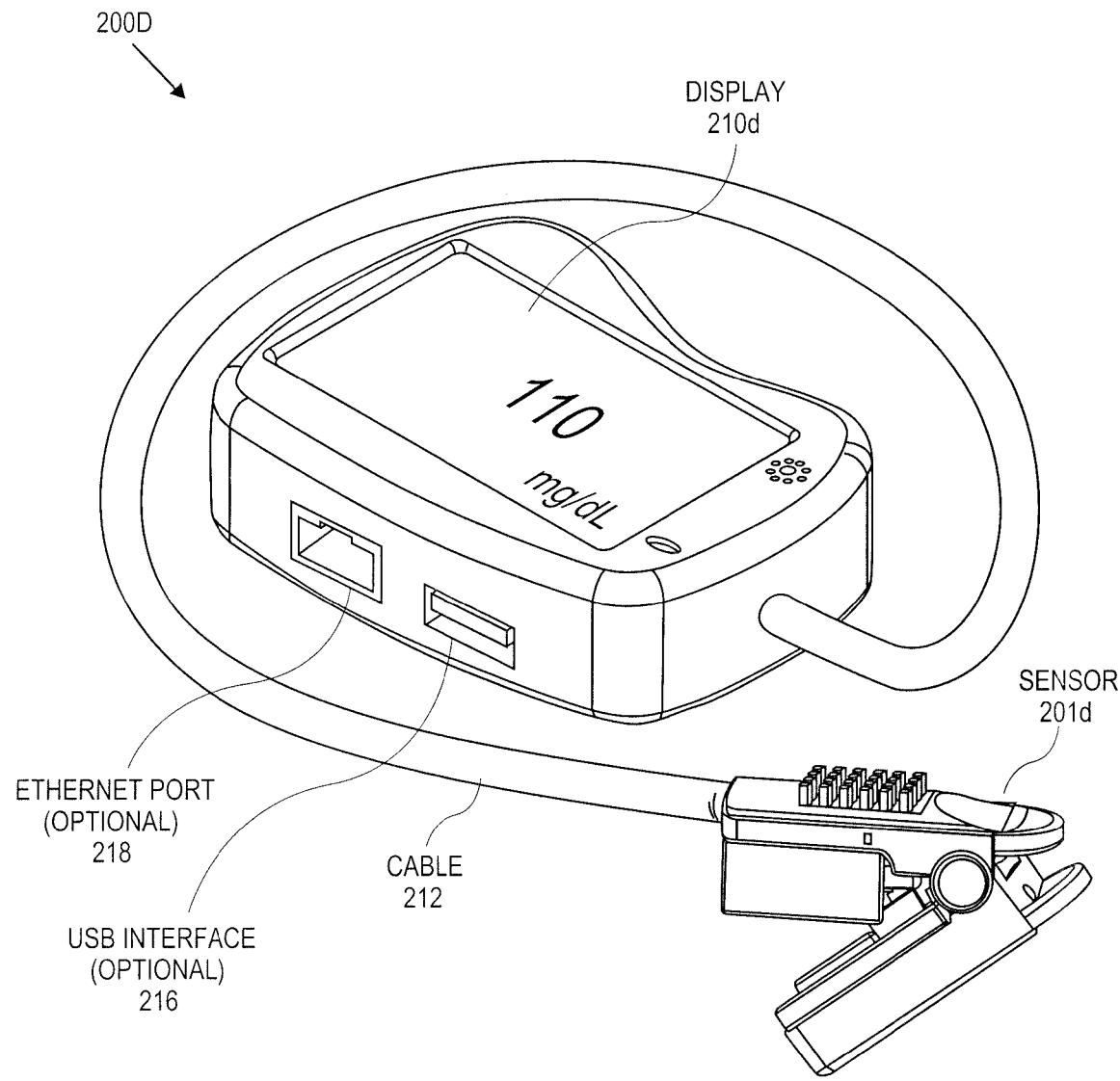

FIG. 2D illustrates yet another example of monitoring device 200D that can house the data collection system 100.

Like the monitoring devices 200B and 200C, the monitoring device 200D includes a finger clip sensor 201d connected to a monitor 209d via a cable 212. The cable 212 can have all of the features described above with respect to FIG. 2B. In addition to having some or all of the features described above with respect to FIGS. 2B and 2C, the monitoring device 200D includes an optional universal serial bus (USB) port 216 and an Ethernet port 218. The USB port 216 and the Ethernet port 218 can be used, for example, to transfer information between the monitor 209d and a computer (not shown) via a cable. Software stored on the computer can provide functionality for a user to, for example, view physiological data and trends, adjust settings and download firmware updates to the monitor 209b, and perform a variety of other functions. The USB port 216 and the Ethernet port 218 can be included with the other monitoring devices 200A, 200B, and 200C described above.

Figure 3A:
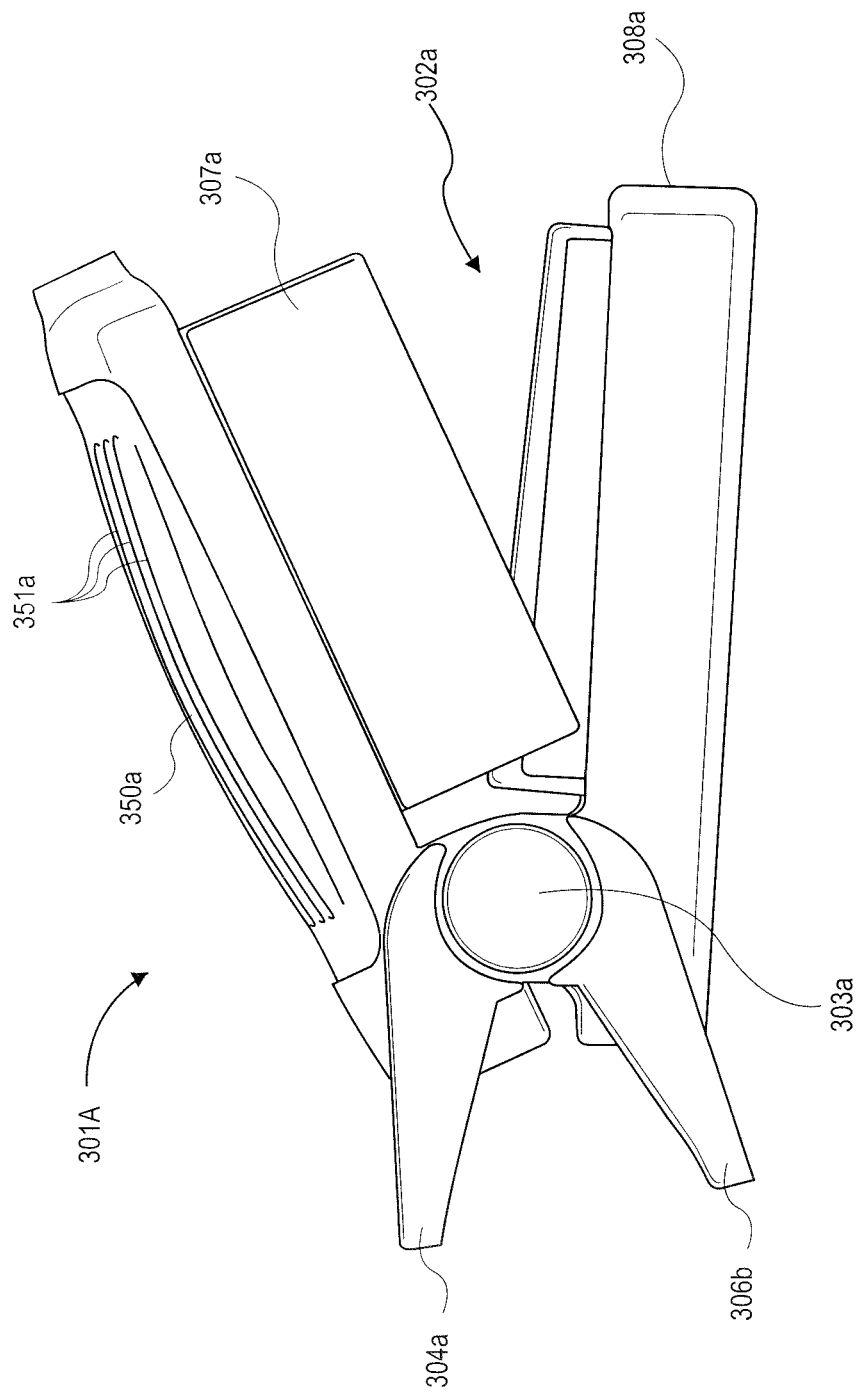
FIGS. 3A-3C illustrate side and perspective views of an exemplary noninvasive sensor housing including a finger bed protrusion and heat sink, according to an embodiment of the disclosure.
Figure 3B:
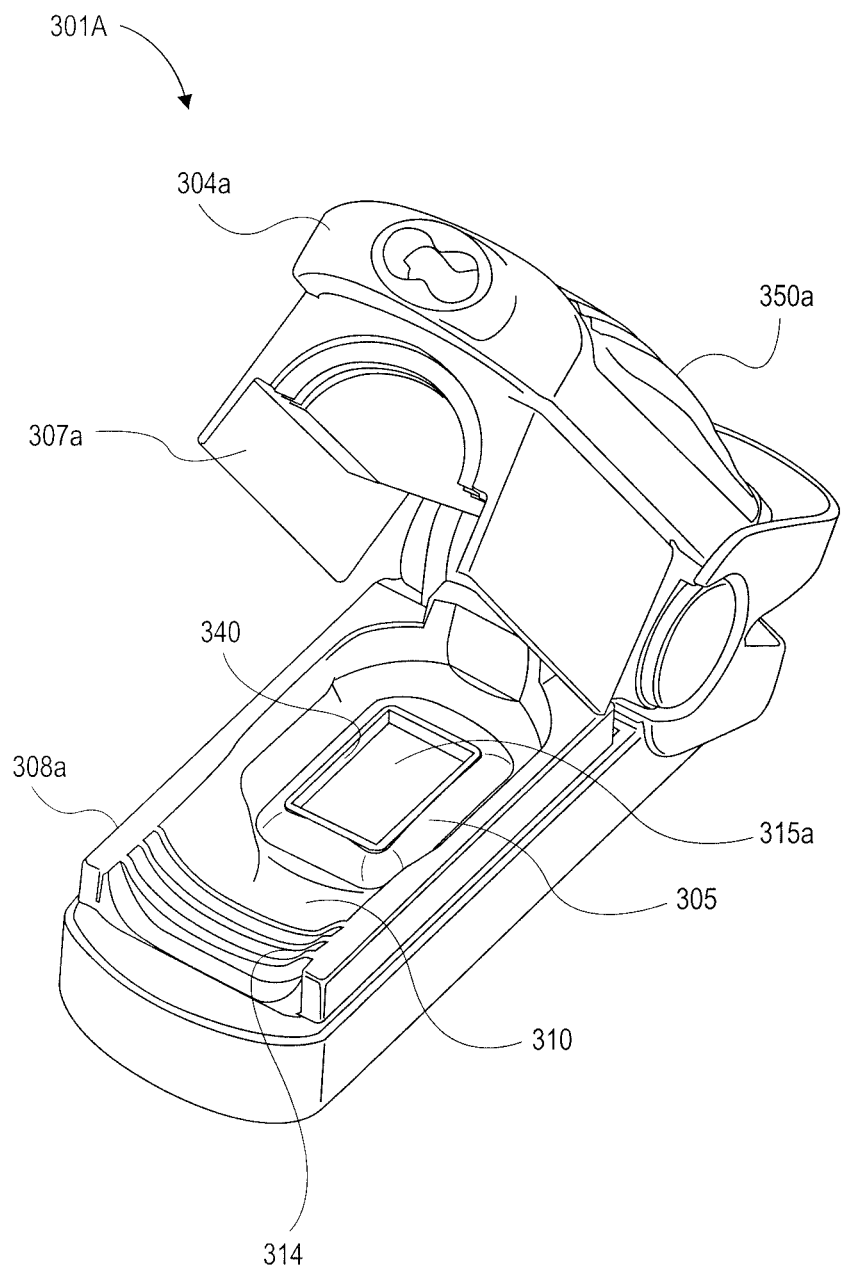
Figure 3C:
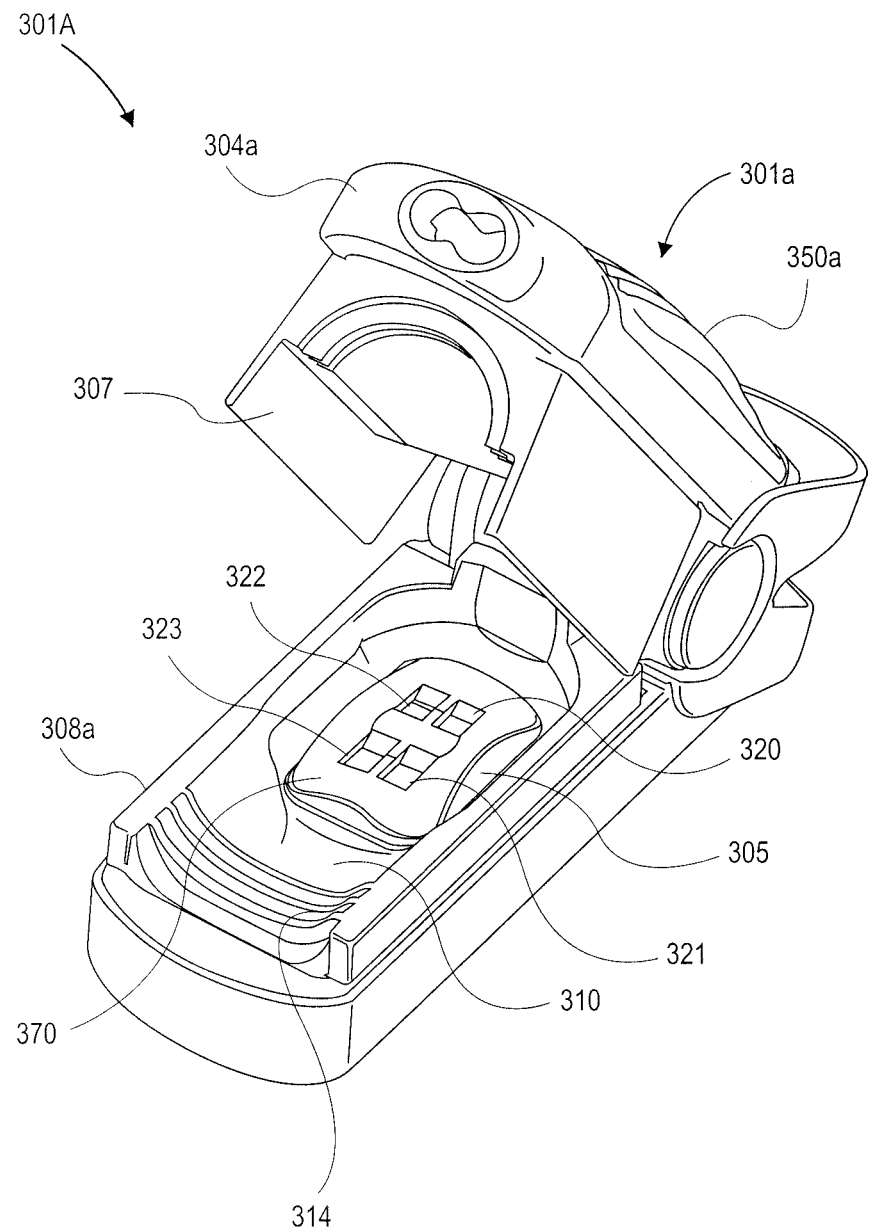

FIGS. 3A through 3C illustrate more detailed examples of embodiments of a sensor 301a. The sensor 301a shown can include all of the features of the sensors 100 and 200 described above.

Referring to FIG. 3A, the sensor 301a in the depicted embodiment is a clothespin-shaped clip sensor that includes an enclosure 302a for receiving a patient's finger. The enclosure 302a is formed by an upper section or emitter shell 304a, which is pivotably connected with a lower section or detector shell 306a. The emitter shell 304a can be biased with the detector shell 306a to close together around a pivot point 303a and thereby sandwich finger tissue between the emitter and detector shells 304a, 306a.

In an embodiment, the pivot point 303a advantageously includes a pivot capable of adjusting the relationship between the emitter and detector shells 304a, 306a to effectively level the sections when applied to a tissue site. In another embodiment, the sensor 301a includes some or all features of the finger clip described in U.S. Publication No. 2006/0211924, incorporated above, such as a spring that causes finger clip forces to be distributed along the finger. Paragraphs [0096] through [0105], which describe this feature, are hereby specifically incorporated by reference.

The emitter shell 304a can position and house various emitter components of the sensor 301a. It can be constructed of reflective material (e.g., white silicone or plastic) and/or can be metallic or include metalicized plastic (e.g., including carbon and aluminum) to possibly serve as a heat sink. The emitter shell 304a can also include absorbing opaque material, such as, for example, black or grey colored material, at various areas, such as on one or more flaps 307a, to reduce ambient light entering the sensor 301a.

The detector shell 306a can position and house one or more detector portions of the sensor 301a. The detector shell 306a can be constructed of reflective material, such as white silicone or plastic. As noted, such materials can increase the usable signal at a detector by forcing light back into the tissue and measurement site (see FIG. 1). The detector shell 306a can also include absorbing opaque material at various areas, such as lower area 308a, to reduce ambient light entering the sensor 301a.

Referring to FIGS. 3B and 3C, an example of finger bed 310 is shown in the sensor 301b. The finger bed 310 includes a generally curved surface shaped generally to receive tissue, such as a human digit. The finger bed 310 includes one or more ridges or channels 314. Each of the ridges 314 has a generally convex shape that can facilitate increasing traction or gripping of the patients finger to the finger bed. Advantageously, the ridges 314 can improve the accuracy of spectroscopic analysis in certain embodiments by reducing noise that can result from a measurement site moving or shaking loose inside of the sensor 301a. The ridges 314 can be made from reflective or opaque materials in some embodiments to further increase SNR. In other implementations, other surface shapes can be used, such as, for example, generally flat, concave, or convex finger beds 310.

Finger bed 310 can also include an embodiment of a tissue thickness adjuster or protrusion 305. The protrusion 305 includes a measurement site contact area 370 (see FIG. 3C) that can contact body tissue of a measurement site. The protrusion 305 can be removed from or integrated with the finger bed 310. Interchangeable, different shaped protrusions 305 can also be provided, which can correspond to different finger shapes, characteristics, opacity, sizes, or the like.

Referring specifically to FIG. 3C, the contact area 370 of the protrusion 305 can include openings or windows 320, 321, 322, and 323. When light from a measurement site passes through the windows 320, 321, 322, and 323, the light can reach one or more photodetectors (see FIG. 3E). In an embodiment, the windows 320, 321, 322, and 323 mirror specific detector placements layouts such that light can impinge through the protrusion 305 onto the photodetectors. Any number of windows 320, 321, 322, and 323 can be employed in the protrusion 305 to allow light to pass from the measurement site to the photodetectors.

The windows 320, 321, 322, and 323 can also include shielding, such as an embedded grid of wiring or a conductive glass coating, to reduce noise from ambient light or other electromagnetic noise. The windows 320, 321, 322, and 323 can be made from materials, such as plastic or glass. In some embodiments, the windows 320, 321, 322, and 323 can be constructed from conductive glass, such as indium tin oxide (ITO) coated glass. Conductive glass can be useful because its shielding is transparent, and thus allows for a larger aperture versus a window with an embedded grid of wiring. In addition, in certain embodiments, the conductive glass does not need openings in its shielding (since it is transparent), which enhances its shielding performance. For example, some embodiments that employ the conductive glass can attain up to an about 40% to about 50% greater signal than non-conductive glass with a shielding grid. In addition, in some embodiments, conductive glass can be useful for shielding noise from a greater variety of directions than non-conductive glass with a shielding grid.

Turning to FIG. 3B, the sensor 301a can also include a shielding 315a, such as a metal cage, box, metal sheet, perforated metal sheet, a metal layer on a non-metal material, or the like. The shielding 315a is provided in the depicted embodiment below or embedded within the protrusion 305 to reduce noise. The shielding 315a can be constructed from a conductive material, such as copper. The shielding 315a can include one or more openings or windows (not shown). The windows can be made from glass or plastic to thereby allow light that has passed through the windows 320, 321, 322, and 323 on an external surface of the protrusion 305 (see FIG. 3C) to pass through to one or more photodetectors that can be enclosed or provided below (see FIG. 3E).

Figure 3D:
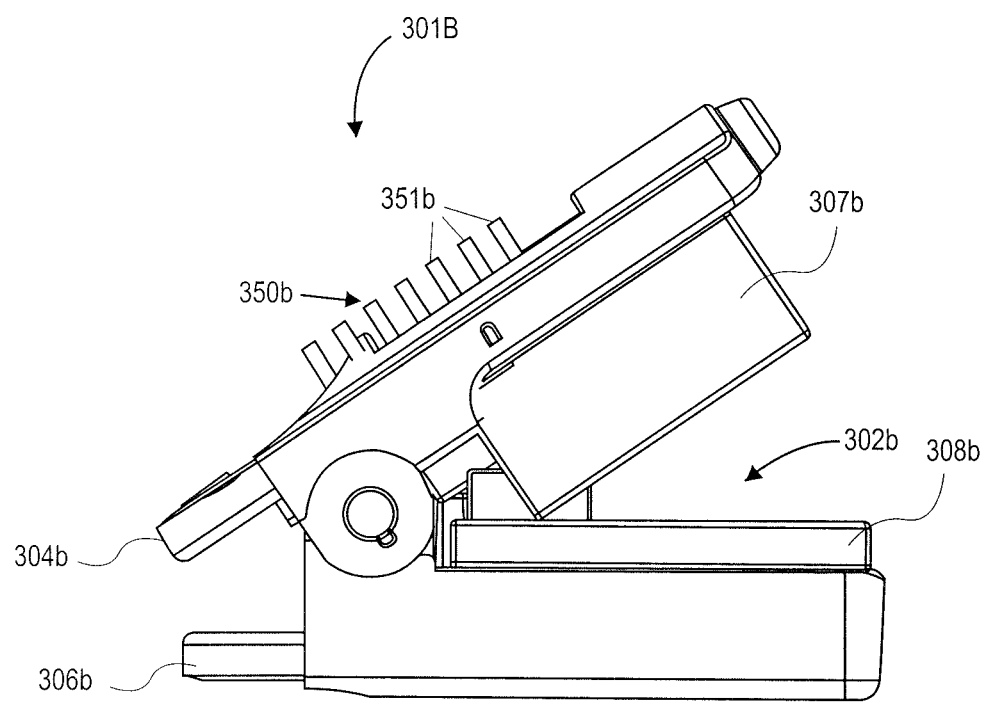
FIG. 3D illustrates a side view of another example noninvasive sensor housing including a heat sink, according to an embodiment of the disclosure.
Figure 3E:
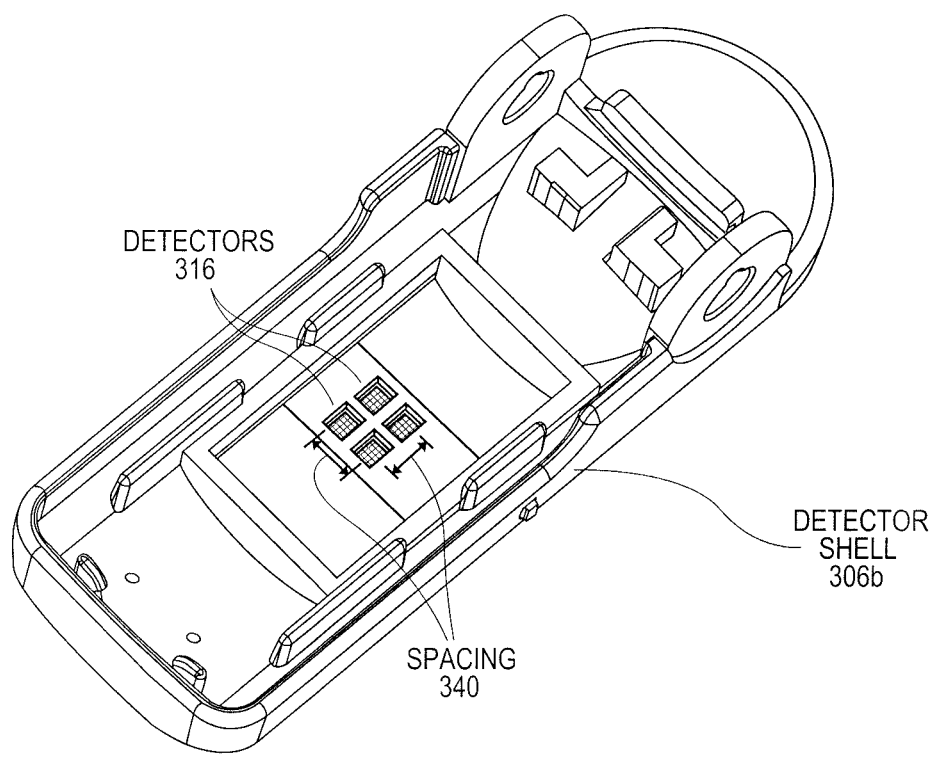
FIG. 3E illustrates a perspective view of an example noninvasive sensor detector shell including example detectors, according to an embodiment of the disclosure.

In an embodiment, the photodetectors can be positioned within or directly beneath the protrusion 305 (see FIG. 3E). In such cases, the mean optical path length from the emitters to the detectors can be reduced and the accuracy of blood analyte measurement can increase. For example, in one embodiment, a convex bump of about 1 mm to about 3 mm in height and about 10 mm$^2$ to about 60 mm$^2$ was found to help signal strength by about an order of magnitude versus other shapes. Of course other dimensions and sizes can be employed in other embodiments. Depending on the properties desired, the length, width, and height of the protrusion 305 can be selected. In making such determinations, consideration can be made of protrusion's 305 effect on blood flow at the measurement site and mean path length for optical radiation passing through openings 320, 321, 322, and 323. Patient comfort can also be considered in determining the size and shape of the protrusion.

In an embodiment, the protrusion 305 can include a pliant material, including soft plastic or rubber, which can somewhat conform to the shape of a measurement site. Pliant materials can improve patient comfort and tactility by conforming the measurement site contact area 370 to the measurement site. Additionally, pliant materials can minimize or reduce noise, such as ambient light. Alternatively, the protrusion 305 can be made from a rigid material, such as hard plastic or metal.

Rigid materials can improve measurement accuracy of a blood analyte by conforming the measurement site to the contact area 370. The contact area 370 can be an ideal shape for improving accuracy or reducing noise. Selecting a material for the protrusion 305 can include consideration of materials that do not significantly alter blood flow at the measurement site. The protrusion 305 and the contact area 370 can include a combination of materials with various characteristics.

The contact area 370 serves as a contact surface for the measurement site. For example, in some embodiments, the contact area 370 can be shaped for contact with a patient's finger. Accordingly, the contact area 370 can be sized and shaped for different sizes of fingers. The contact area 370 can be constructed of different materials for reflective purposes as well as for the comfort of the patient. For example, the contact area 370 can be constructed from materials having various hardness and textures, such as plastic, gel, foam, and the like.

Figure 5:
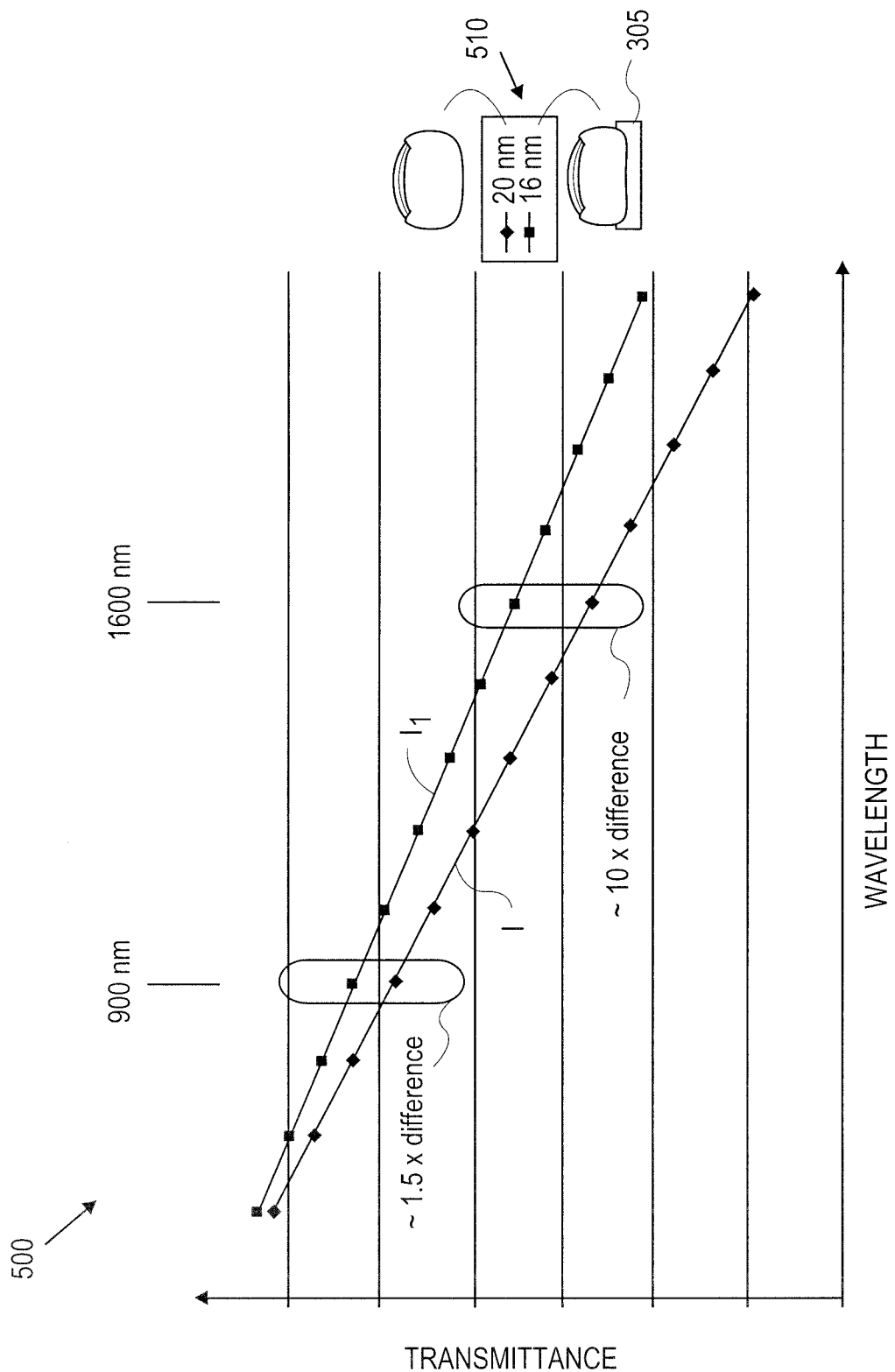
FIG. 5 illustrates an example graph depicting possible effects of a protrusion on light transmittance, according to an embodiment of the disclosure.

The formulas and analysis that follow with respect to FIG. 5 provide insight into how selecting these variables can alter transmittance and intensity gain of optical radiation that has been applied to the measurement site. These examples do not limit the scope of this disclosure.

Referring to FIG. 5, a plot 500 is shown that illustrates examples of effects of embodiments of the protrusion 305 on the SNR at various wavelengths of light. As described above, the protrusion 305 can assist in conforming the tissue and effectively reduce its mean path length. In some instances, this effect by the protrusion 305 can have significant impact on increasing the SNR.

According to the Beer Lambert law, a transmittance of light (l) can be expressed as follows: $l = l_o * e^{-m*b*c}$, where $l_o$ is the initial power of light being transmitted, m is the path length traveled by the light, and the component "b*c" corresponds to the bulk absorption of the light at a specific wavelength of light. For light at about 1600 nm to about 1700 nm, for example, the bulk absorption component is generally around 0.7 mm$^{-1}$. Assuming a typical finger thickness of about 12 mm and a mean path length of 20 mm due to tissue scattering, then $l = l_o * e^{(-20*0.7)}$.

In an embodiment where the protrusion 305 is a convex bump, the thickness of the finger can be reduced to 10 mm (from 12 mm) for some fingers and the effective light mean path is reduced to about 16.6 mm from 20 mm (see box 510). This results in a new transmittance, $l_1 = l_o * e^{(-16.6*0.7)}$. A curve for a typical finger (having a mean path length of 20 mm) across various wavelengths is shown in the plot 500 of FIG. 5. The plot 500 illustrates potential effects of the protrusion 305 on the transmittance. As illustrated, comparing l and $l_1$ results in an intensity gain of $e^{(-16.6*0.7)}/e^{(-20*0.7)}$, which is about a 10 times increase for light in the about 1600 nm to about 1700 nm range. Such an increase can affect the SNR at which the sensor can operate. The foregoing gains can be due at least in part to the about 1600 nm to about 1700 nm range having high values in bulk absorptions (water, protein, and the like), e.g., about 0.7 mm$^{-1}$. The plot 500 also shows improvements in the visible/near-infrared range (about 600 nm to about 1300 nm).

The contribution of a the protrusion 305 to increased SNR cannot have been previously recognized by persons having ordinary skill in the art at least in part because currently available devices can have been concerned primarily with conforming to the measurement site for patient comfort. In addition, for light in the visible range and infrared range, or in other words, at the wavelengths of many previous devices, the bulk absorption of light component in the finger is generally much lower at around 0.1 mm$^{-1}$. Therefore, the same change in thickness increases intensity by, for example, $e^{(-16.6*0.1)}/e^{(-20*0.1)}$, which results in about a 1.5 times increase. In currently available devices, such an impact cannot have been significant enough to warrant overriding other considerations, such as patient comfort. It should be noted, however, that the various protrusion 305 designs disclosed herein can increase SNR while also preserving patient comfort.

Turning again to FIGS. 3A through 3C, an example heat sink 350a is also shown. The heat sink 350a can be attached to, or protrude from an outer surface of, the sensor 301a, thereby providing increased ability for various sensor components to dissipate excess heat. By being on the outer surface of the sensor 301a in certain embodiments, the heat sink 350a can be exposed to the air and thereby facilitate more efficient cooling. In an embodiment, one or more of the emitters (see FIG. 1) generate sufficient heat that inclusion of the heat sink 350a can advantageously allows the sensor 301a to remain safely cooled. The heat sink 350a can include one or more materials that help dissipate heat, such as, for example, aluminum, steel, copper, carbon, combinations of the same, or the like. For example, in some embodiments, the emitter shell 304a can include a heat conducting material that is also readily and relatively inexpensively moldable into desired shapes and forms.

In some embodiments, the heat sink 350a includes metalicized plastic. The metalicized plastic can include aluminum and carbon, for example. The material can allow for improved thermal conductivity and diffusivity, which can increase commercial viability of the heat sink. In some embodiments, the material selected to construct the heat sink 350a can include a thermally conductive liquid crystalline polymer, such as CoolPoly® D5506, commercially available from Cool Polymers®, Inc. of Warwick, R.I. Such a material can be selected for its electrically non-conductive and dielectric properties so as, for example, to aid in electrical shielding. In an embodiment, the heat sink 350a provides improved heat transfer properties when the sensor 301a is active for short intervals of less than a full day's use. In an embodiment, the heat sink 350a can advantageously provide improved heat transfers in about three (3) to about four (4) minute intervals, for example, although a heat sink 350a can be selected that performs effectively in shorter or longer intervals.

Moreover, the heat sink 350a can have different shapes and configurations for aesthetic as well as for functional purposes. In an embodiment, the heat sink is configured to maximize heat dissipation, for example, by maximizing surface area. In an embodiment, the heat sink 350a is molded into a generally curved surface and includes one or more fins, undulations, grooves, or channels. The example heat sink 350a shown includes fins 351a (see FIG. 3A).

An alternative shape of a sensor 301b and heat sink 350b is shown in FIG. 3D. The sensor 301b can include some or all of the features of the sensor 301a. For example, the sensor 301b includes an enclosure 302b formed by an emitter shell 304b and a detector shell 306b, pivotably connected about a pivot 303a. The emitter shell 304b can also include absorbing opaque material on one or more flaps 307b, and the detector shell 306a can also include absorbing opaque material at various areas, such as lower area 308b.

However, the shape of the sensor 301b is different in this embodiment. In particular, the heat sink 350b includes comb protrusions 351b. The comb protrusions 351b are exposed to the air in a similar manner to the fins 351a of the heat sink 350a, thereby facilitating efficient cooling of the sensor 301b.

FIG. 3E illustrates a more detailed example of a detector shell 306b of the sensor 301b. The features described with respect to the detector shell 306b can also be used with the detector shell 306a of the sensor 301a.

As shown, the detector shell 306b includes detectors 316. The detectors 316 can have a predetermined spacing 340 from each other, or a spatial relationship among one another that results in a spatial configuration. This spatial configuration can purposefully create a variation of path lengths among detectors 316 and the emitter discussed above.

In the depicted embodiment, the detector shell 316 can hold multiple (e.g., two, three, four, etc.) photodiode arrays that are arranged in a two-dimensional grid pattern. Multiple photodiode arrays can also be useful to detect light piping (e.g., light that bypasses measurement site 102). In the detector shell 316, walls can be provided to separate the individual photodiode arrays to prevent or reduce mixing of light signals from distinct quadrants. In addition, the detector shell 316 can be covered by windows of transparent material, such as glass, plastic, or the like, to allow maximum or increased transmission of power light captured. In various embodiments, the transparent materials used can also be partially transparent or translucent or can otherwise pass some or all of the optical radiation passing through them. As noted, this window can include some shielding in the form of an embedded grid of wiring, or a conductive layer or coating.

As further illustrated by FIG. 3E, the detectors 316 can have a spatial configuration of a grid. However, the detectors 316 can be arranged in other configurations that vary the path length. For example, the detectors 316 can be arranged in a linear array, a logarithmic array, a two-dimensional array, or the like. Furthermore, any number of the detectors 316 can be employed in certain embodiments.

Figure 3F:
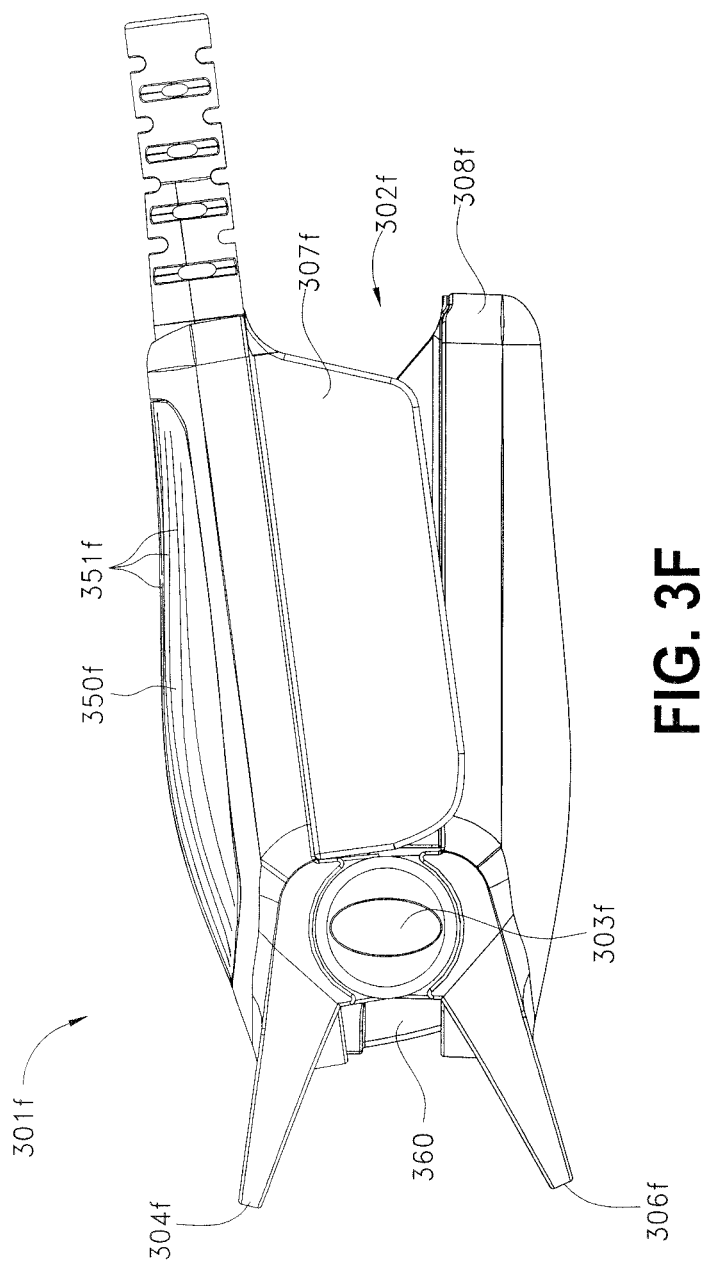
FIG. 3F illustrates a side view of an example noninvasive sensor housing including a finger bed protrusion and heat sink, according to an embodiment of the disclosure.

FIG. 3F illustrates another embodiment of a sensor 301f. The sensor 301f can include some or all of the features of the sensor 301a of FIG. 3A described above. For example, the sensor 301f includes an enclosure 302f formed by an upper section or emitter shell 304f, which is pivotably connected with a lower section or detector shell 306f around a pivot point 303f. The emitter shell 304f can also include absorbing opaque material on various areas, such as on one or more flaps 307f, to reduce ambient light entering the sensor 301f. The detector shell 306f can also include absorbing opaque material at various areas, such as a lower area 308f. The sensor 301f also includes a heat sink 350f, which includes fins 351f.

In addition to these features, the sensor 301f includes a flex circuit cover 360, which can be made of plastic or another suitable material. The flex circuit cover 360 can cover and thereby protect a flex circuit (not shown) that extends from the emitter shell 304f to the detector shell 306f. An example of such a flex circuit is illustrated in U.S. Publication No. 2006/0211924, incorporated above (see FIG. 46 and associated description, which is hereby specifically incorporated by reference). The flex circuit cover 360 is shown in more detail below in FIG. 17.

Figure 4A:
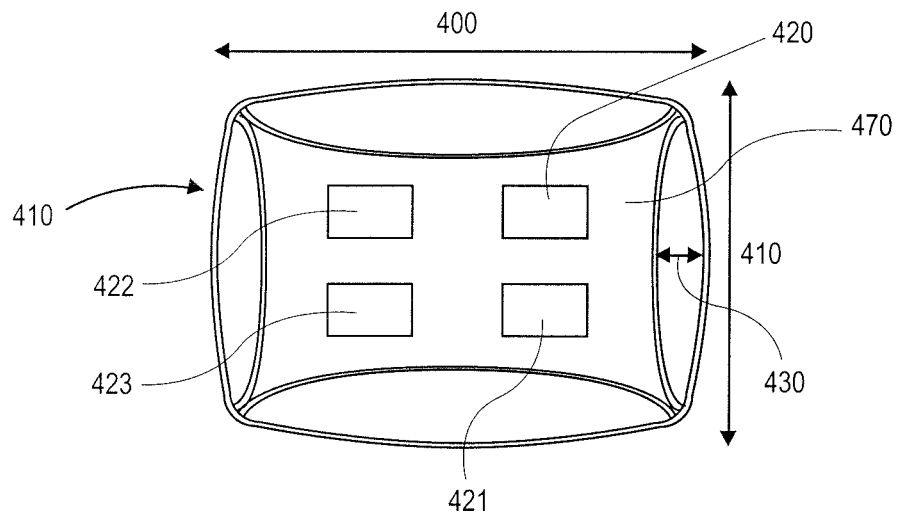
FIGS. 4A through 4C illustrate top elevation, side and top perspective views of an example protrusion, according to an embodiment of the disclosure.
Figure 4B:
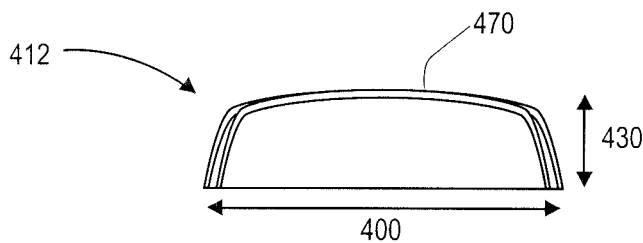
Figure 4C:
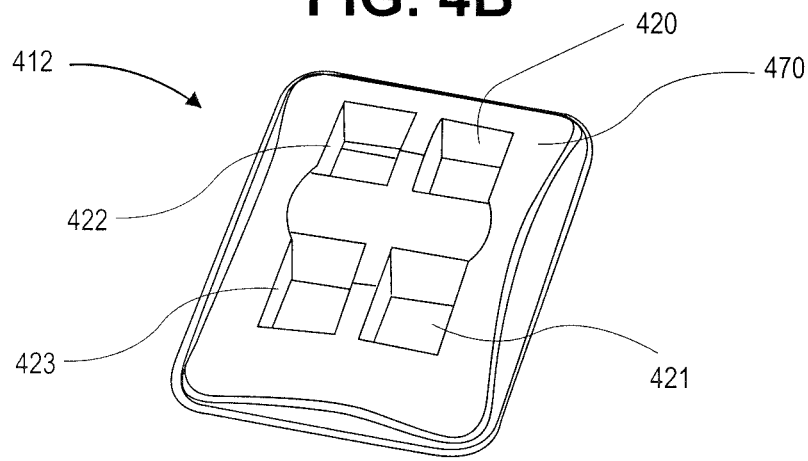

FIGS. 4A through 4C illustrate example arrangements of a protrusion 405, which is an embodiment of the protrusion 305 described above. In an embodiment, the protrusion 405 can include a measurement site contact area 470. The measurement site contact area 470 can include a surface that molds body tissue of a measurement site, such as a finger, into a flat or relatively flat surface.

The protrusion 405 can have dimensions that are suitable for a measurement site such as a patient's finger. As shown, the protrusion 405 can have a length 400, a width 410, and a height 430. The length 400 can be from about 9 to about 11 millimeters, e.g., about 10 millimeters. The width 410 can be from about 7 to about 9 millimeters, e.g., about 8 millimeters. The height 430 can be from about 0.5 millimeters to about 3 millimeters, e.g., about 2 millimeters. In an embodiment, the dimensions 400, 410, and 430 can be selected such that the measurement site contact area 470 includes an area of about 80 square millimeters although larger and smaller areas can be used for different sized tissue for an adult, an adolescent, or infant, or for other considerations.

The measurement site contact area 470 can also include differently shaped surfaces that conform the measurement site into different shapes. For example, the measurement site contact area 470 can be generally curved and/or convex with respect to the measurement site. The measurement site contact area 470 can be other shapes that reduce or even minimize air between the protrusion 405 and or the measurement site. Additionally, the surface pattern of the measurement site contact area 470 can vary from smooth to bumpy, e.g., to provide varying levels of grip.

In FIGS. 4A and 4C, openings or windows 420, 421, 422, and 423 can include a wide variety of shapes and sizes, including for example, generally square, circular, triangular, or combinations thereof. The windows 420, 421, 422, and 423 can be of non-uniform shapes and sizes. As shown, the windows 420, 421, 422, and 423 can be evenly spaced out in a grid like arrangement. Other arrangements or patterns of arranging the windows 420, 421, 422, and 423 are possible. For example, the windows 420, 421, 422, and 423 can be placed in a triangular, circular, or linear arrangement. In some embodiments, the windows 420, 421, 422, and 423 can be placed at different heights with respect to the finger bed 310 of FIG. 3. The windows 420, 421, 422, and 423 can also mimic or approximately mimic a configuration of, or even house, a plurality of detectors.

FIGS. 6A through 6D illustrate another embodiment of a protrusion 605 that can be used as the tissue shaper 105 described above or in place of the protrusions 305, 405 described above. The depicted protrusion 605 is a partially cylindrical lens having a partial cylinder 608 and an extension 610. The partial cylinder 608 can be a half cylinder in some embodiments; however, a smaller or greater portion than half of a cylinder can be used. Advantageously, in certain embodiments, the partially cylindrical protrusion 605 focuses light onto a smaller area, such that fewer detectors can be used to detect the light attenuated by a measurement site.

Figure 6A:
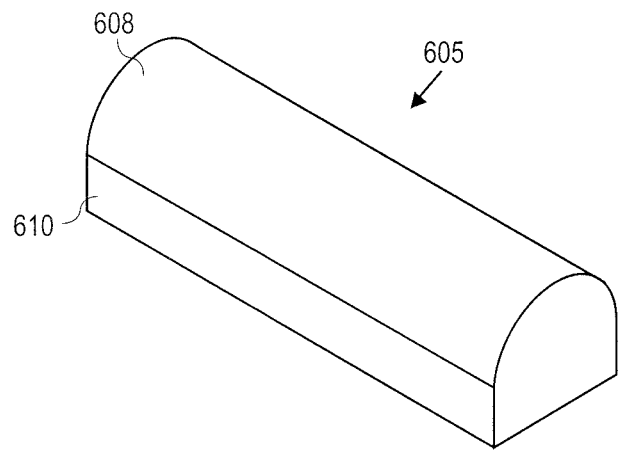
FIGS. 6A through 6D illustrate perspective, front elevation, side and top views of another example protrusion, according to an embodiment of the disclosure.
Figure 6B:
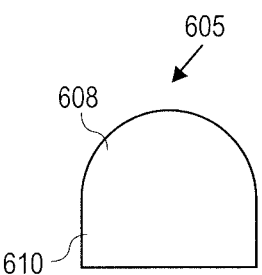
Figure 6C:
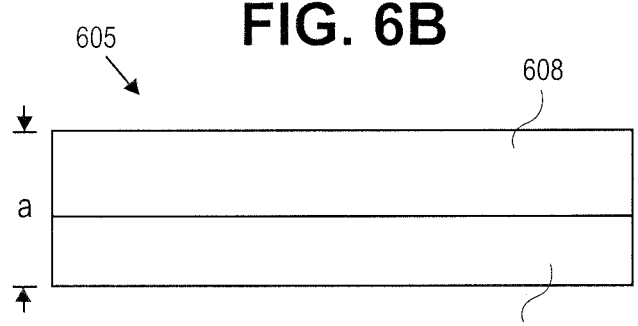
Figure 6D:
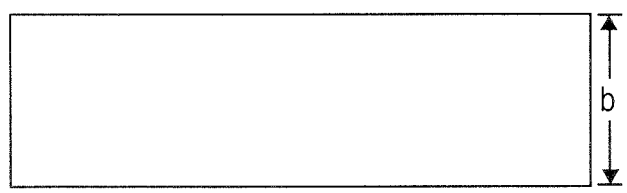

FIG. 6A illustrates a perspective view of the partially cylindrical protrusion 605. FIG. 6B illustrates a front elevation view of the partially cylindrical protrusion 605. FIG. 6C illustrates a side view of the partially cylindrical protrusion 605. FIG. 6D illustrates a top view of the partially cylindrical protrusion 605.

Advantageously, in certain embodiments, placing the partially cylindrical protrusion 605 over the photodiodes in any of the sensors described above adds multiple benefits to any of the sensors described above. In one embodiment, the partially cylindrical protrusion 605 penetrates into the tissue and reduces the pathlength of the light traveling in the tissue, similar to the protrusions described above.

The partially cylindrical protrusion 605 can also collect light from a large surface and focus down the light to a smaller area. As a result, in certain embodiments, signal strength per area of the photodiode can be increased. The partially cylindrical protrusion 605 can therefore facilitate a lower cost sensor because, in certain embodiments, less photodiode area can be used to obtain the same signal strength. Less photodiode area can be realized by using smaller photodiodes or fewer photodiodes (see, e.g., FIG. 14). If fewer or smaller photodiodes are used, the partially cylindrical protrusion 605 can also facilitate an improved SNR of the sensor because fewer or smaller photodiodes can have less dark current.

The dimensions of the partially cylindrical protrusion 605 can vary based on, for instance, a number of photodiodes used with the sensor. Referring to FIG. 6C, the overall height of the partially cylindrical protrusion 605 (measurement "a") in some implementations is about 1 to about 3 mm. A height in this range can allow the partially cylindrical protrusion 605 to penetrate into the pad of the finger or other tissue and reduce the distance that light travels through the tissue. Other heights, however, of the partially cylindrical protrusion 605 can also accomplish this objective. For example, the chosen height of the partially cylindrical protrusion 605 can be selected based on the size of the measurement site, whether the patient is an adult or child, and so on. In an embodiment, the height of the protrusion 605 is chosen to provide as much tissue thickness reduction as possible while reducing or preventing occlusion of blood vessels in the tissue.

Referring to FIG. 6D, the width of the partially cylindrical protrusion 605 (measurement "b") can be about 3 to about 5 mm. In one embodiment, the width is about 4 mm. In one embodiment, a width in this range provides good penetration of the partially cylindrical protrusion 605 into the tissue to reduce the pathlength of the light. Other widths, however, of the partially cylindrical protrusion 605 can also accomplish this objective. For example, the width of the partially cylindrical protrusion 605 can vary based on the size of the measurement site, whether the patient is an adult or child, and so on. In addition, the length of the protrusion 605 could be about 10 mm, or about 8 mm to about 12 mm, or smaller than 8 mm or greater than 12 mm.

In certain embodiments, the focal length (f) for the partially cylindrical protrusion 605 can be expressed as:

$$f = \frac{R}{n-1},$$

where R is the radius of curvature of the partial cylinder 608 and n is the index of refraction of the material used. In certain embodiments, the radius of curvature can be between about 1.5 mm and about 2 mm. In another embodiment, the partially cylindrical protrusion 605 can include a material, such as nBK7 glass, with an index of refraction of around 1.5 at 1300 nm, which can provide focal lengths of between about 3 mm and about 4 mm.

A partially cylindrical protrusion 605 having a material with a higher index of refraction such as nSF11 glass (e.g., n=1.75 at 1300 nm) can provide a shorter focal length and possibly a smaller photodiode chip, but can also cause higher reflections due to the index of refraction mismatch with air. Many types of glass or plastic can be used with index of refraction values ranging from, for example, about 1.4 to about 1.9. The index of refraction of the material of the protrusion 605 can be chosen to improve or optimize the light focusing properties of the protrusion 605. A plastic partially cylindrical protrusion 605 could provide the cheapest option in high volumes but can also have some undesired light absorption peaks at wavelengths higher than 1500 nm. Other focal lengths and materials having different indices of refraction can be used for the partially cylindrical protrusion 605.

Placing a photodiode at a given distance below the partially cylindrical protrusion 605 can facilitate capturing some or all of the light traveling perpendicular to the lens within the active area of the photodiode (see FIG. 14). Different sizes of the partially cylindrical protrusion 605 can use different sizes of photodiodes. The extension 610 added onto the bottom of the partial cylinder 608 is used in certain embodiments to increase the height of the partially cylindrical protrusion 605. In an embodiment, the added height is such that the photodiodes are at or are approximately at the focal length of the partially cylindrical protrusion 605. In an embodiments, the added height provides for greater thinning of the measurement site. In an embodiment, the added height assists in deflecting light piped through the sensor. This is because light piped around the sensor passes through the side walls of the added height without being directed toward the detectors. The extension 610 can also further facilitate the protrusion 605 increasing or maximizing the amount of light that is provided to the detectors. In some embodiments, the extension 610 can be omitted.

Figure 6E:
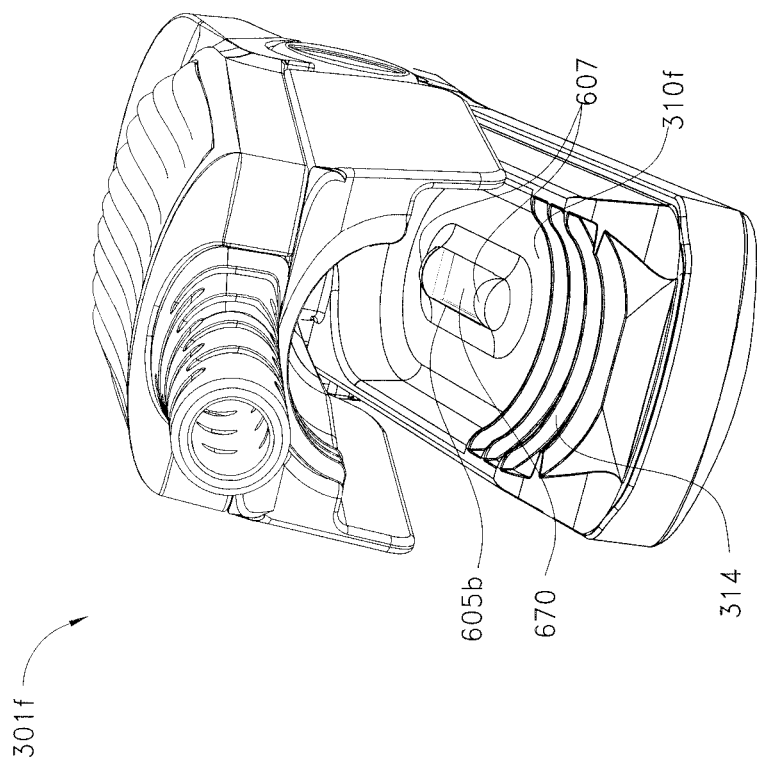
FIG. 6E illustrates an example sensor incorporating the protrusion of FIGS. 6A through 6D, according to an embodiment of the disclosure.

FIG. 6E illustrates another view of the sensor 301f of FIG. 3F, which includes an embodiment of a partially cylindrical protrusion 605b. Like the sensor 301A shown in FIGS. 3B and 3C, the sensor 301f includes a finger bed 310f. The finger bed 310f includes a generally curved surface shaped generally to receive tissue, such as a human digit. The finger bed 310f also includes the ridges or channels 314 described above with respect to FIGS. 3B and 3C.

The example of finger bed 310f shown also includes the protrusion 605b, which includes the features of the protrusion 605 described above. In addition, the protrusion 605b also includes chamfered edges 607 on each end to provide a more comfortable surface for a finger to slide across (see also FIG. 14D). In another embodiment, the protrusion 605b could instead include a single chamfered edge 607 proximal to the ridges 314. In another embodiment, one or both of the chamfered edges 607 could be rounded.

The protrusion 605b also includes a measurement site contact area 670 that can contact body tissue of a measurement site. The protrusion 605b can be removed from or integrated with the finger bed 310f. Interchangeable, differently shaped protrusions 605b can also be provided, which can correspond to different finger shapes, characteristics, opacity, sizes, or the like.

Figure 7A:
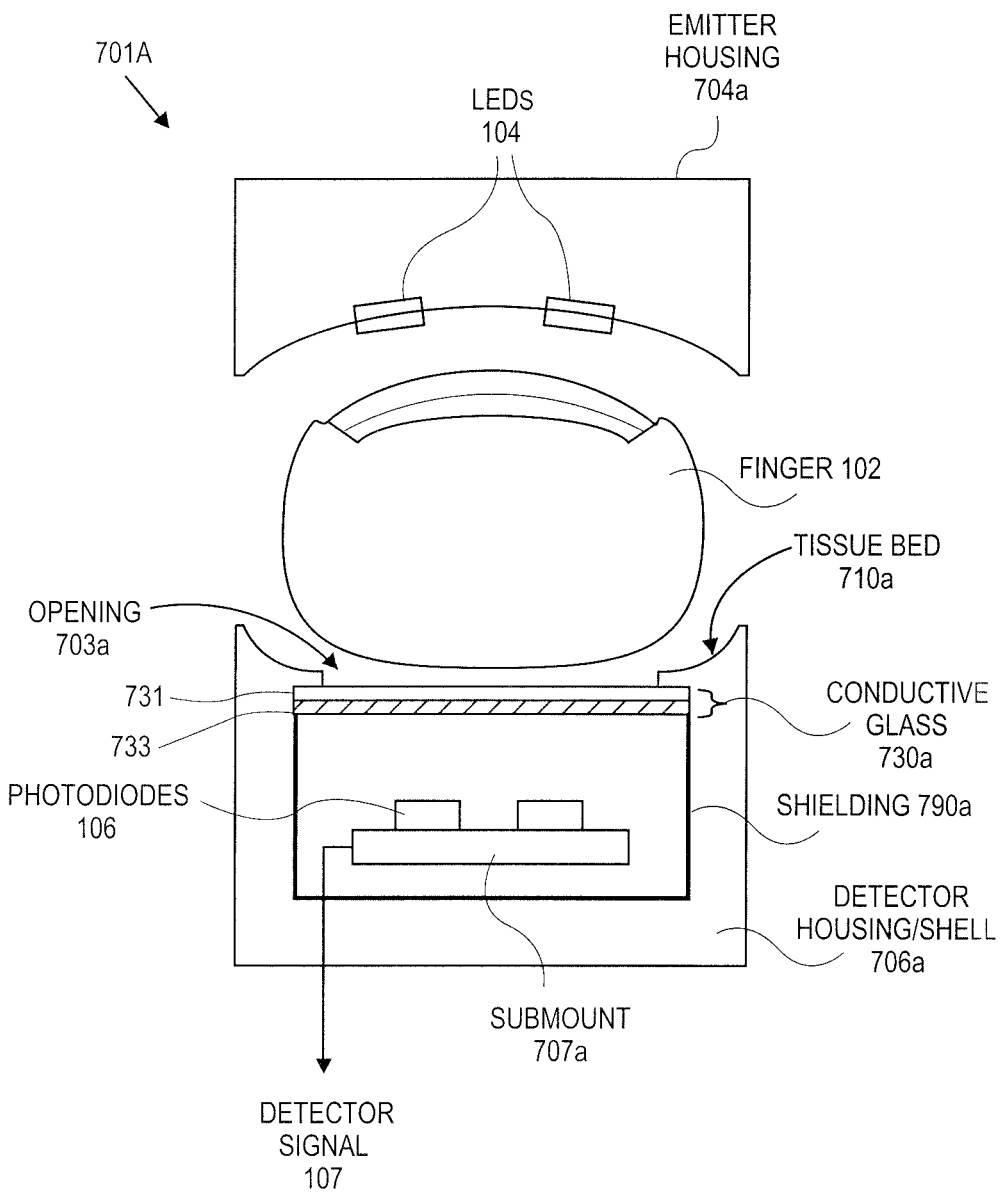
FIGS. 7A through 7B illustrate example arrangements of conductive glass that may be employed in the system of FIG. 1, according to embodiments of the disclosure.
Figure 7B:
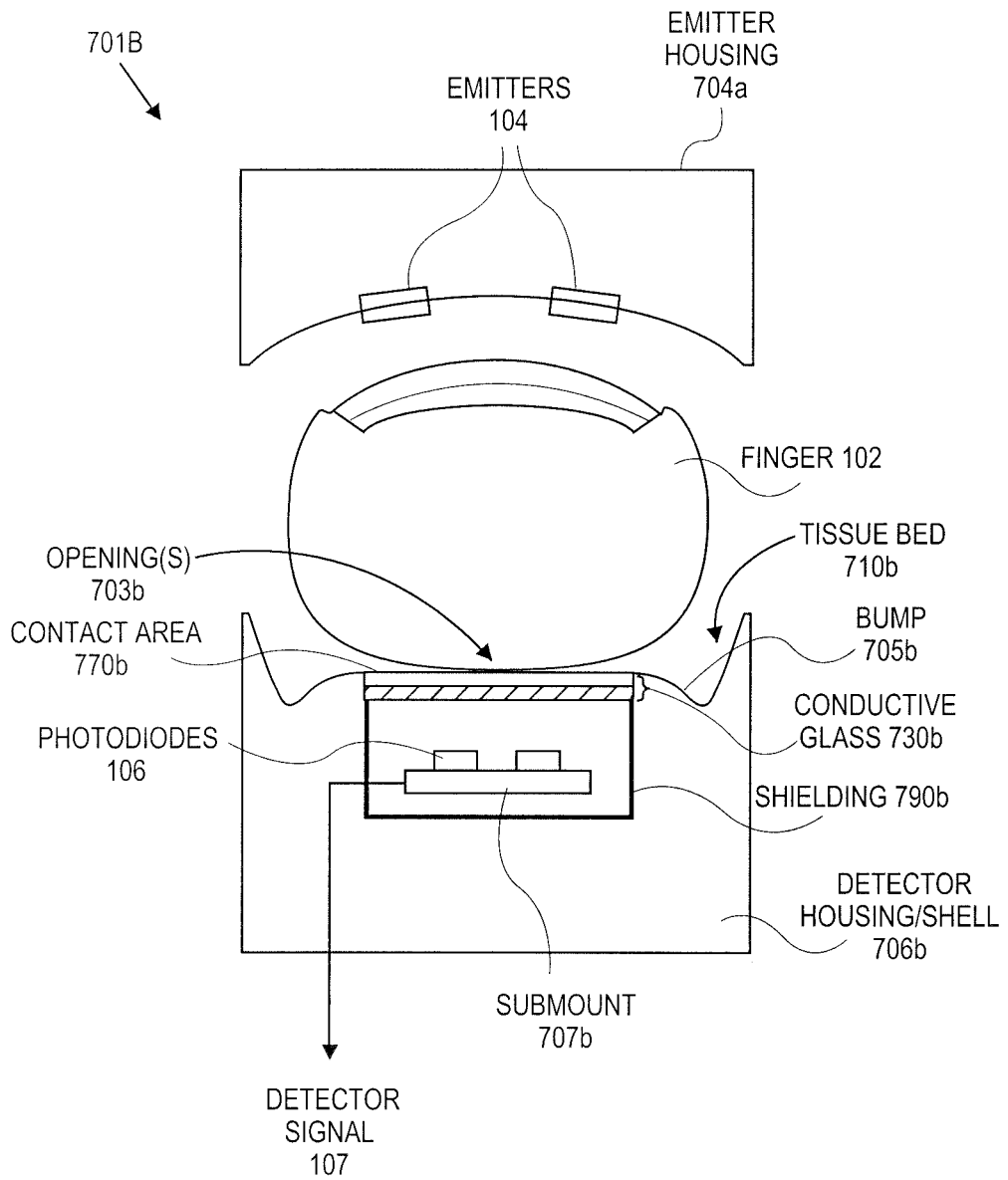

FIGS. 7A and 7B illustrate block diagrams of sensors 701 that include example arrangements of conductive glass or conductive coated glass for shielding. Advantageously, in certain embodiments, the shielding can provide increased SNR. The features of the sensors 701 can be implemented with any of the sensors 101, 201, 301 described above. Although not shown, the partially cylindrical protrusion 605 of FIG. 6 can also be used with the sensors 701 in certain embodiments.

For example, referring specifically to FIG. 7A, the sensor 701a includes an emitter housing 704a and a detector housing 706. The emitter housing 704a includes LEDs 104. The detector housing 706a includes a tissue bed 710a with an opening or window 703a, the conductive glass 730a, and one or more photodiodes for detectors 106 provided on a submount 707a.

During operation, a finger 102 can be placed on the tissue bed 710a and optical radiation can be emitted from the LEDs 104. Light can then be attenuated as it passes through or is reflected from the tissue of the finger 102. The attenuated light can then pass through the opening 703a in the tissue bed 710a. Based on the received light, the detectors 106 can provide a detector signal 107, for example, to the front end interface 108 (see FIG. 1).

In the depicted embodiment, the conductive glass 730 is provided in the opening 703. The conductive glass 730 can thus not only permit light from the finger to pass to the detectors 106, but it can also supplement the shielding of the detectors 106 from noise. The conductive glass 730 can include a stack or set of layers. In FIG. 7A, the conductive glass 730a is shown having a glass layer 731 proximate the finger 102 and a conductive layer 733 electrically coupled to the shielding 790a.

In an embodiment, the conductive glass 730a can be coated with a conductive, transparent or partially transparent material, such as a thin film of indium tin oxide (ITO). To supplement electrical shielding effects of a shielding enclosure 790a, the conductive glass 730a can be electrically coupled to the shielding enclosure 790a. The conductive glass 730a can be electrically coupled to the shielding 704a based on direct contact or via other connection devices, such as a wire or another component.

The shielding enclosure 790a can be provided to encompass the detectors 106 to reduce or prevent noise. For example, the shielding enclosure 790a can be constructed from a conductive material, such as copper, in the form of a metal cage. The shielding or enclosure a can include an opaque material to not only reduce electrical noise, but also ambient optical noise.

Referring to FIG. 7B, another block diagram of an example sensor 701b is shown. A tissue bed 710b of the sensor 701b includes a protrusion 705b, which is in the form of a convex bump. The protrusion 705b can include all of the features of the protrusions or tissue shaping materials described above. For example, the protrusion 705b includes a contact area 370 that comes in contact with the finger 102 and which can include one or more openings 703b. One or more components of conductive glass 730b can be provided in the openings 703. For example, in an embodiment, each of the openings 703 can include a separate window of the conductive glass 730b. In an embodiment, a single piece of the conductive glass 730b can used for some or all of the openings 703b. The conductive glass 730b is smaller than the conductive glass 730a in this particular embodiment.

A shielding enclosure 790b is also provided, which can have all the features of the shielding enclosure 790a. The shielding enclosure 790b is smaller than the shielding enclosure 790a; however, a variety of sizes can be selected for the shielding enclosures 790.

FIGS. 8A through 8D illustrate a perspective view, side views, and a bottom elevation view of the conductive glass described above with respect to the sensors 701a, 701b. As shown in the perspective view of FIG. 8A and side view of FIG. 8B, the conductive glass 730 includes the electrically conductive material 733 described above as a coating on the glass layer 731 described above to form a stack. In an embodiment where the electrically conductive material 733 includes indium tin oxide, surface resistivity of the electrically conductive material 733 can range approximately from 30 ohms per square inch to 500 ohms per square inch, or approximately 30, 200, or 500 ohms per square inch. As would be understood by a person of skill in the art from the present disclosure, other resistivities can also be used which are less than 30 ohms or more than 500 ohms. Other transparent, electrically conductive materials can be used as the material 733.

Although the conductive material 733 is shown spread over the surface of the glass layer 731, the conductive material 733 can be patterned or provided on selected portions of the glass layer 731. Furthermore, the conductive material 733 can have uniform or varying thickness depending on a desired transmission of light, a desired shielding effect, and other considerations.

Figure 8A:
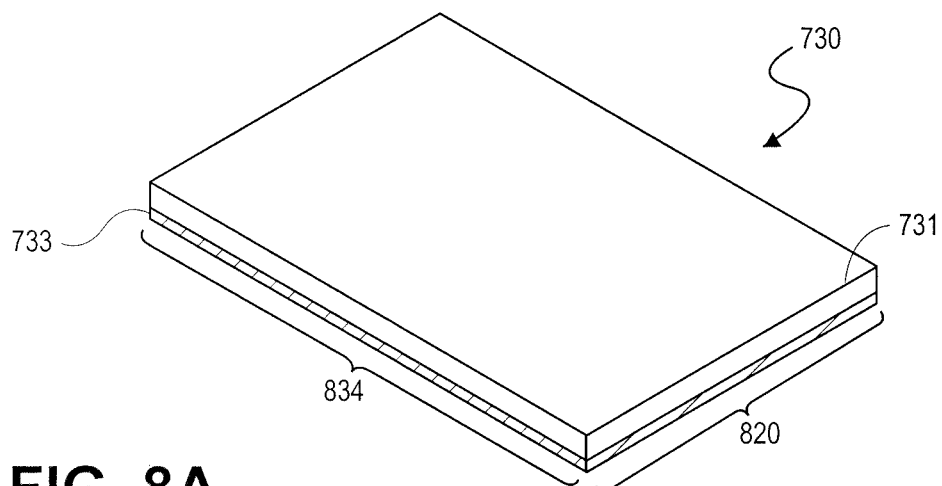
FIGS. 8A through 8D illustrate an example top elevation view, side views, and a bottom elevation view of the conductive glass that may be employed in the system of FIG. 1, according to embodiments of the disclosure.
Figure 8B:
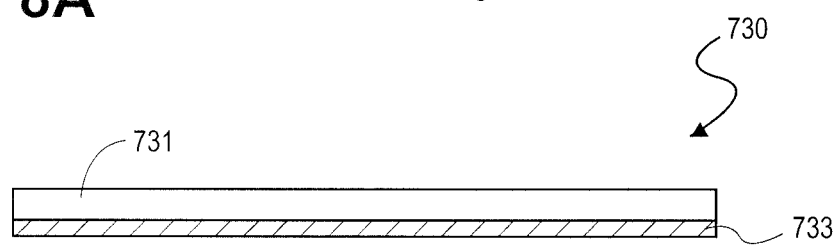
Figure 8C:
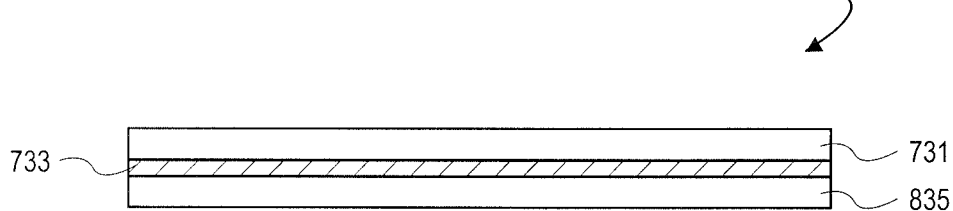

In FIG. 8C, a side view of a conductive glass 830*a* is shown to illustrate an embodiment where the electrically conductive material 733 is provided as an internal layer between two glass layers 731, 835. Various combinations of integrating electrically conductive material 733 with glass are possible. For example, the electrically conductive material 733 can be a layer within a stack of layers. This stack of layers can include one or more layers of glass 731, 835, as well as one or more layers of conductive material 733. The stack can include other layers of materials to achieve desired characteristics.

Figure 8D:
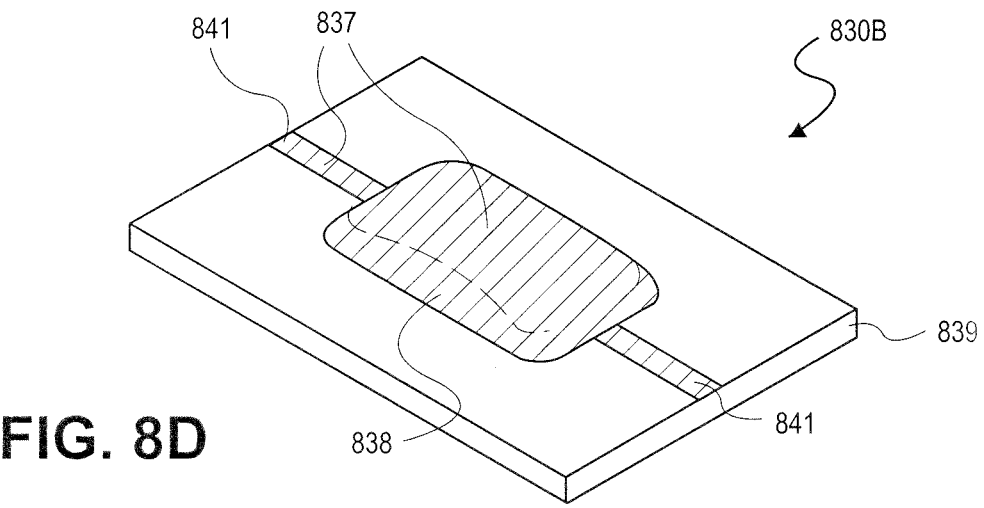

In FIG. 8D, a bottom perspective view is shown to illustrate an embodiment where a conductive glass 830*b* can include conductive material 837 that occupies or covers a portion of a glass layer 839. This embodiment can be useful, for example, to create individual, shielded windows for detectors 106, such as those shown in FIG. 3C. The conductive material 837 can be patterned to include an area 838 to allow light to pass to detectors 106 and one or more strips 841 to couple to the shielding 704 of FIG. 7.

Other configurations and patterns for the conductive material can be used in certain embodiments, such as, for example, a conductive coating lining periphery edges, a conductive coating outlaid in a pattern including a grid or other pattern, a speckled conductive coating, coating outlaid in lines in either direction or diagonally, varied thicknesses from the center out or from the periphery in, or other suitable patterns or coatings that balance the shielding properties with transparency considerations.

Figure 9:
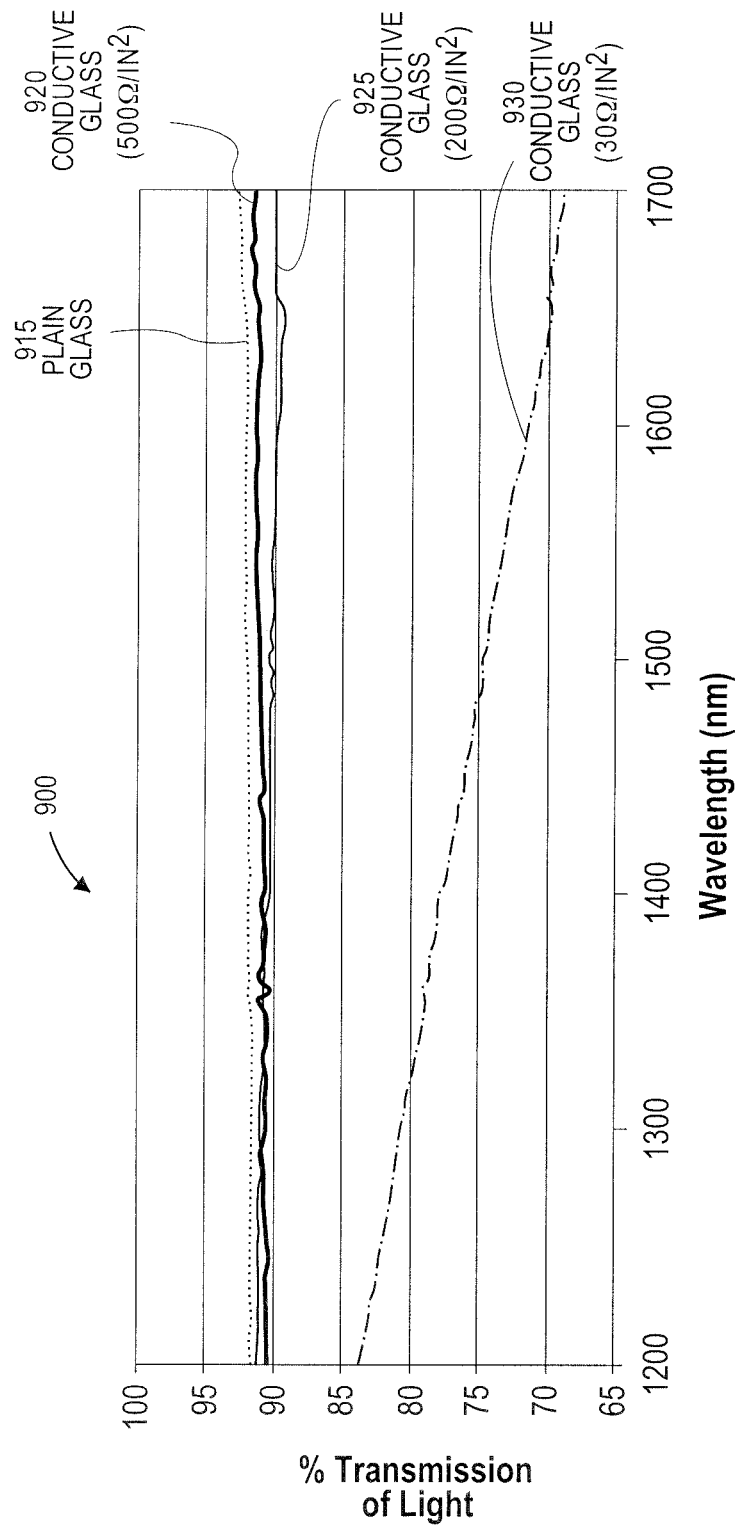
FIG. 9 shows example comparative results obtained by an embodiment of a sensor.

FIG. 9 depicts an example graph 900 that illustrates comparative results obtained by an example sensor having components similar to those disclosed above with respect to FIGS. 7 and 8. The graph 900 depicts the results of the percentage of transmission of varying wavelengths of light for different types of windows used in the sensors described above.

A line 915 on the graph 900 illustrates example light transmission of a window made from plain glass. As shown, the light transmission percentage of varying wavelengths of light is approximately 90% for a window made from plain glass. A line 920 on the graph 900 demonstrates an example light transmission percentage for an embodiment in which a window is made from glass having an ITO coating with a surface resistivity of 500 ohms per square inch. A line 925 on the graph 900 shows an example light transmission for an embodiment in which a window is made from glass that includes a coating of ITO oxide with a surface resistivity of 200 ohms per square inch. A line 930 on the graph 900 shows an example light transmission for an embodiment in which a window is made from glass that includes a coating of ITO oxide with a surface resistivity of 30 ohms per square inch.

The light transmission percentage for a window with currently available embedded wiring can have a light transmission percentage of approximately 70%. This lower percentage of light transmission can be due to the opacity of the wiring employed in a currently available window with wiring. Accordingly, certain embodiments of glass coatings described herein can employ, for example, ITO coatings with different surface resistivity depending on the desired light transmission, wavelengths of light used for measurement, desired shielding effect, and other criteria.

Figure 10A:
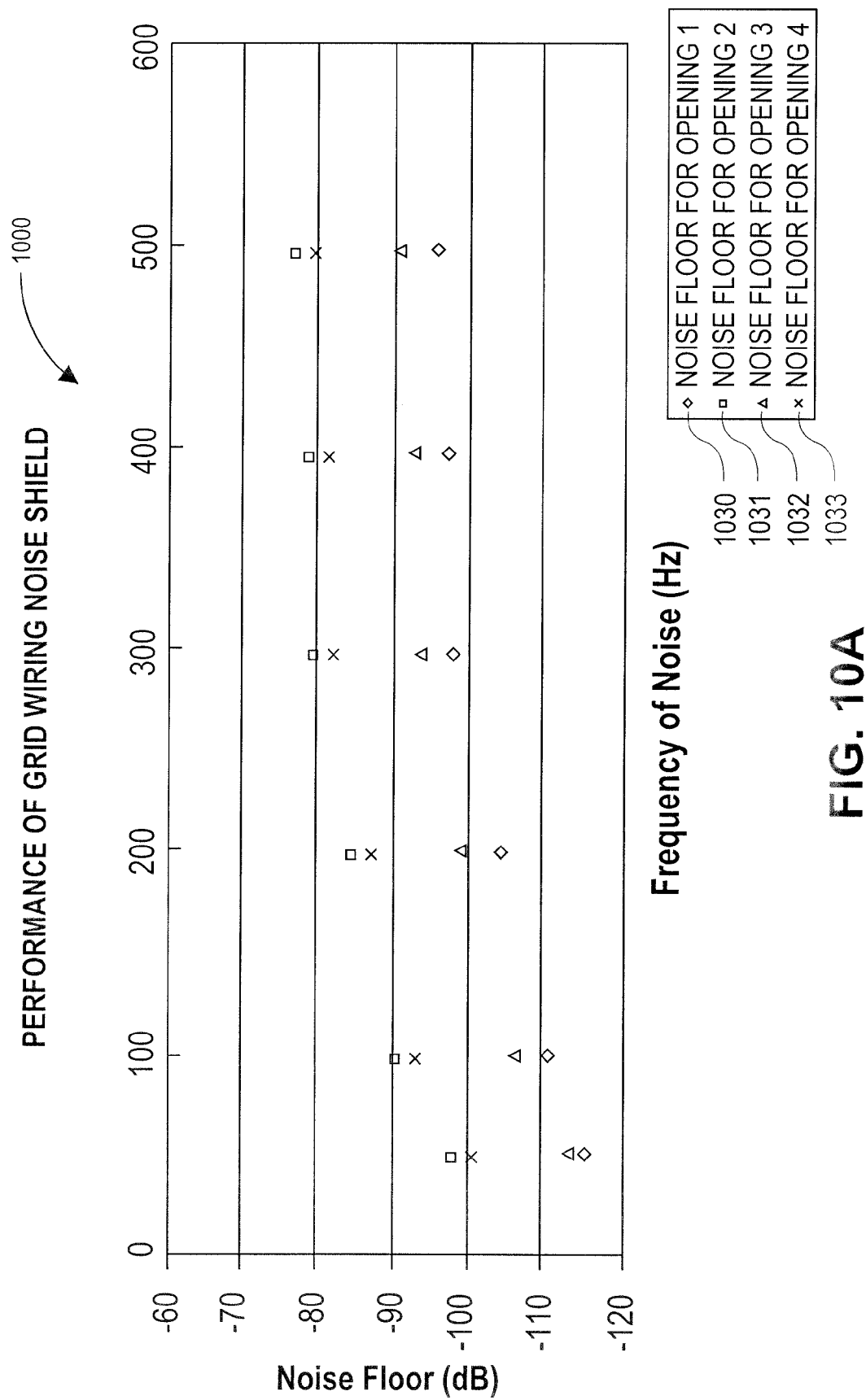
FIGS. 10A and 10B illustrate comparative noise floors of various embodiments of the present disclosure.
Figure 10B:
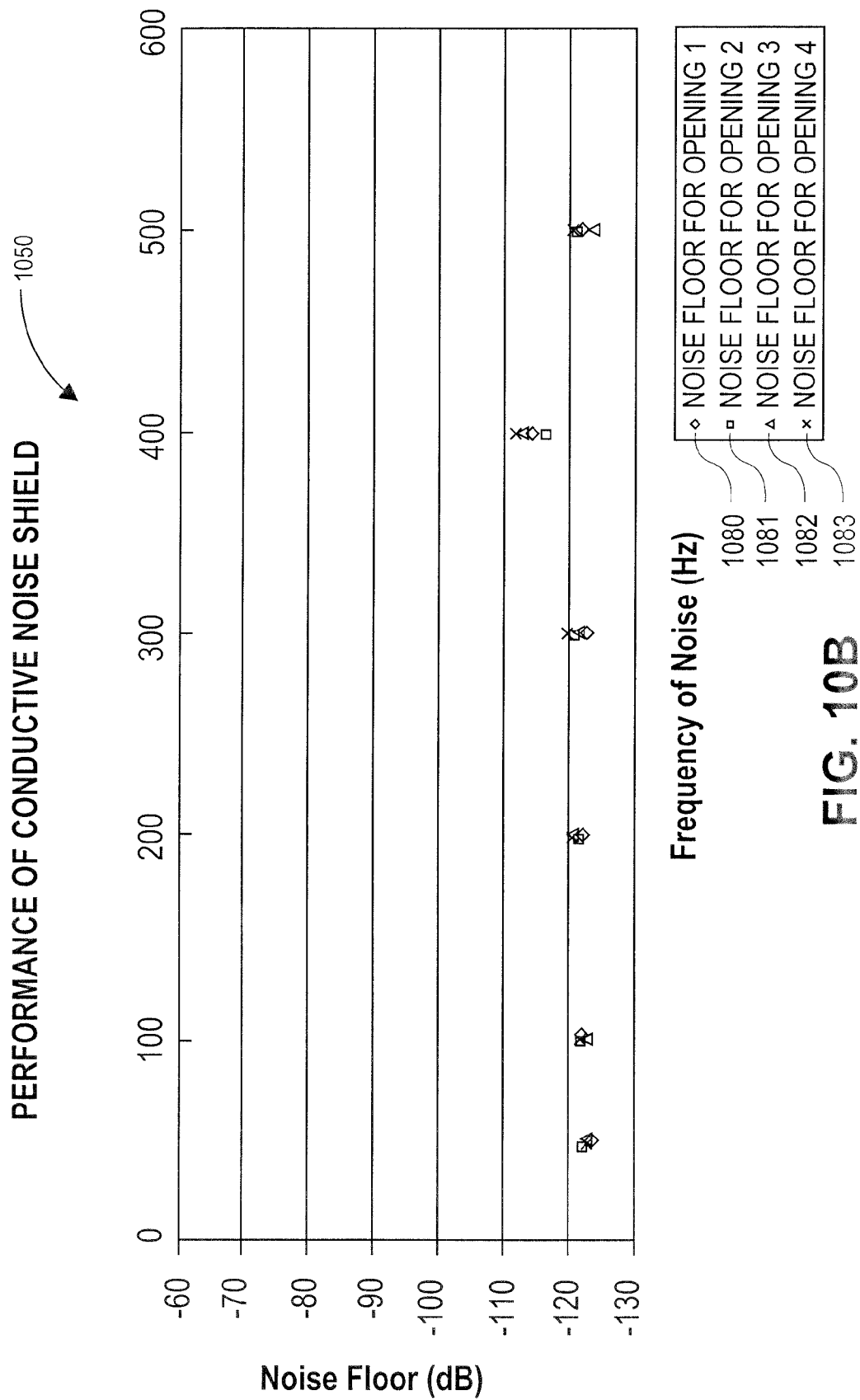

FIGS. 10A through 10B illustrate comparative noise floors of example implementations of the sensors described above. Noise can include optical noise from ambient light and electromagnetic noise, for example, from surrounding electrical equipment. In FIG. 10A, a graph 1000 depicts possible noise floors for different frequencies of noise for an embodiment in which one of the sensors described above included separate windows for four (4) detectors 106. One or more of the windows included an embedded grid of wiring as a noise shield. Symbols 1030-1033 illustrate the noise floor performance for this embodiment. As can be seen, the noise floor performance can vary for each of the openings and based on the frequency of the noise.

In FIG. 10B, a graph 1050 depicts a noise floor for frequencies of noise 1070 for an embodiment in which the sensor included separate openings for four (4) detectors 106 and one or more windows that include an ITO coating. In this embodiment, a surface resistivity of the ITO used was about 500 ohms per square inch. Symbols 1080-1083 illustrate the noise floor performance for this embodiment. As can be seen, the noise floor performance for this embodiment can vary less for each of the openings and provide lower noise floors in comparison to the embodiment of FIG. 10A.

Figure 11:
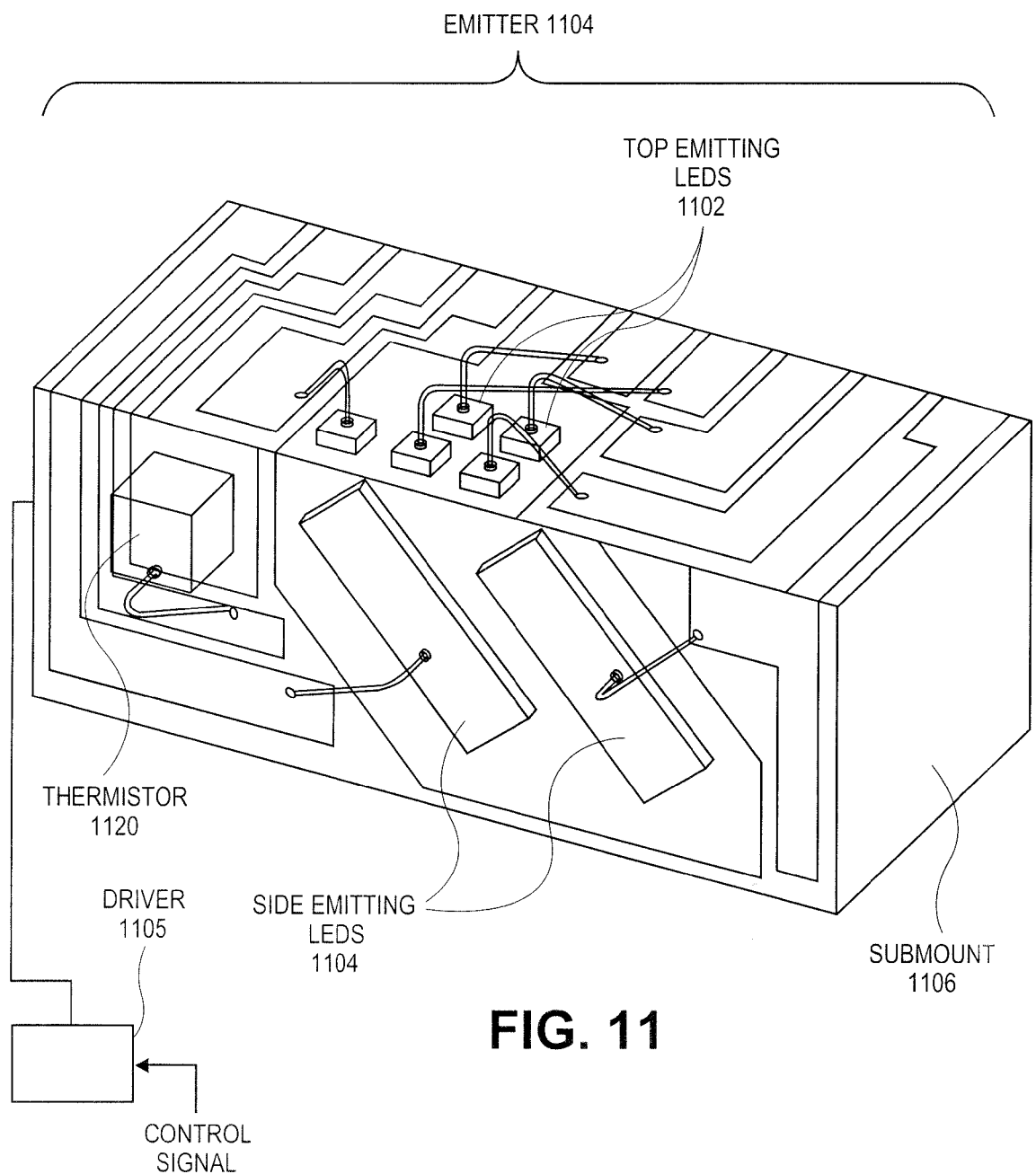
FIG. 11 illustrates a block diagram of some of the components that may include an embodiment of a sensor, according to an embodiment of the disclosure.

FIG. 11 illustrates an example structure for configuring the set of optical sources of the emitters described above. As shown, an emitter 1104 can include a driver 1111, a thermistor 1120, a set of top-emitting LEDs 1102 for emitting red and/or infrared light, a set of side-emitting LEDs 1104 for emitting near infrared light, and a submount 1106.

The thermistor 1120 can be provided to compensate for temperature variations. For example, the thermistor 1120 can be provided to allow for wavelength centroid and power drift of LEDs 1102 and 1104 due to heating. In addition, other thermistors (not shown) can be employed, for example, to measure a temperature of a measurement site. Such a temperature can be helpful in correcting for wavelength drift due to changes in water absorption, which can be temperature dependent, thereby providing more accurate data useful in detecting blood analytes like glucose.

The driver 1105 can provide pulses of current to the emitter 1104. In an embodiment, the driver 1105 drives the emitter 1104 in a progressive fashion for example, in an alternating manner based on a control signal from, for example, a processor (e.g., the processor 110). For example, the driver 1105 can drive the emitter 1104 with a series of pulses to about 1 milliwatt (mW) for visible light to light at about 1300 nm and from about 40 mW to about 100 mW for light at about 1600 nm to about 1700 nm. However, a wide number of driving powers and driving methodologies can be used. The driver 1105 can be synchronized with other parts of the sensor and can minimize or reduce any jitter in the timing of pulses of optical radiation emitted from the emitter 1104. In some embodiments, the driver 1105 is capable of driving the emitter 1104 to emit an optical radiation in a pattern that varies by less than about 10 parts-per-million; however other amounts of variation can be used.

The submount 1106 provides a support structure in certain embodiments for aligning the top-emitting LEDs 1102 and the side-emitting LEDs 1104 so that their optical radiation is transmitted generally towards the measurement site. In some embodiments, the submount 1106 is also constructed of aluminum nitride (AlN) or beryllium oxide (BEO) for heat dissipation, although other materials or combinations of materials suitable for the submount 1106 can be used.

Figure 12:
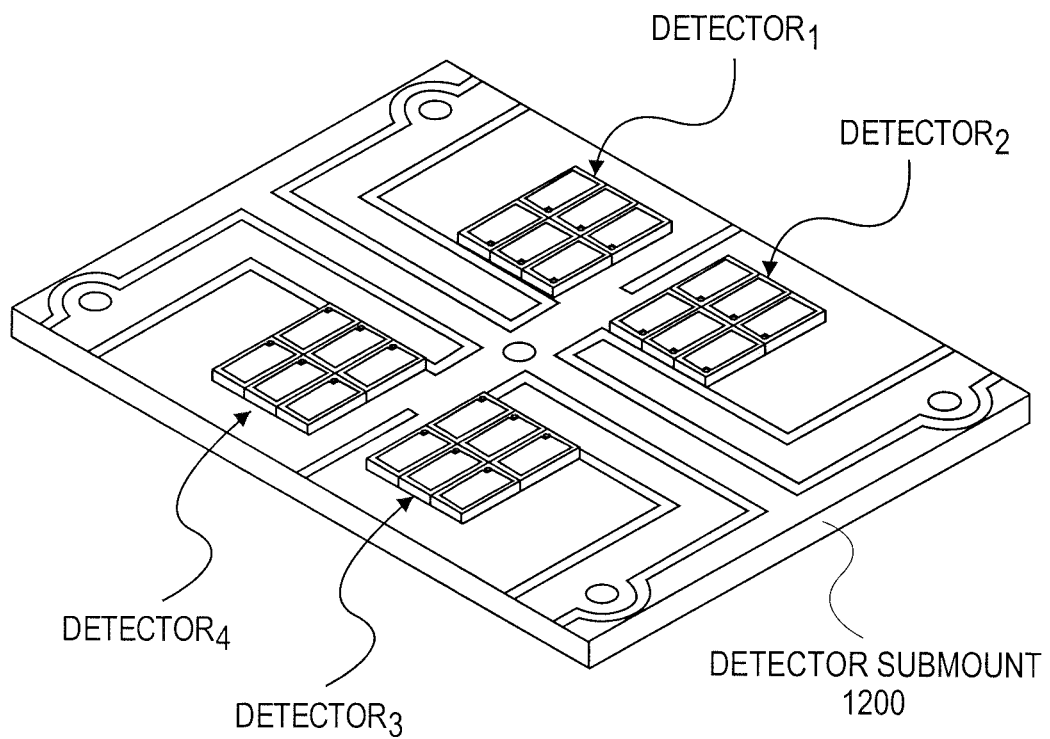
FIG. 12 illustrates an example detector portion that may be employed in an embodiment of a sensor, according to an embodiment of the disclosure.

FIG. 12 illustrates a detector submount 1200 having photodiode detectors that are arranged in a grid pattern on the detector submount 1200 to capture light at different quadrants from a measurement site. One detector submount 1200 can be placed under each window of the sensors described above, or multiple windows can be placed over a single detector submount 1200. The detector submount 1200 can also be used with the partially cylindrical protrusion 605 described above with respect to FIG. 6.

The detectors include photodiode detectors 1-4 that are arranged in a grid pattern on the submount 1200 to capture light at different quadrants from the measurement site. As noted, other patterns of photodiodes, such as a linear row, or logarithmic row, can also be employed in certain embodiments.

Figure 13:
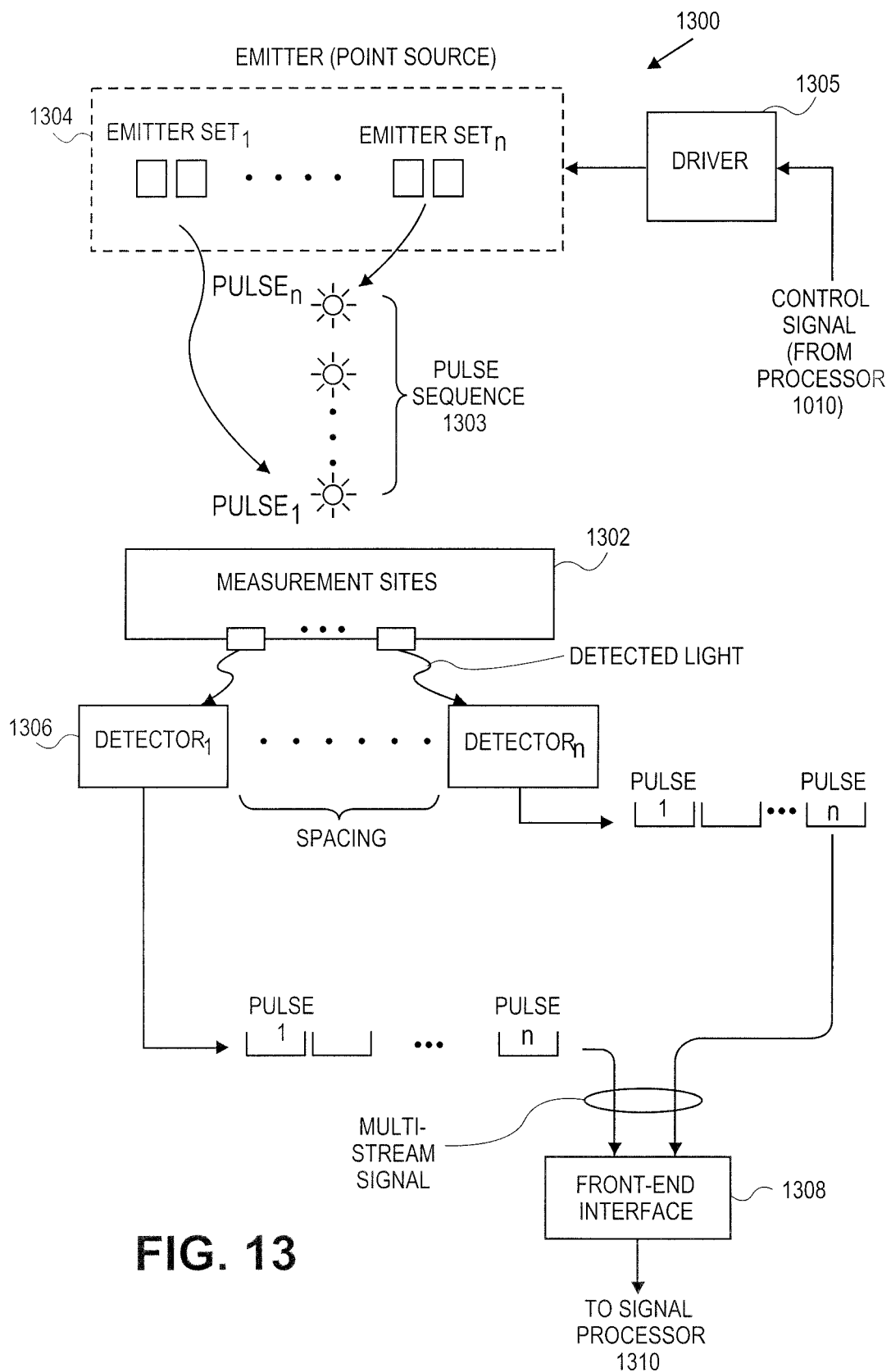
FIG. 13 illustrates an example multi-stream operation of the system of FIG. 1, according to an embodiment of the disclosure.

FIG. 13 illustrates an example multi-stream process 1300. The multi-stream process 1300 can be implemented by the data collection system 100 and/or by any of the sensors described above. As shown, a control signal from a signal processor 1310 controls a driver 1305. In response, an emitter 1304 generates a pulse sequence 1303 from its emitter (e.g., its LEDs) into a measurement site or sites 1302. As described above, in some embodiments, the pulse sequence 1303 is controlled to have a variation of about 10 parts per million or less. Of course, depending on the analyte desired, the tolerated variation in the pulse sequence 1303 can be greater (or smaller).

In response to the pulse sequence 1300, detectors 1 to n (n being an integer) in a detector 1306 capture optical radiation from the measurement site 1302 and provide respective streams of output signals. Each signal from one of detectors 1-n can be considered a stream having respective time slots corresponding to the optical pulses from emitter sets 1-n in the emitter 1304. Although n emitters and n detectors are shown, the number of emitters and detectors need not be the same in certain implementations.

A front end interface 1308 can accept these multiple streams from detectors 1-n and deliver one or more signals or composite signal(s) back to the signal processor 1310. A stream from the detectors 1-n can thus include measured light intensities corresponding to the light pulses emitted from the emitter 1304.

The signal processor 1310 can then perform various calculations to measure the amount of glucose and other analytes based on these multiple streams of signals. In order to help explain how the signal processor 1310 can measure analytes like glucose, a primer on the spectroscopy employed in these embodiments will now be provided.

Spectroscopy is premised upon the Beer-Lambert law. According to this law, the properties of a material, e.g., glucose present in a measurement site can be deterministically calculated from the absorption of light traveling through the material. Specifically, there is a logarithmic relation between the transmission of light through a material and the concentration of a substance and also between the transmission and the length of the path traveled by the light. As noted, this relation is known as the Beer-Lambert law.

The Beer-Lambert law is usually written as:

Absorbance $A = m \ast b \ast c$, where:

m is the wavelength-dependent molar absorptivity coefficient (usually expressed in units of $M^{-1}\, cm^{-1}$);

b is the mean path length; and c is the analyte concentration (e.g., the desired parameter).

In spectroscopy, instruments attempt to obtain the analyte concentration (c) by relating absorbance (A) to transmittance (T). Transmittance is a proportional value defined as:

$T = l/l_o$, where:

l is the light intensity measured by the instrument from the measurement site; and $l_o$ is the initial light intensity from the emitter.

Absorbance (A) can be equated to the transmittance (T) by the equation:

$A = -\log T$

Therefore, substituting equations from above:

$A = -\log(l/l_o)$

In view of this relationship, spectroscopy thus relies on a proportional-based calculation of $-\log(l/l_o)$ and solving for analyte concentration (c).

Typically, in order to simplify the calculations, spectroscopy will use detectors that are at the same location in order to keep the path length (b) a fixed, known constant. In addition, spectroscopy will employ various mechanisms to definitively know the transmission power ($l_o$), such as a photodiode located at the light source. This architecture can be viewed as a single channel or single stream sensor, because the detectors are at a single location.

However, this scheme can encounter several difficulties in measuring analytes, such as glucose. This can be due to the high overlap of absorption of light by water at the wavelengths relevant to glucose as well as other factors, such as high self-noise of the components.

Embodiments of the present disclosure can employ a different approach that in part allows for the measurement of analytes like glucose. Some embodiments can employ a bulk, non-pulsatile measurement in order to confirm or validate a pulsatile measurement. In addition, both the non-pulsatile and pulsatile measurements can employ, among other things, the multi-stream operation described above in order to attain sufficient SNR. In particular, a single light source having multiple emitters can be used to transmit light to multiple detectors having a spatial configuration.

A single light source having multiple emitters can allow for a range of wavelengths of light to be used. For example, visible, infrared, and near infrared wavelengths can be employed. Varying powers of light intensity for different wavelengths can also be employed.

Secondly, the use of multiple-detectors in a spatial configuration allow for a bulk measurement to confirm or validate that the sensor is positioned correctly. This is because the multiple locations of the spatial configuration can provide, for example, topology information that indicates where the sensor has been positioned. Currently available sensors do not provide such information. For example, if the bulk measurement is within a predetermined range of values, then this can indicate that the sensor is positioned correctly in order to perform pulsatile measurements for analytes like glucose. If the bulk measurement is outside of a certain range or is an unexpected value, then this can indicate that the sensor should be adjusted, or that the pulsatile measurements can be processed differently to compensate, such as using a different calibration curve or adjusting a calibration curve. This feature and others allow the embodiments to achieve noise cancellation and noise reduction, which can be several times greater in magnitude that what is achievable by currently available technology.

In order to help illustrate aspects of the multi-stream measurement approach, the following example derivation is provided. Transmittance (T) can be expressed as:

$$T = e^{-m*b*c}$$

In terms of light intensity, this equation can also be rewritten as:

$$I/I_o = e^{-m*b*c}$$

Or, at a detector, the measured light (l) can be expressed as:

$$l = l_o * e^{-m*b*c}$$

As noted, in the present disclosure, multiple detectors (1 to n) can be employed, which results in $l_1 \ldots l_n$ streams of measurements. Assuming each of these detectors have their own path lengths, $b_1 \ldots b_n$, from the light source, the measured light intensities can be expressed as:

$$l_n = l_o * e^{-m*b_n*c}$$

The measured light intensities at any two different detectors can be referenced to each other. For example:

$$l_1/l_n = (l_o * e^{-mb_1 c})/(l_o * e^{-mb_n c})$$

As can be seen, the terms, $l_o$, cancel out and, based on exponent algebra, the equation can be rewritten as:

$$l_1/l_n = e^{-m(b_1 - b_n)c}$$

From this equation, the analyte concentration (c) can now be derived from bulk signals $l_1 \ldots l_n$ and knowing the respective mean path lengths $b_1$ and $b_n$. This scheme also allows for the cancelling out of $l_o$, and thus, noise generated by the emitter 1304 can be cancelled out or reduced. In addition, since the scheme employs a mean path length difference, any changes in mean path length and topological variations from patient to patient are easily accounted. Furthermore, this bulk-measurement scheme can be extended across multiple wavelengths. This flexibility and other features allow embodiments of the present disclosure to measure blood analytes like glucose.

For example, as noted, the non-pulsatile, bulk measurements can be combined with pulsatile measurements to more accurately measure analytes like glucose. In particular, the non-pulsatile, bulk measurement can be used to confirm or validate the amount of glucose, protein, etc. in the pulsatile measurements taken at the tissue at the measurement site(s) 1302. The pulsatile measurements can be used to measure the amount of glucose, hemoglobin, or the like that is present in the blood. Accordingly, these different measurements can be combined to thus determine analytes like blood glucose.

Figure 14A:
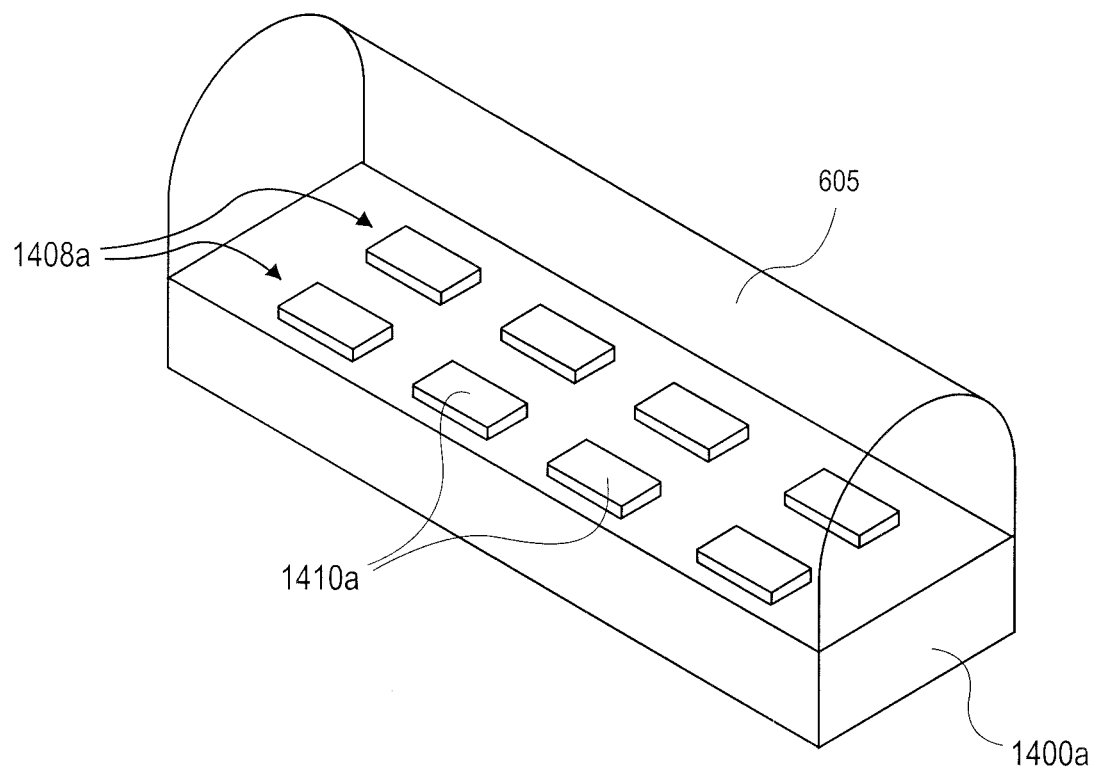
FIG. 14A illustrates another example detector portion having a partially cylindrical protrusion that can be employed in an embodiment of a sensor, according to an embodiment of the disclosure.

FIG. 14A illustrates an embodiment of a detector submount 1400a positioned beneath the partially cylindrical protrusion 605 of FIG. 6 (or alternatively, the protrusion 605b). The detector submount 1400a includes two rows 1408a of detectors 1410a. The partially cylindrical protrusion 605 can facilitate reducing the number and/or size of detectors used in a sensor because the protrusion 605 can act as a lens that focuses light onto a smaller area.

To illustrate, in some sensors that do not include the partially cylindrical protrusion 605, sixteen detectors can be used, including four rows of four detectors each. Multiple rows of detectors can be used to measure certain analytes, such as glucose or total hemoglobin, among others. Multiple rows of detectors can also be used to detect light piping (e.g., light that bypasses the measurement site). However, using more detectors in a sensor can add cost, complexity, and noise to the sensor.

Figure 14B:
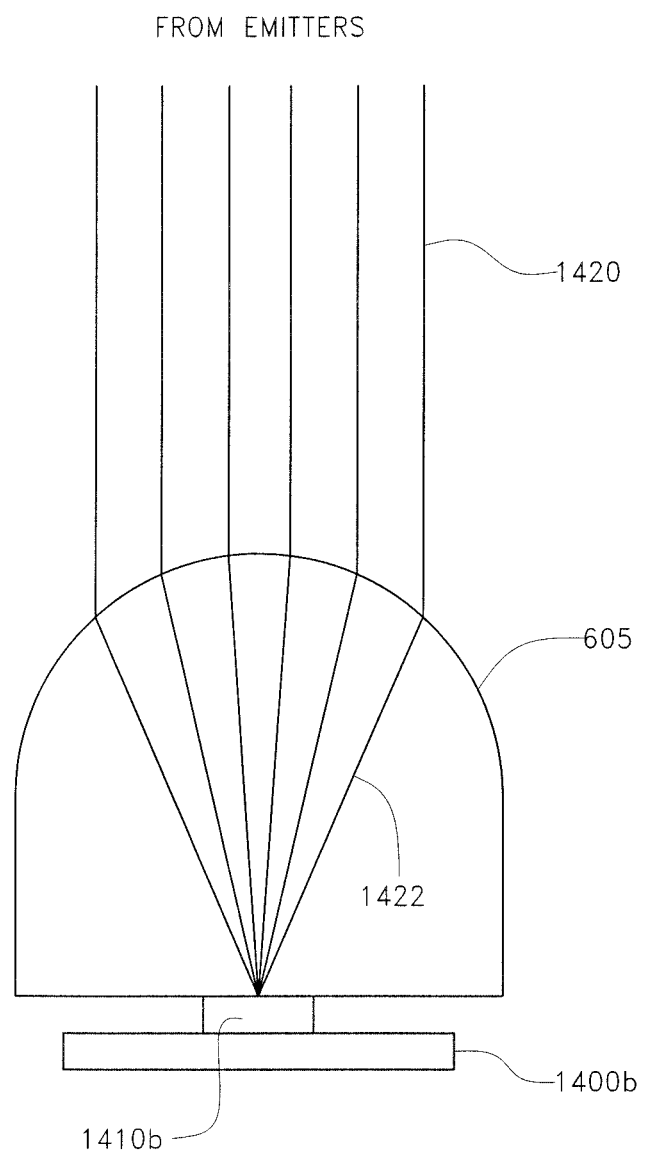
FIG. 14B depicts a front elevation view of the partially cylindrical protrusion of FIG. 14A.

Applying the partially cylindrical protrusion 605 to such a sensor, however, could reduce the number of detectors or rows of detectors used while still receiving the substantially same amount of light, due to the focusing properties of the protrusion 605 (see FIG. 14B). This is the example situation illustrated in FIG. 14—two rows 1408a of detectors 1410a are used instead of four. Advantageously, in certain embodiments, the resulting sensor can be more cost effective, have less complexity, and have an improved SNR, due to fewer and/or smaller photodiodes.

In other embodiments, using the partially cylindrical protrusion 605 can allow the number of detector rows to be reduced to one or three rows of four detectors. The number of detectors in each row can also be reduced. Alternatively, the number of rows might not be reduced but the size of the detectors can be reduced. Many other configurations of detector rows and sizes can also be provided.

FIG. 14B depicts a front elevation view of the partially cylindrical protrusion 605 (or alternatively, the protrusion 605b) that illustrates how light from emitters (not shown) can be focused by the protrusion 605 onto detectors. The protrusion 605 is placed above a detector submount 1400b having one or more detectors 1410b disposed thereon. The submount 1400b can include any number of rows of detectors 1410, although one row is shown.

Light, represented by rays 1420, is emitted from the emitters onto the protrusion 605. These light rays 1420 can be attenuated by body tissue (not shown). When the light rays 1420 enter the protrusion 605, the protrusion 605 acts as a lens to refract the rays into rays 1422. This refraction is caused in certain embodiments by the partially cylindrical shape of the protrusion 605. The refraction causes the rays 1422 to be focused or substantially focused on the one or more detectors 1410b. Since the light is focused on a smaller area, a sensor including the protrusion 605 can include fewer detectors to capture the same amount of light compared with other sensors.

Figure 14C:
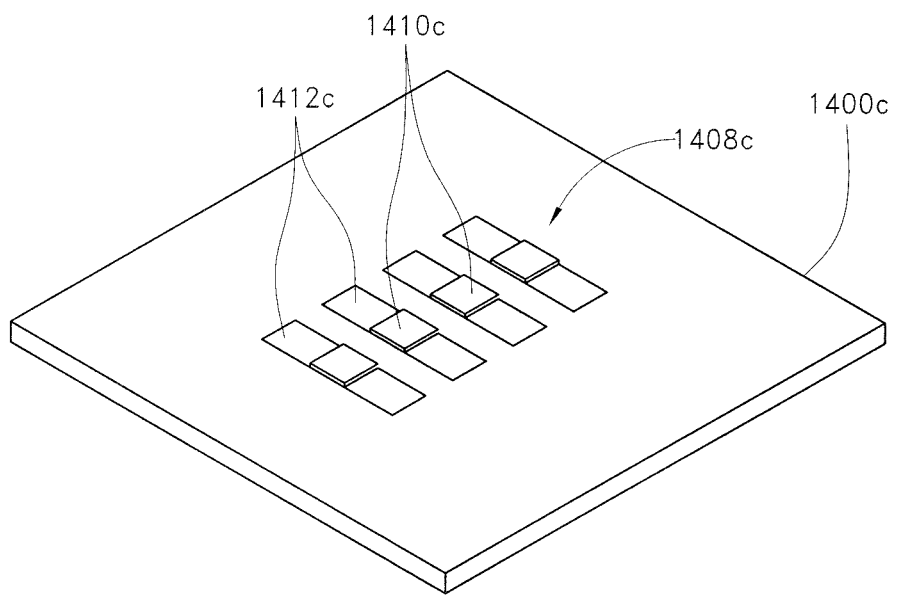
FIGS. 14C through 14E illustrate embodiments of a detector submount.

FIG. 14C illustrates another embodiment of a detector submount 1400c, which can be disposed under the protrusion 605b (or alternatively, the protrusion 605). The detector submount 1400c includes a single row 1408c of detectors 1410c. The detectors are electrically connected to conductors 1412c, which can be gold, silver, copper, or any other suitable conductive material.

Figure 14D:
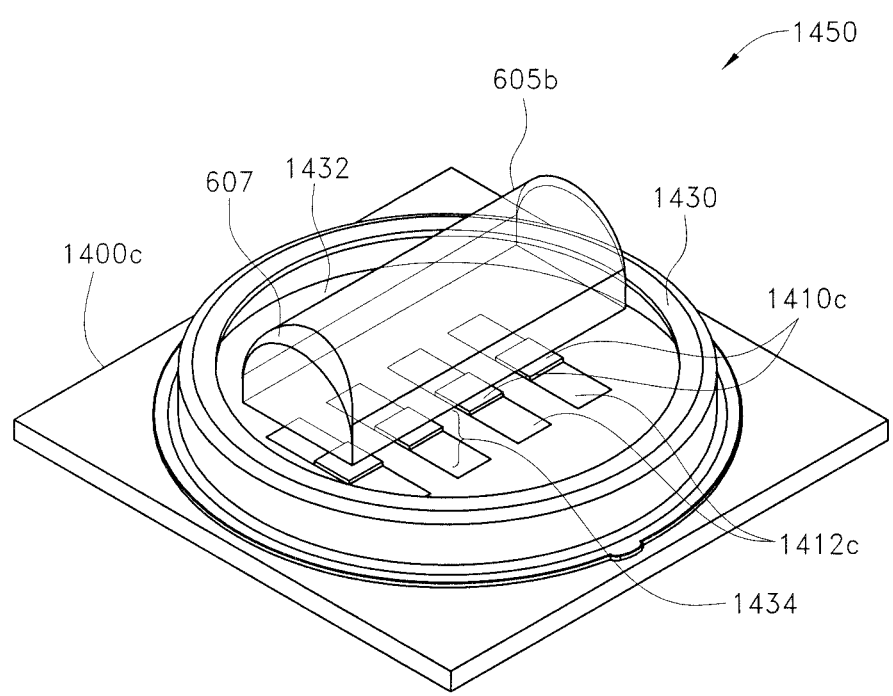
Figure 14E:
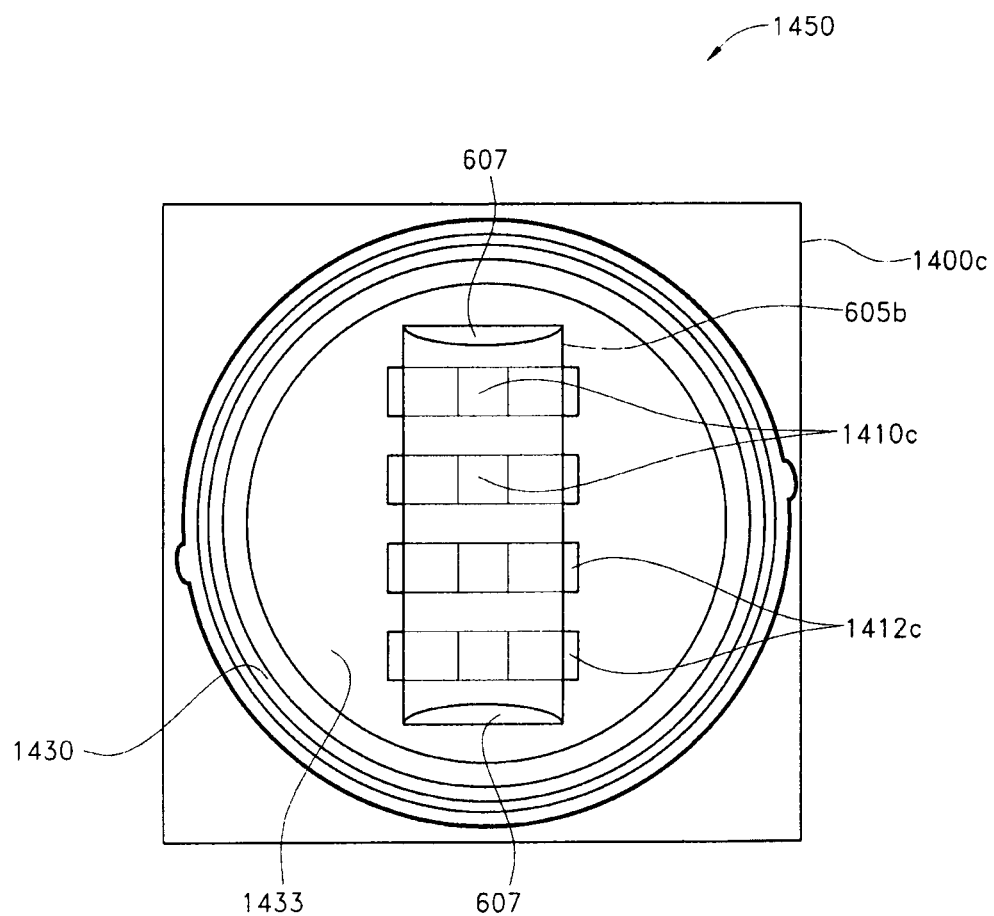

The detector submount 1400c is shown positioned under the protrusion 605b in a detector subassembly 1450 illustrated in FIG. 14D. A top-down view of the detector subassembly 1450 is also shown in FIG. 14E. In the detector subassembly 1450, a cylindrical housing 1430 is disposed on the submount 1400c. The cylindrical housing 1430 includes a transparent cover 1432, upon which the protrusion 605b is disposed. Thus, as shown in FIG. 14D, a gap 1434 exists between the detectors 1410c and the protrusion 605b. The height of this gap 1434 can be chosen to increase or maximize the amount of light that impinges on the detectors 1410c.

The cylindrical housing 1430 can be made of metal, plastic, or another suitable material. The transparent cover 1432 can be fabricated from glass or plastic, among other materials. The cylindrical housing 1430 can be attached to the submount 1400c at the same time or substantially the same time as the detectors 1410c to reduce manufacturing costs. A shape other than a cylinder can be selected for the housing 1430 in various embodiments.

In certain embodiments, the cylindrical housing 1430 (and transparent cover 1432) forms an airtight or substantially airtight or hermetic seal with the submount 1400c. As a result, the cylindrical housing 1430 can protect the detectors 1410c and conductors 1412c from fluids and vapors that can cause corrosion. Advantageously, in certain embodiments, the cylindrical housing 1430 can protect the detectors 1410c and conductors 1412c more effectively than currently-available resin epoxies, which are sometimes applied to solder joints between conductors and detectors.

In embodiments where the cylindrical housing 1430 is at least partially made of metal, the cylindrical housing 1430 can provide noise shielding for the detectors 1410c. For example, the cylindrical housing 1430 can be soldered to a ground connection or ground plane on the submount 1400c, which allows the cylindrical housing 1430 to reduce noise. In another embodiment, the transparent cover 1432 can include a conductive material or conductive layer, such as conductive glass or plastic. The transparent cover 1432 can include any of the features of the noise shields 790 described above.

The protrusion 605b includes the chamfered edges 607 described above with respect to FIG. 6E. These chamfered edges 607 can allow a patient to more comfortably slide a finger over the protrusion 605b when inserting the finger into the sensor 301f.

Figure 14F:
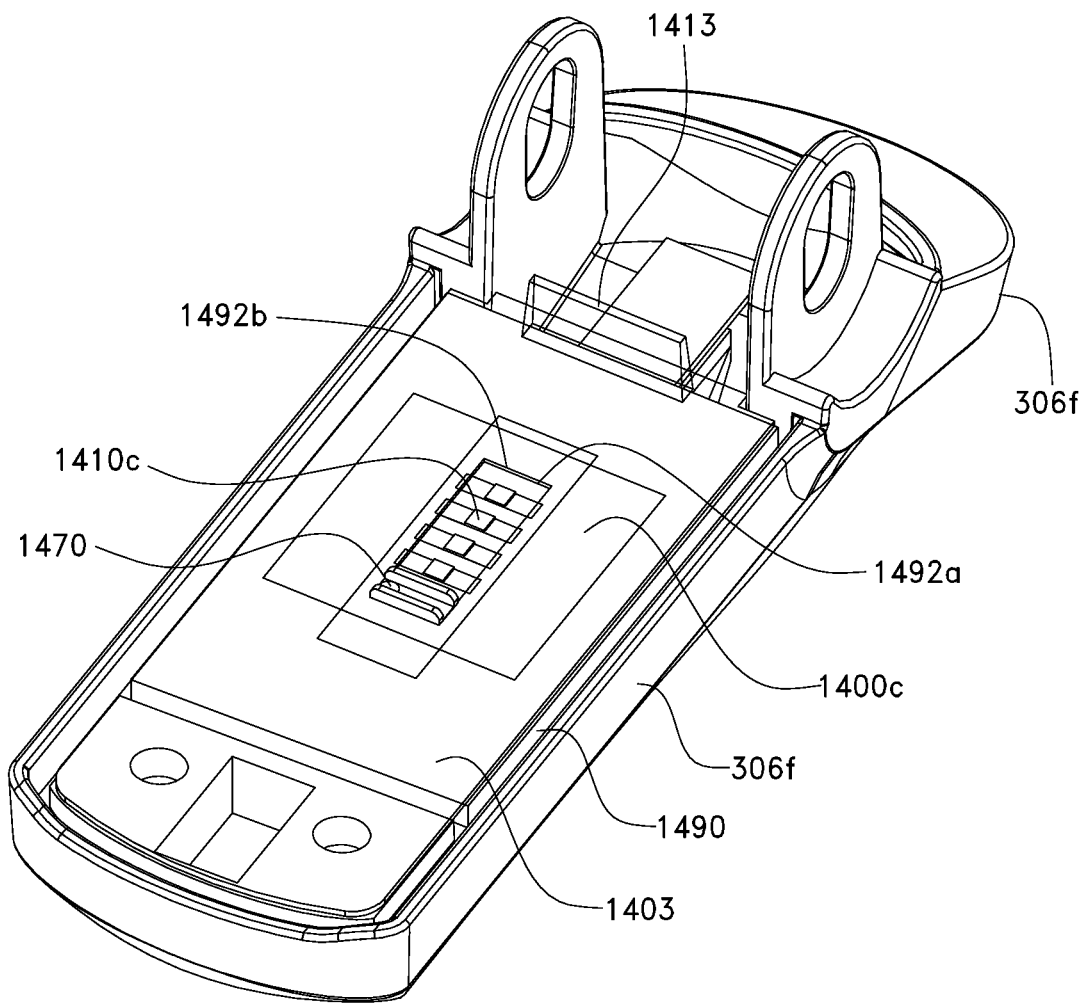
FIGS. 14F through 14H illustrate embodiment of portions of a detector shell.

FIG. 14F illustrates a portion of the detector shell 306f, which includes the detectors 1410c on the substrate 1400c. The substrate 1400c is enclosed by a shielding enclosure 1490, which can include the features of the shielding enclosures 790a, 790b described above (see also FIG. 17). The shielding enclosure 1490 can be made of metal. The shielding enclosure 1490 includes a window 1492a above the detectors 1410c, which allows light to be transmitted onto the detectors 1410c.

A noise shield 1403 is disposed above the shielding enclosure 1490. The noise shield 1403, in the depicted embodiment, includes a window 1492a corresponding to the window 1492a. Each of the windows 1492a, 1492b can include glass, plastic, or can be an opening without glass or plastic. In some embodiments, the windows 1492a, 1492b may be selected to have different sizes or shapes from each other.

The noise shield 1403 can include any of the features of the conductive glass described above. In the depicted embodiment, the noise shield 1403 extends about three-quarters of the length of the detector shell 306f. In other embodiments, the noise shield 1403 could be smaller or larger. The noise shield 1403 could, for instance, merely cover the detectors 1410c, the submount 1400c, or a portion thereof. The noise shield 1403 also includes a stop 1413 for positioning a measurement site within the sensor 301f. Advantageously, in certain embodiments the noise shield 1403 can reduce noise caused by light piping.

A thermistor 1470 is also shown. The thermistor 1470 is attached to the submount 1400c and protrudes above the noise shield 1403. As described above, the thermistor 1470 can be employed to measure a temperature of a measurement site. Such a temperature can be helpful in correcting for wavelength drift due to changes in water absorption, which can be temperature dependent, thereby providing more accurate data useful in detecting blood analytes like glucose.

In the depicted embodiment, the detectors 1410c are not enclosed in the cylindrical housing 1430. In an alternative embodiment, the cylindrical housing 1430 encloses the detectors 1410c and is disposed under the noise shield 1403. In another embodiment, the cylindrical housing 1430 encloses the detectors 1410c and the noise shield 1403 is not used. If both the cylindrical housing 1403 and the noise shield 1403 are used, either or both can have noise shielding features.

Figure 14G:
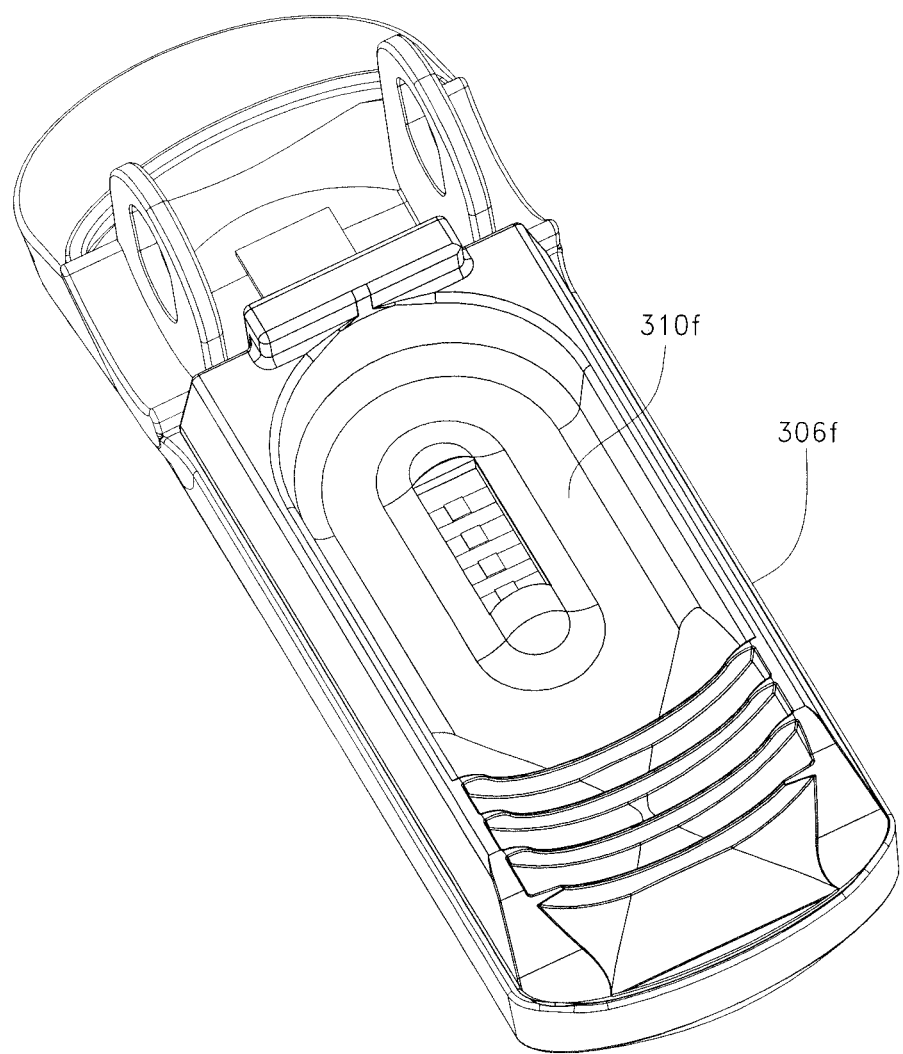
Figure 14H:
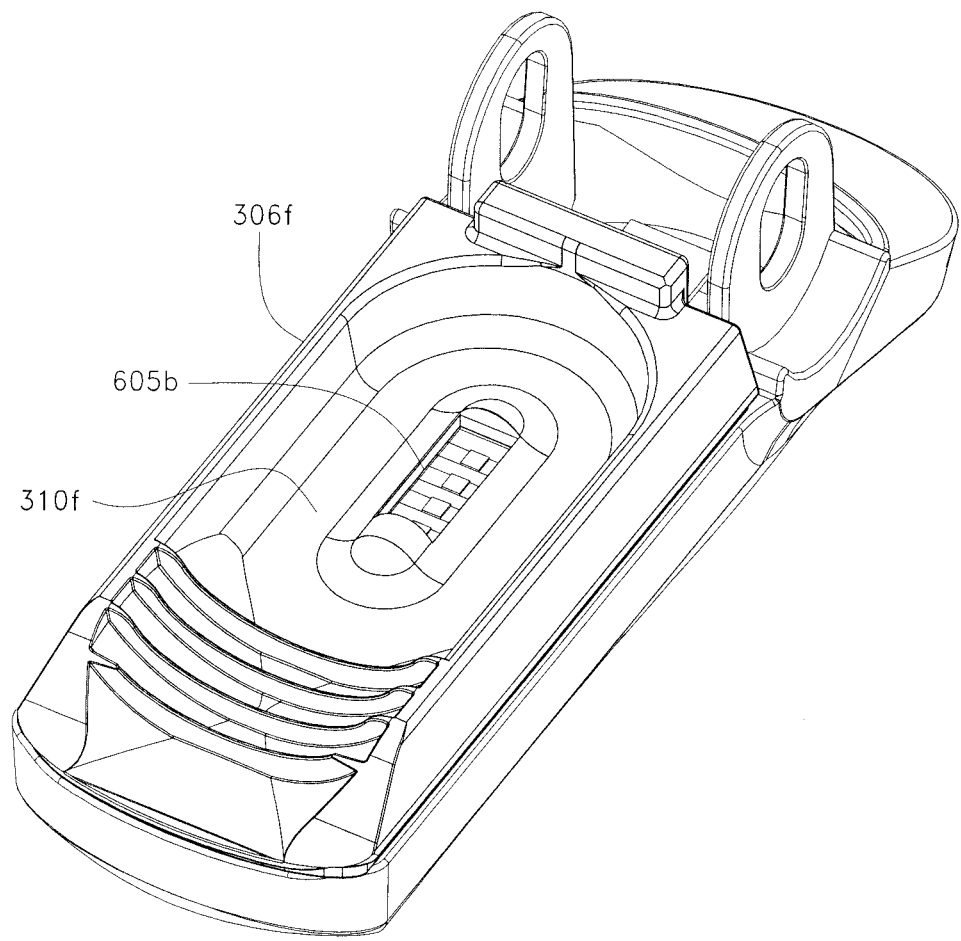

FIG. 14G illustrates the detector shell 306f of FIG. 14F, with the finger bed 310f disposed thereon. FIG. 14H illustrates the detector shell 306f of FIG. 14G, with the protrusion 605b disposed in the finger bed 310f.

Figure 14I:
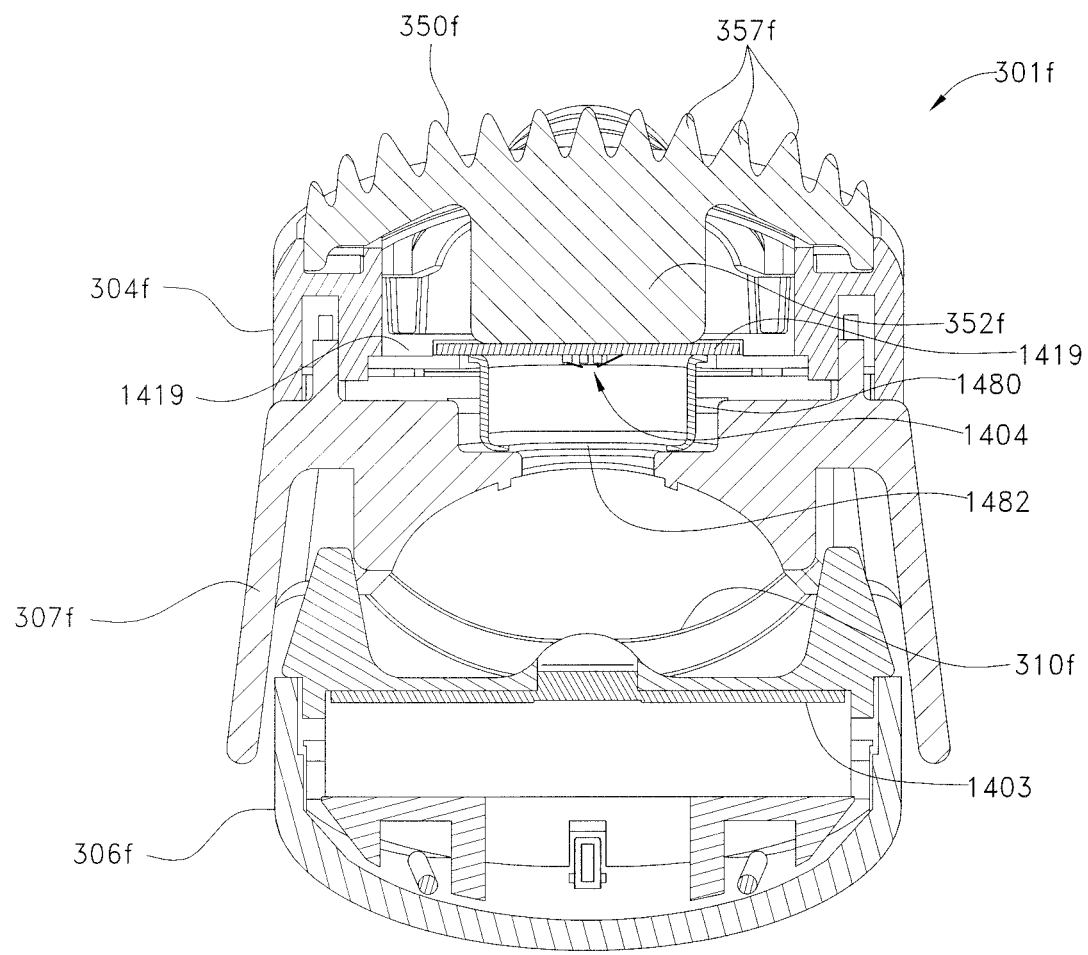
FIG. 14I illustrates a cutaway view of an embodiment of a sensor.

FIG. 14I illustrates a cutaway view of the sensor 301f. Not all features of the sensor 301f are shown, such as the protrusion 605b. Features shown include the emitter and detector shells 304f, 306f, the flaps 307f, the heat sink 350f and fins 351f, the finger bed 310f, and the noise shield 1403.

In addition to these features, emitters 1404 are depicted in the emitter shell 304f. The emitters 1404 are disposed on a submount 1401, which is connected to a circuit board 1419. The emitters 1404 are also enclosed within a cylindrical housing 1480. The cylindrical housing 1480 can include all of the features of the cylindrical housing 1430 described above. For example, the cylindrical housing 1480 can be made of metal, can be connected to a ground plane of the submount 1401 to provide noise shielding, and can include a transparent cover 1482.

The cylindrical housing 1480 can also protect the emitters 1404 from fluids and vapors that can cause corrosion. Moreover, the cylindrical housing 1480 can provide a gap between the emitters 1404 and the measurement site (not shown), which can allow light from the emitters 1404 to even out or average out before reaching the measurement site.

The heat sink 350f, in addition to including the fins 351f, includes a protuberance 352f that extends down from the fins 351f and contacts the submount 1401. The protuberance 352f can be connected to the submount 1401, for example, with thermal paste or the like. The protuberance 352f can sink heat from the emitters 1404 and dissipate the heat via the fins 351f.

Figure 15A:
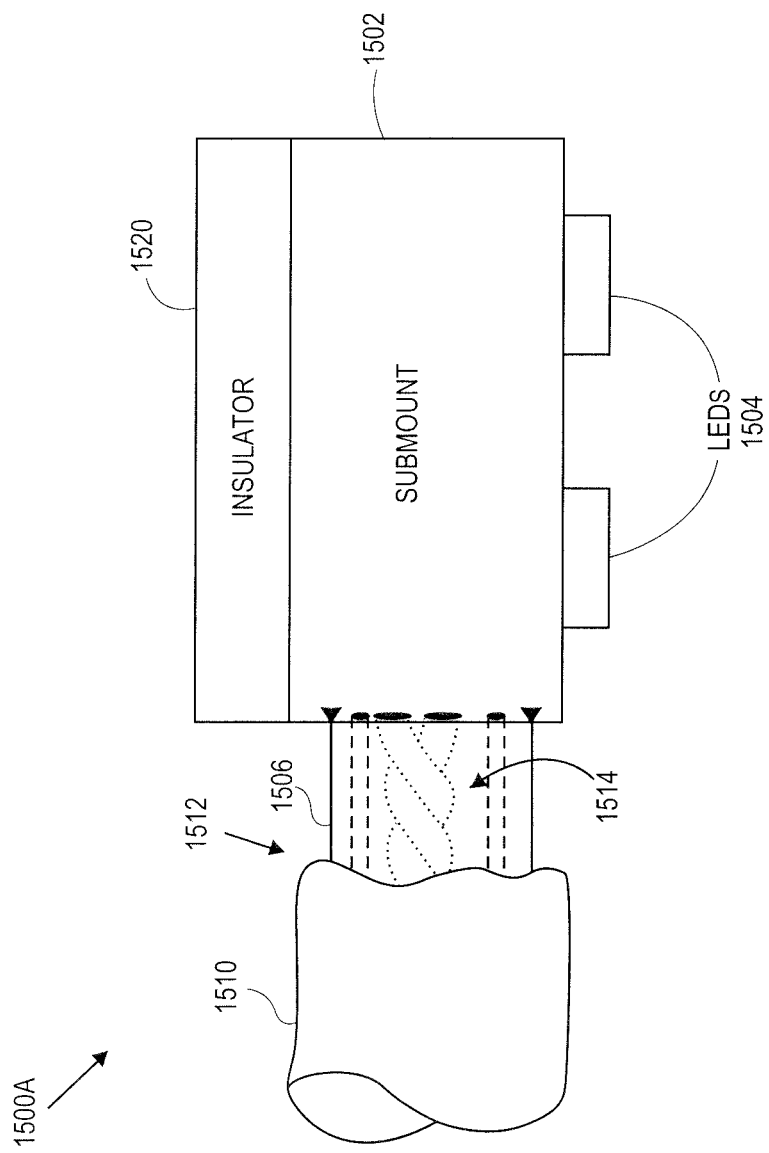
FIGS. 15A through 15F illustrate embodiments of sensors that include heat sink features.
Figure 15B:
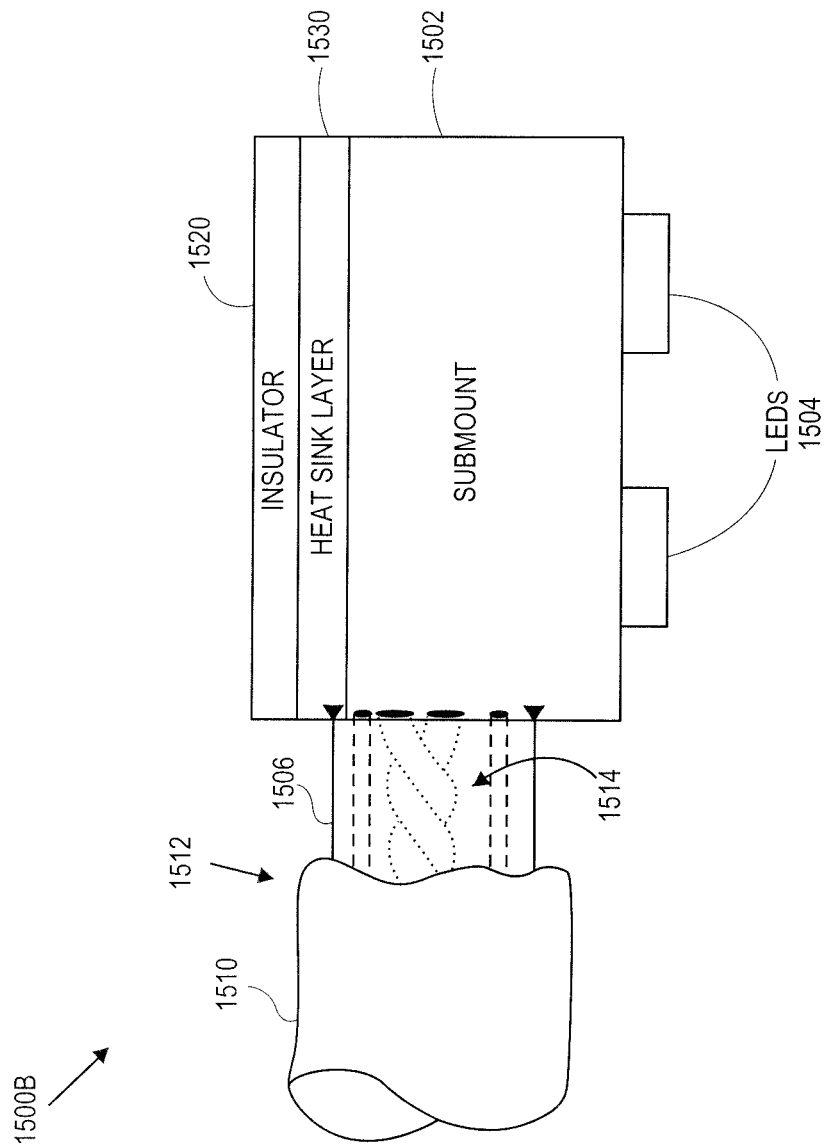

FIGS. 15A and 15B illustrate embodiments of sensor portions 1500A, 1500B that include alternative heat sink features to those described above. These features can be incorporated into any of the sensors described above. For example, any of the sensors above can be modified to use the heat sink features described below instead of or in addition to the heat sink features of the sensors described above.

The sensor portions 1500A, 1500B shown include LED emitters 1504; however, for ease of illustration, the detectors have been omitted. The sensor portions 1500A, 1500B shown can be included, for example, in any of the emitter shells described above.

The LEDs 1504 of the sensor portions 1500A, 1500B are connected to a substrate or submount 1502. The submount 1502 can be used in place of any of the submounts described above. The submount 1502 can be a non-electrically conducting material made of any of a variety of materials, such as ceramic, glass, or the like. A cable 1512 is attached to the submount 1502 and includes electrical wiring 1514, such as twisted wires and the like, for communicating with the LEDs 1504. The cable 1512 can correspond to the cables 212 described above.

Although not shown, the cable 1512 can also include electrical connections to a detector. Only a portion of the cable 1512 is shown for clarity. The depicted embodiment of the cable 1512 includes an outer jacket 1510 and a conductive shield 1506 disposed within the outer jacket 1510. The conductive shield 1506 can be a ground shield or the like that is made of a metal such as braided copper or aluminum. The conductive shield 1506 or a portion of the conductive shield 1506 can be electrically connected to the submount 1502 and can reduce noise in the signal generated by the sensor 1500A, 1500B by reducing RF coupling with the wires 1514. In alternative embodiments, the cable 1512 does not have a conductive shield. For example, the cable 1512 could be a twisted pair cable or the like, with one wire of the twisted pair used as a heat sink.

Referring specifically to FIG. 15A, in certain embodiments, the conductive shield 1506 can act as a heat sink for the LEDs 1504 by absorbing thermal energy from the LEDs 1504 and/or the submount 1502. An optional heat insulator 1520 in communication with the submount 1502 can also assist with directing heat toward the conductive shield 1506. The heat insulator 1520 can be made of plastic or another suitable material. Advantageously, using the conductive shield 1506 in the cable 1512 as a heat sink can, in certain embodiments, reduce cost for the sensor.

Referring to FIG. 15B, the conductive shield 1506 can be attached to both the submount 1502 and to a heat sink layer 1530 sandwiched between the submount 1502 and the optional insulator 1520. Together, the heat sink layer 1530 and the conductive shield 1506 in the cable 1512 can absorb at least part of the thermal energy from the LEDs and/or the submount 1502.

Figure 15C:
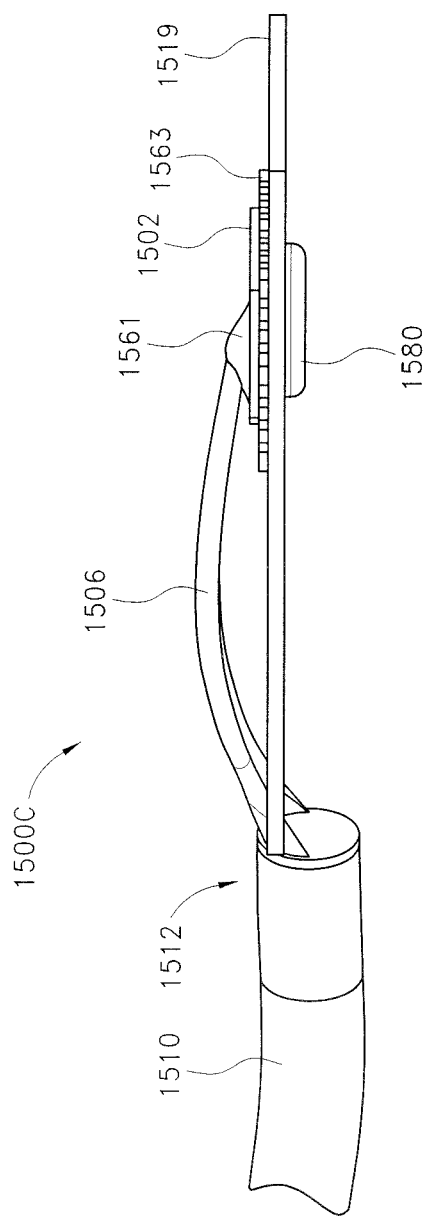
Figure 15D:
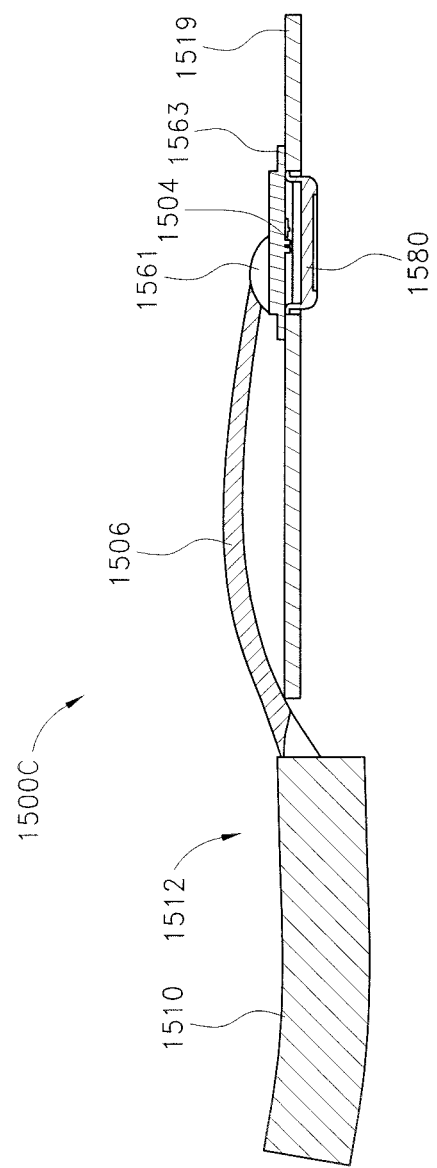

FIGS. 15C and 15D illustrate implementations of a sensor portion 1500C that includes the heat sink features of the sensor portion 1500A described above with respect to FIG. 15A. The sensor portion 1500C includes the features of the sensor portion 1500A, except that the optional insulator 1520 is not shown. FIG. 15D is a side cutaway view of the sensor portion 1500C that shows the emitters 1504.

The cable 1512 includes the outer jacket 1510 and the conductive shield 1506. The conductive shield 1506 is soldered to the submount 1502, and the solder joint 1561 is shown. In some embodiments, a larger solder joint 1561 can assist with removing heat more rapidly from the emitters 1504. Various connections 1563 between the submount 1502 and a circuit board 1519 are shown. In addition, a cylindrical housing 1580, corresponding to the cylindrical housing 1480 of FIG. 14I, is shown protruding through the circuit board 1519. The emitters 1504 are enclosed in the cylindrical housing 1580.

Figure 15E:
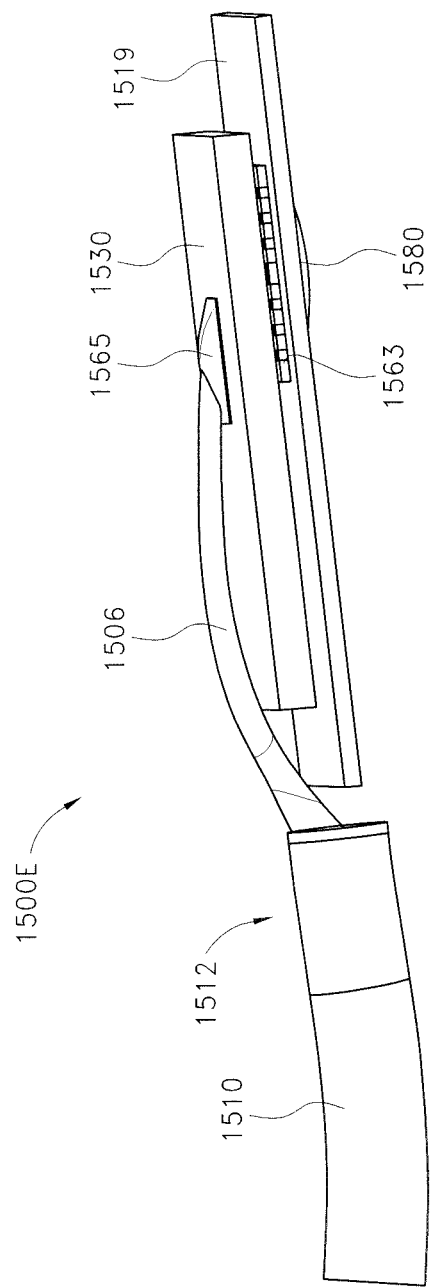
Figure 15F:
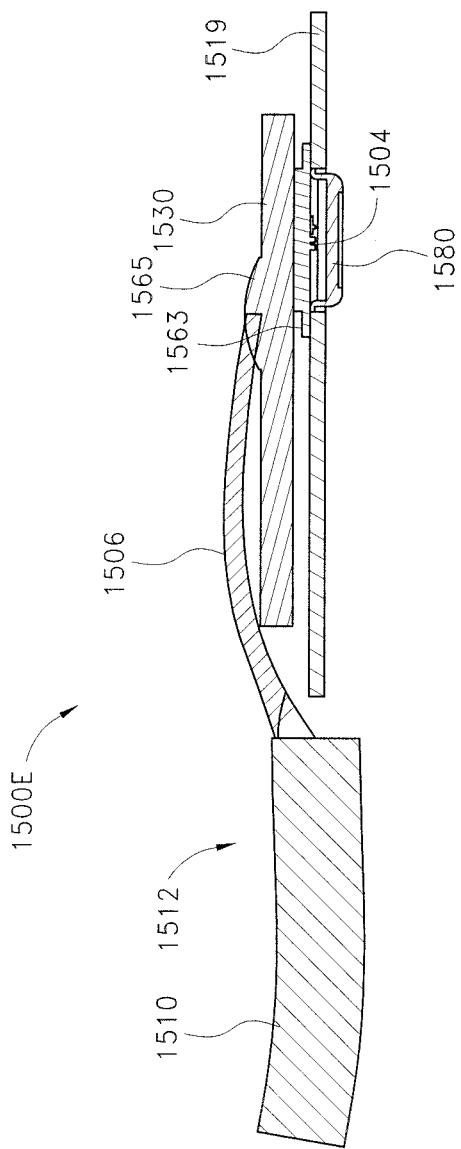

FIGS. 15E and 15F illustrate implementations of a sensor portion 1500E that includes the heat sink features of the sensor portion 1500B described above with respect to FIG. 15B. The sensor portion 1500E includes the heat sink layer 1530. The heat sink layer 1530 can be a metal plate, such as a copper plate or the like. The optional insulator 1520 is not shown. FIG. 15F is a side cutaway view of the sensor portion 1500E that shows the emitters 1504.

In the depicted embodiment, the conductive shield 1506 of the cable 1512 is soldered to the heat sink layer 1530 instead of the submount 1502. The solder joint 1565 is shown. In some embodiments, a larger solder joint 1565 can assist with removing heat more rapidly from the emitters 1504. Various connections 1563 between the submount 1502 and a circuit board 1519 are shown. In addition, the cylindrical housing 1580 is shown protruding through the circuit board 1519. The emitters 1504 are enclosed in the cylindrical housing 1580.

Figure 15G:
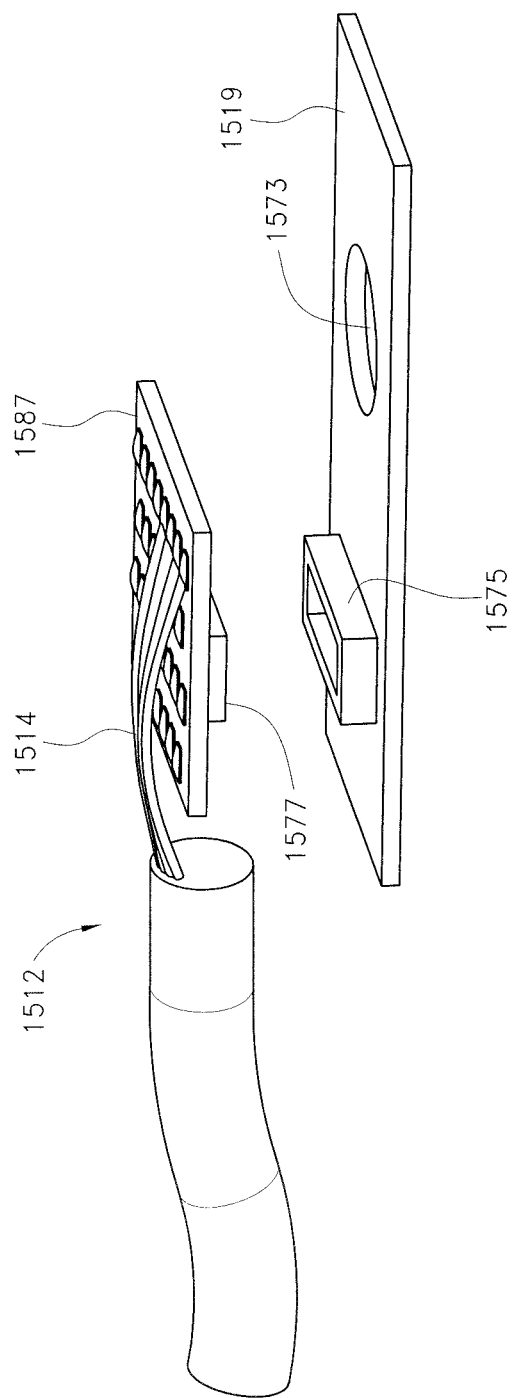
FIGS. 15G and 15H illustrate embodiments of connector features that can be used with any of the sensors described herein.
Figure 15H:
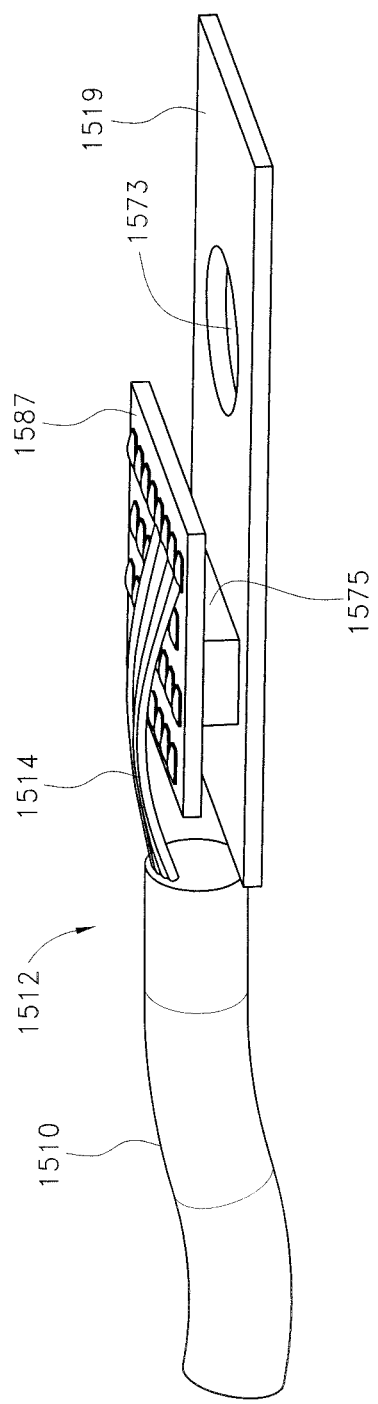

FIGS. 15G and 15H illustrate embodiments of connector features that can be used with any of the sensors described above with respect to FIGS. 1 through 15F. Referring to FIG. 15G, the circuit board 1519 includes a female connector 1575 that mates with a male connector 1577 connected to a daughter board 1587. The daughter board 1587 includes connections to the electrical wiring 1514 of the cable 1512. The connected boards 1519, 1587 are shown in FIG. 15H. Also shown is a hole 1573 that can receive the cylindrical housing 1580 described above.

Advantageously, in certain embodiments, using a daughter board 1587 to connect to the circuit board 1519 can enable connections to be made more easily to the circuit board 1519. In addition, using separate boards can be easier to manufacture than a single circuit board 1519 with all connections soldered to the circuit board 1519.

FIGS. 16A and 16B illustrate embodiments of disposable optical sensors 1600. In an embodiment, any of the features described above, such as protrusion, shielding, and/or heat sink features, can be incorporated into the disposable sensors 1600 shown. For instance, the sensors 1600 can be used as the sensors 101 in the system 100 described above with respect to FIG. 1. Moreover, any of the features described above, such as protrusion, shielding, and/or heat sink features, can be implemented in other disposable sensor designs that are not depicted herein.

The sensors 1600 include an adult/pediatric sensor 1610 for finger placement and a disposable infant/neonate sensor 1602 configured for toe, foot or hand placement. Each sensor 1600 has a tape end 1610 and an opposite connector end 1620 electrically and mechanically interconnected via a flexible coupling 1630. The tape end 1610 attaches an emitter and detector to a tissue site. Although not shown, the tape end 1610 can also include any of the protrusion, shielding, and/or heat sink features described above. The emitter illuminates the tissue site and the detector generates a sensor signal responsive to the light after tissue absorption, such as absorption by pulsatile arterial blood flow within the tissue site.

The sensor signal is communicated via the flexible coupling 1630 to the connector end 1620. The connector end 1620 can mate with a cable (not shown) that communicates the sensor signal to a monitor (not shown), such as any of the cables or monitors shown above with respect to FIGS. 2A through 2D. Alternatively, the connector end 1620 can mate directly with the monitor.

Figure 17:
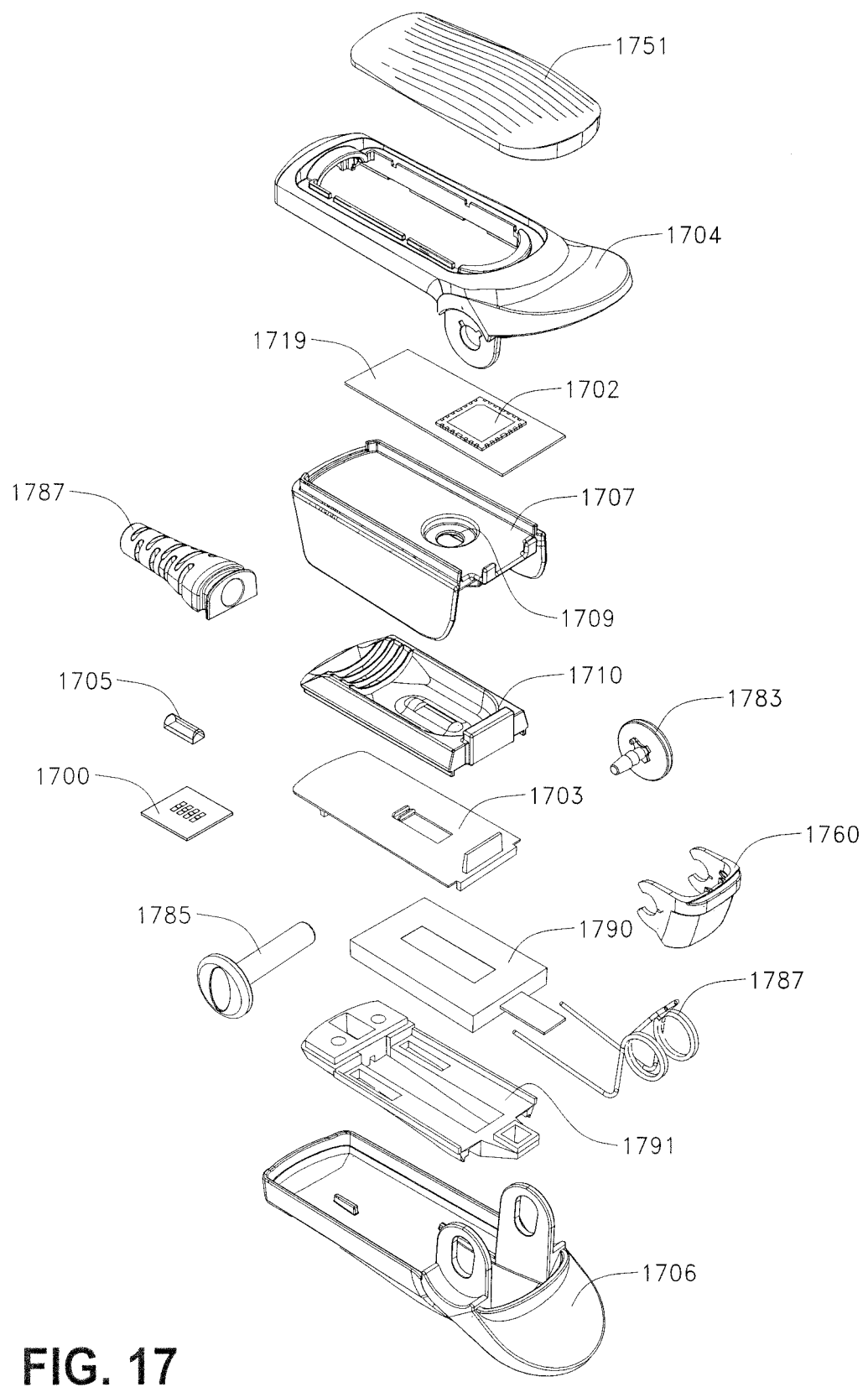
FIG. 17 illustrates an exploded view of certain components of an example sensor.

FIG. 17 illustrates an exploded view of certain of the components of the sensor 301f described above. A heat sink 1751 and a cable 1781 attach to an emitter shell 1704. The emitter shell attaches to a flap housing 1707. The flap housing 1707 includes a receptacle 1709 to receive a cylindrical housing 1480/1580 (not shown) attached to an emitter submount 1702, which is attached to a circuit board 1719.

A spring 1787 attaches to a detector shell 1706 via pins 1783, 1785, which hold the emitter and detector shells 1704, 1706 together. A support structure 1791 attaches to the detector shell 1706, which provides support for a shielding enclosure 1790. A noise shield 1713 attaches to the shielding enclosure 1790. A detector submount 1700 is disposed inside the shielding enclosure 1790. A finger bed 1710 attaches to the noise shield 1703. A partially cylindrical protrusion 1705 is disposed in the finger bed 1710. Moreover, a flex circuit cover 1706 attaches to the pins 1783, 1785. Although not shown, a flex circuit can also be provided that connects the circuit board 1719 with the submount 1700 (or a circuit board to which the submount 1700 is connected).

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While certain embodiments of the inventions disclosed herein have been described, these embodiments have been presented by way of example only, and are not intended to limit the scope of the inventions disclosed herein. Indeed, the novel methods and systems described herein can be embodied in a variety of other forms; furthermore, various omissions, substitutions and changes in the form of the methods and systems described herein can be made without departing from the spirit of the inventions disclosed herein. The claims and their equivalents are intended to cover such forms or modifications as would fall within the scope and spirit of certain of the inventions disclosed herein.

What is claimed is:

1. An optical medical sensor configured to detect light attenuated by body tissue of a patient, the sensor comprising:
a sensor housing comprising a first shell and a second shell pivotally connected together, the first and second shells each shaped to accept body tissue of a medical patient;
an emitter disposed in the first shell, the emitter configured to emit light on the body tissue of the medical patient;
a detector disposed on a submount in the second shell, the detector configured to receive light attenuated by the body tissue along an optical path;
a shielding disposed between the emitter and the detector, the shielding comprising a substantially-transparent, electrically-conductive material in the optical path; and
a cylindrical housing that at least partially encloses the detector, the cylindrical housing disposed on the submount and being at least partially made of a material that provides noise shielding for the detector, and wherein the cylindrical housing comprises a cover that includes the shielding.

2. The sensor of claim 1, wherein the cylindrical housing comprises metal.

3. The sensor of claim 1, wherein the cylindrical housing, submount, and shielding provide a substantially airtight seal to protect the detector from fluids and vapors.

4. The sensor of claim 1, wherein the shielding comprises conductive-coated glass.

5. The sensor of claim 1, wherein the shielding comprises conductive-coated plastic.

6. The sensor of claim 1, wherein the electrically-conductive material comprises indium tin oxide.

7. The sensor of claim 1, further comprising a partially-cylindrical protrusion disposed on the shielding.

8. The sensor of claim 1, further comprising a second cylindrical housing configured to at least partially enclose the emitter.

9. A conductive shield configured to shield noise interference from a light sensitive detector, the shield comprising:
a cylindrical housing coupled onto a detector submount, the cylindrical housing being at least partially made of a material that provides noise shielding;
a substantially transparent material positioned as a cover of the cylindrical housing; and
a conductive material disposed on at least a portion of the substantially transparent material;
wherein the conductive material is configured to be positioned between a light source and a light detector such that at least some light from said light source passes through said conductive material and impinges on said light detector.

10. The conductive shield of claim 9, wherein the conductive material is configured to be in electrical communication with a ground conductor.

11. The conductive shield of claim 10, wherein the conductive material conducts noise away from said detector toward the ground conductor.

12. The conductive shield of claim 9, wherein the substantially transparent material comprises plastic.

13. The conductive shield of claim 9, wherein the substantially transparent material comprises glass.

14. The conductive shield of claim 9, wherein a surface resistivity of the conductive material ranges from about 30 ohms per square inch to about 500 ohms per square inch.

15. The conductive shield of claim 9, wherein the conductive material comprises indium tin oxide.

16. The conductive shield of claim 9, wherein the conductive material is a coating on the substantially transparent material, said coating being distributed over the substantially transparent material in a manner selected from the group consisting of: distributed with an even thickness, distributed in varying thicknesses, distributed over periphery edges of the substantially transparent material, distributed in a speckled pattern, distributed in a grid, and distributed in lines.

17. The conductive shield of claim 9, wherein the cylindrical housing comprises metal.

18. The conductive shield of claim 9, further comprising a partially-cylindrical protrusion disposed on the shielding.

19. A system for shielding one or more photocommunicative devices, the system comprising:
an emitter configured to emit optical radiation;
a detector disposed on a submount;
a shielding device disposed between the emitter and the detector, the shielding device comprising a substantially-transparent, electrically-conductive material, the shielding device configured to pass at least a portion of the optical radiation to the detector and to reduce a noise received by the detector; and
a cylindrical housing, the cylindrical housing coupled onto the submount and comprising a material that provides noise shielding for the detector wherein the shielding device and the cylindrical housing are mechanically coupled.

20. The system of claim 19, wherein the substantially-transparent, electrically-conductive material comprises a layer of transparent material and a layer of conductive material.

21. The system of claim 20, wherein the layer of transparent material comprises a material selected from the group consisting of plastic and glass.

* * * * *

UNITED STATES PATENT AND TRADEMARK OFFICE
CERTIFICATE OF CORRECTION

| | | |
|---|---|---|
| PATENT NO. | : 8,577,431 B2 | Page 1 of 1 |
| APPLICATION NO. | : 12/497528 | |
| DATED | : November 5, 2013 | |
| INVENTOR(S) | : Lamego et al. | |

It is certified that error appears in the above-identified patent and that said Letters Patent is hereby corrected as shown below:

On the Title Page

Page 1 (item 63, Related U.S. Application Data) at line 3, Change "which is" to --and--.

In column 1 (page 3, item 56) at line 21, Under U.S. Patent Documents, Change "Gruhl" to --Kiani et al.--.

In column 2 (page 4, item 56) at line 55, Under Other Publications, Change "Anaylsis" to --Analysis--.

In the Specification

In column 6 at line 48, Change "embodiments" to --embodiments,--.

In column 6 at line 56, Change "disclosure" to --disclosure,--.

In column 13 at line 37, Change "attachment to to a" to --attachment to a--.

In column 13 at line 65, Change "patients" to --patient's--.

In column 14 at line 64, Change "patients" to --patient's--.

In column 17 at line 6, Change "of a the" to --of the--.

In column 19 at line 27, Change "and or" to --and/or--.

In column 24 at line 45, Change "fashion" to --fashion,--.

In column 25 at line 53, Change "site" to --site,--.

In the Claims

In column 34 at line 42, In Claim 19, Change "detector" to --detector,--.

Signed and Sealed this
Third Day of June, 2014

Michelle K. Lee
*Deputy Director of the United States Patent and Trademark Office*